(12) United States Patent
Owens et al.

(10) Patent No.: US 10,564,074 B2
(45) Date of Patent: Feb. 18, 2020

(54) METHODS FOR USING ROSE BENGAL FOR DETECTION OF CHEMICAL WARFARE AGENTS

(71) Applicant: The Government of the United States as Represented by the Secretary of the Air Force, Wright-Patterson AFB, OH (US)

(72) Inventors: Jeffery Ray Owens, Panama City, FL (US); Rashelle S. McDonald, Panama City, FL (US); Dmytro Volkov, Lowell, MA (US)

(73) Assignee: United States of America as represented by the Secretary of the Air Force, Wright-Patterson AFB, OH (US)

(*) Notice: Subject to any disclaimer, the term of this patent is extended or adjusted under 35 U.S.C. 154(b) by 0 days.

(21) Appl. No.: 15/058,431

(22) Filed: Mar. 2, 2016

(65) Prior Publication Data
US 2016/0258914 A1     Sep. 8, 2016

Related U.S. Application Data

(63) Continuation of application No. 14/520,545, filed on Oct. 22, 2014, now abandoned, and a continuation of
(Continued)

(51) Int. Cl.
*G01N 31/22* (2006.01)
*A62D 3/38* (2007.01)
(Continued)

(52) U.S. Cl.
CPC ............ *G01N 1/30* (2013.01); *A61L 2/18* (2013.01); *A62D 3/38* (2013.01); *G01N 21/78* (2013.01);
(Continued)

(58) Field of Classification Search
CPC ... A61L 2/18; Y10T 436/14222; G01N 31/22; G01N 2033/0096; G01N 1/30; G01N 33/52; G01N 2001/302; G01N 21/78
(Continued)

(56) References Cited

U.S. PATENT DOCUMENTS 6,239,048 B1     5/2001   Wilson
8,916,341 B1 *  12/2014   Bystryak .............. G01N 33/542
                                                           435/4
(Continued)

FOREIGN PATENT DOCUMENTS

WO     2011035161     3/2011
WO     2013138916     9/2013

OTHER PUBLICATIONS

United States Patent and Trademark Office, Final Office Action in U.S. Appl. No. 14/520,569, dated Mar. 30, 2016, 7 pages total.
(Continued)

*Primary Examiner* — Rebecca M Fritchman
(74) *Attorney, Agent, or Firm* — AFMCLO/JAZ; Chastity Whitaker

(57) ABSTRACT

Rose Bengal for detecting a presence of chemical warfare agents. A method of detecting presence of a chemical warfare agent and includes applying a quinoid form of Rose Bengal to a substrate. When the substrate is exposed to the chemical warfare agent, a lactone form of Rose Bengal is spectrally observed because presence of the chemical warfare agent converts the quinoid form to the lactone form of Rose Bengal.

11 Claims, 51 Drawing Sheets

Related U.S. Application Data application No. 14/520,569, filed on Oct. 22, 2014, now Pat. No. 9,470,610.

(60) Provisional application No. 61/894,112, filed on Oct. 22, 2013.

(51) Int. Cl.
| | | |
|---|---|---|
| *G01N 1/30* | (2006.01) | |
| *G01N 33/52* | (2006.01) | |
| *G01N 21/78* | (2006.01) | |
| *A61L 2/18* | (2006.01) | |
| *G01N 33/00* | (2006.01) | |
| *A62D 101/02* | (2007.01) | |

(52) U.S. Cl.
CPC ........... *G01N 21/783* (2013.01); *G01N 31/22* (2013.01); *G01N 31/224* (2013.01); *G01N 33/52* (2013.01); *A62D 2101/02* (2013.01); *G01N 2001/302* (2013.01); *G01N 2033/0096* (2013.01); *Y10T 436/142222* (2015.01)

(58) Field of Classification Search
USPC ........................................ 436/93; 422/82.05
See application file for complete search history.

(56) References Cited

U.S. PATENT DOCUMENTS

| | | | |
|---|---|---|---|
| 2005/0227369 A1 | 10/2005 | Richardson et al. | |
| 2006/0147927 A1* | 7/2006 | Geddes | C12Q 1/6816 435/6.12 |
| 2009/0317293 A1 | 12/2009 | Street | |
| 2010/0227766 A1* | 9/2010 | Walt | C07D 219/06 506/7 |
| 2011/0104052 A1* | 5/2011 | Barnett | A61K 9/0019 424/1.21 |
| 2013/0183773 A1 | 7/2013 | Tseng et al. | |
| 2013/0184267 A1 | 7/2013 | Ash | |
| 2014/0227723 A1* | 8/2014 | Ingber | A61K 47/48369 435/7.92 |
| 2014/0356621 A1 | 12/2014 | Owens et al. | |

OTHER PUBLICATIONS

Wikipedia, "Rose bengal," http://en.wikipedia.org/wiki/Rose_bengal, Accessed Dec. 9, 2014, 3 pages total.

Wikipedia, "Singlet oxygen," http://en.wikipedia.org/wiki/Singlet_oxygen, Accessed Dec. 9, 2014, 3 pages total.

United States Patent and Trademark Office, Non-Final Office Action in related U.S. Appl. No. 14/520,545, dated Jun. 23, 2015, 12 pages total.

European Patent Office, International Search Report and Written Opinion in PCT/GB2014/053144, filed Oct. 22, 2014, 12 pages total.

A. Mills et al., "Photoreduction of water sensitised by Rose Bengal," J. Chem. Soc, Faraday Trans 2., vol. 82 (1986) 2291-2303.

V. K. Gupta et al., "Batch and bulk removal of hazardous colouring agent Rose Bengal by adsorption techniques using bottom ash as adsorbent," RSC Advances, vol. 2 (2012) 8381.

Y. Guo et al., "Rose Bengal-decorated silica nanoparticles as photosensitizers for inactivation of gram-positive bacteria," Nanotech., vol. 21 (2010) 65102.

S. Tamagaki et al., "Polymer-based sensitizers for photochemical reactions. Silica Gel as a Support," J. Org. Chem., vol. 45 (1980) 1573-1576.

J. G. Banks et al., "The cytotoxic and photodynamic inactivation of micro-organisms by Rose Bengal," J. Appl. Bacteriol., vol. 58 (1985) 391-400.

J. Paczkowski et al., "Photophysical properties of Rose Bengal and its derivatives (XII)," J. Free Radicals in Biol & Med., vol. 1 (1985) 341-351.

C. Akerlind et al., "Optical properties and switching of a Rose Bengal derivative: a spectroscopic ellipsometry study," Thin Solid Films, vol. 519 (2011) 3582-3586.

B. Salter et al., "N-chloramide modified NOMEX as a regenerable self-decontaminating material for protection against chemical warfare agents," J. Mater. Sci., vol. 44 (2009) 2069-2078.

United States Patent and Trademark Office, Final Office Action in related U.S. Appl. No. 14/520,545, dated Oct. 8, 2015, 13 pages total.

United States Patent and Trademark Office, Non-Final Office Action in related U.S. Appl. No. 14/520,569, dated Jan. 20, 2016, 9 pages total.

\* cited by examiner

US 10,564,074 B2

METHODS FOR USING ROSE BENGAL FOR DETECTION OF CHEMICAL WARFARE AGENTS

This application is a continuation of U.S. application Ser. Nos. 14/520,545 and 14/520,569, filed Oct. 22, 2014, which claim the benefit of and priority to prior filed Provisional Application Ser. No. 61/894,112, filed 22 Oct. 2013. The application is also related to International Application No. PCT/GB2014/053,144, filed Oct. 21, 2014. The disclosure of each application is expressly incorporated herein by reference, in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to decontamination of substrates and assets and, more particularly, to methods and systems for detecting, decontaminating, and monitoring decontamination of substrates and assets.

BACKGROUND OF THE INVENTION

Traditional chemical warfare agent simulants and other problematic contaminants, such as pesticides, are difficult to detect and decontaminate, either by removal or decomposition. The U.S. Department of Defense has expended considerable effort in developing what are called "decontamination assurance sprays," which indicate a presence of contamination, such as by a colorimetric change. However, the conventional decontamination assurance sprays do not decompose the contaminants, nor do the decontamination assurance sprays provide any information on when the contaminant is effectively removed or neutralized without reapplication.

Thus, there remains a need for decontamination assurance sprays that can remove or decompose a contaminant, provide feedback as to removal effectiveness, or, preferably, both.

SUMMARY OF THE INVENTION

The present invention overcomes the foregoing problems and other shortcomings, drawbacks, and challenges of conventional decontamination assurance sprays. While the invention will be described in connection with certain embodiments, it will be understood that the invention is not limited to these embodiments. To the contrary, this invention includes all alternatives, modifications, and equivalents as may be included within the spirit and scope of the present invention.

A method of detecting presence of a chemical warfare agent and includes applying a quinoid form of Rose Bengal to a substrate. When the substrate is exposed to the chemical warfare agent, a lactone form of Rose Bengal is spectrally observed because the presence of the chemical warfare agent converts the quinoid form to the lactone form of Rose Bengal.

In accordance with some aspects of the present invention, a method of determining presence of a chemical warfare agent includes applying a quinoid form of Rose Bengal to a substrate and spectrally observing the applied Rose Bengal. Chemical warfare agent contamination is concluded if the observed spectrum corresponds to a lactone form of Rose Bengal. No chemical warfare agent contamination is concluded if the observed spectrum corresponds to the quinoid form of Rose Bengal.

Other embodiments of the present invention include a method applying a quinoid form of Rose Bengal to a substrate. The substrate is exposed to a nerve chemical warfare agent or a blister chemical warfare agent. A lactone form of Rose Bengal is spectrally observed because presence of the chemical warfare agent converts the quinoid form to the lactone form of Rose Bengal. A fluorescent signature of the exposed substrate is observed.

Additional objects, advantages, and novel features of the invention will be set forth in part in the description which follows and, in part, will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1A:
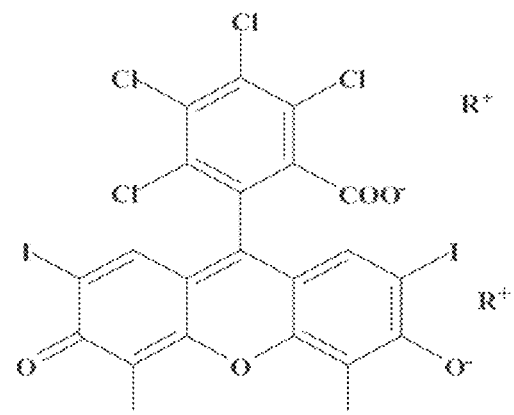
FIGS. 1A and 1B are skeletal formulae of two isomer forms of Rose Bengal, suitable for use with embodiments of the present invention.
Figure 1B:
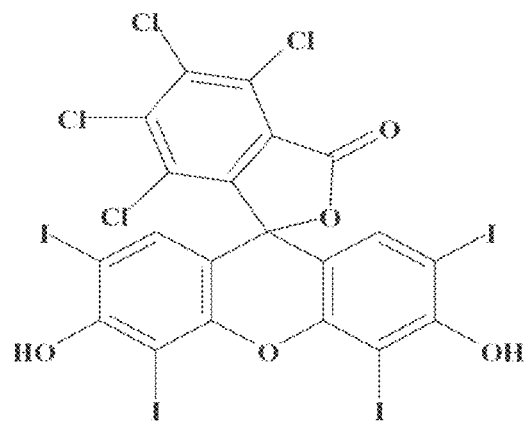

Turning now to the figures, and in particular to FIGS. 1A and 1B, two isomer forms of Rose Bengal ("RB"), a simple fluorescein analog, are shown. RB is generally non-toxic, relatively inexpensive, commercially-available, and FDA approved for, primarily medical, applications. RB further possesses unique chemical properties, described in greater detail below, that neutralize some contaminants, such as chemical warfare agent simulants and pesticides, (collectively referred to as "contaminants") while providing a mechanism (such as absorption/color change and fluorescent emission characteristics) by which the presence of contaminants may be detected and decomposition of the contamination may be monitored. Moreover, RB shows strong dependence of absorption and fluorescence spectra on pH such that spectra intensity decreases with a drop in pH.

RB provides excellent fluorescence and absorbance (colorimetric) response to contaminants and, in the presence of light, effectively and efficiently decomposes the contaminants through a photocatalytic oxidation mechanism. In particular, the RB molecule consists of a benzene moiety, a xanthene moiety, and substituents that determine the photochemical and physical properties. One derivative has the substituent $R=NH(C_2H_5)_3$ attached to a negatively charged oxygen as well as to a carboxylic group to form a salt, which is referred to as a quinoid form ("q") of RB and is shown in FIG. 1A. While not wishing to be bound by theory, when q-RB is exposed to acidic environments, as provided by most contaminants (including, chemical warfare agent simulants, pesticides, and many toxic industrial chemicals), q-RB undergoes a conformational change from the quinoid form to a lactone form ("l"), which is shown in FIG. 1B. When l-RB is exposed to alkaline conditions, the conformational change reverses to q-RB.

The conformational change between the isomer forms of FIGS. 1A and 1B is accompanied by a visual, colorimetric change, wherein l-RB is visually colorless and q-RB is visually perceived as bright pink.

Figure 2:
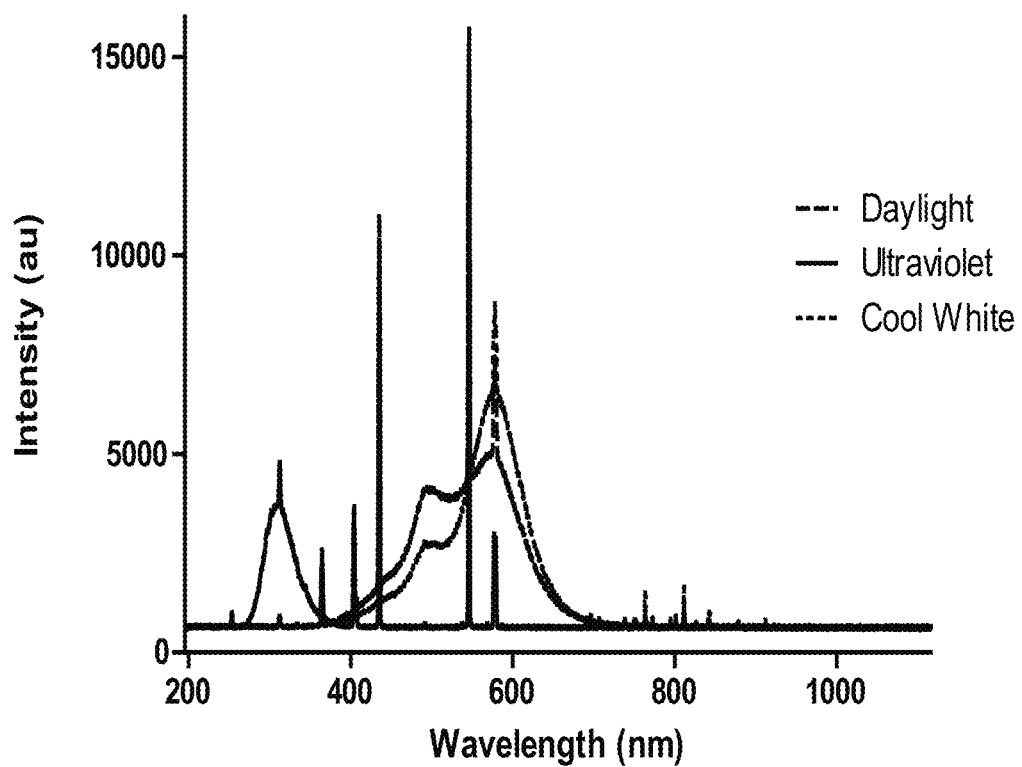
FIG. 2 is the absorption spectrum of Rose Bengal in the presence of daylight (dashed line), ultraviolet radiation (solid line) and cool white light (dotted line).

Both forms of RB are also known photocatalysts and, in the presence of visible light (absorption spectrum is shown in FIG. 2), convert ambient triplet state oxygen to the more active and oxidative singlet state, which is a known decontaminant for a number of contaminants.

Figure 4:
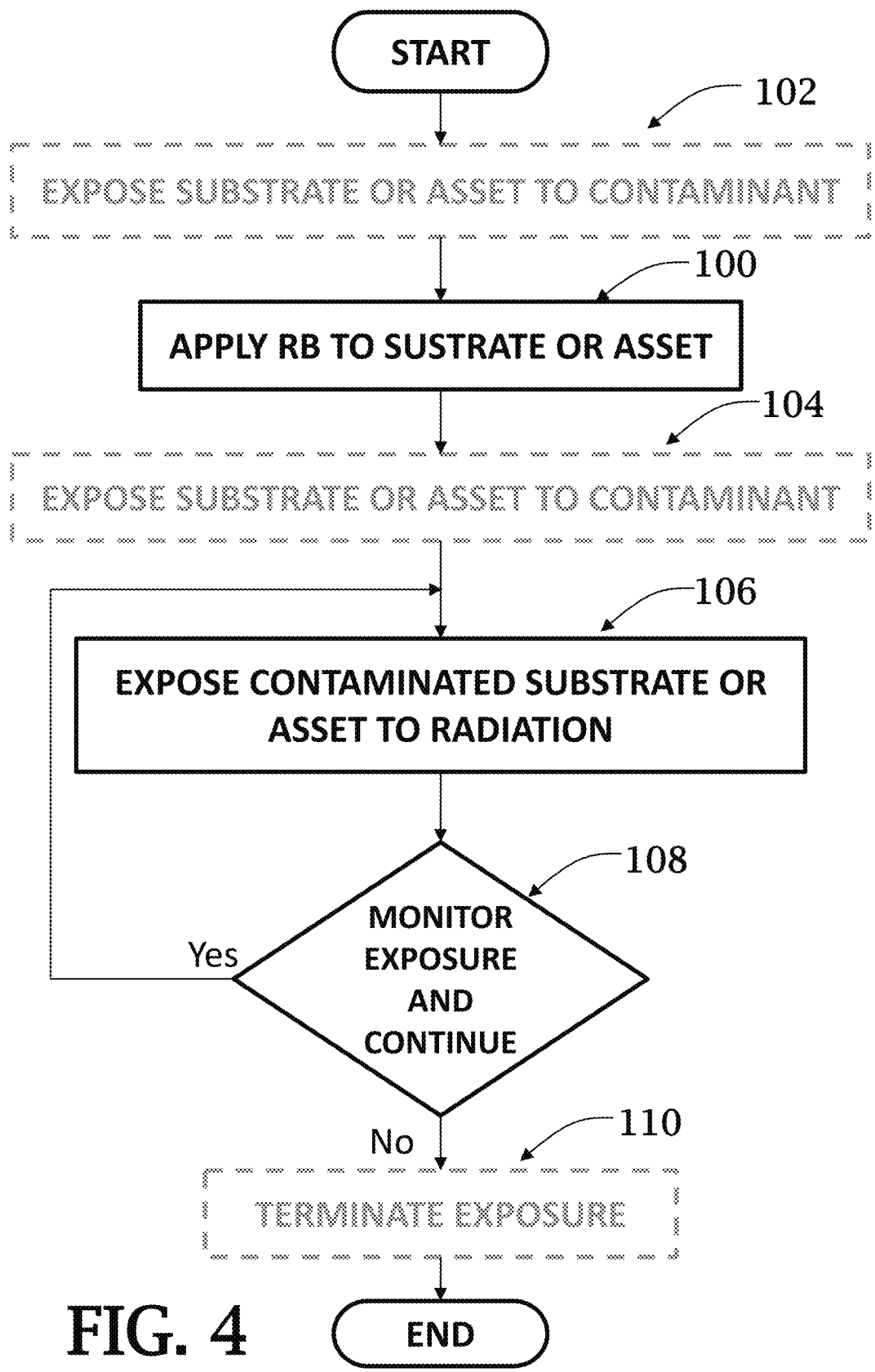
FIG. 4 is a flowchart illustrating a method of using Rose Bengal in accordance with an embodiment of the present invention.

With reference now to FIG. 4, and in use in accordance with an embodiment of the present invention, RB may be applied to a substrate or asset (Block 100) after or before exposing the substrate or asset to at least one contaminant in order to detect the contaminant, and to monitor its decomposition (Blocks 102, 104, respectively). The exposure need not be intentional.

RB may be applied neat, such as an additive to aqueous- or solvent-based systems and for application to contaminated substrate or asset. According to another embodiment, RB may be cross-linked into fabrics, polymers, or coatings at least partially comprising the substrate or asset and via established crosslinking methods for contamination detection and self-decontamination. In still other embodiments, RB may be cross-linked into nanoparticles for industrial or remediation applications. Suitable cross-linking methods and mechanisms are known by the skilled artisan and may include, for example, thermal attachments, microwave attachment, physical adsorption, polymeric attachment, or cross-linking agents (such as acrylates, silanes, epoxides, vinyl groups, and so forth). Cross-linking to nanoparticles may alternatively be accomplished according to the methods taught in U.S. Provisional Application No. 61/829,557, filed May 31, 2013, and entitled CONTROLLED MICROWAVE ASSISTED-SYNTHESIS OF FUNCTIONALIZED SILICA NANOPARTICLES; International Application No. PCT/GB2014/051644, filed May 29, 2014, and entitled CONTROLLED MICROWAVE ASSISTED SYNTHESIS OF FUNCTIONALIZED SILICA NANOPARTICLES; and U.S. Non-Provisional application Ser. No. 14/290,336, filed May 29, 2014, and entitled CONTROLLED MICROWAVE ASSISTED SYNTHESIS OF FUNCTIONALIZED SILICA NANOPARTICLES. The disclosure of each application is incorporated herein by reference, in its entirety. Due to its high solubility in water, RB may alternatively be bind to a porous surface of the nanoparticle though functionalization, encapsulation, or trapping dye molecules. Functionalization or trapping may prevent dilution of dye molecules in water or water-based solutions and subsequent escape of the molecules from the surface upon removal of water.

According to yet other embodiments, RB may be directly integrated into a coating or into fluids to provide chemical warfare agent simulant detection, decontamination, and decontamination assurance sprays.

In Block 106, the contaminated substrate or asset may then be exposed to radiation having a wavelength ranging from 400 nm to 700 nm for detection of at least contaminant. For purposes of decontamination, exposure to light may continue, while monitoring a fluorescent signature, absorbance signature, or both, of the substrate or asset under exposure to radiation ("Yes" branch of Decision Block 108). Otherwise, if monitoring for detection, contamination, or both is complete ("No" branch of Decision Block 108), then exposing the substrate or asset to radiation may be terminated (Block 110) and the process ends.

Use of RB may also include, according to some embodiments of the present invention, additional dyes for additional, enhanced, or alternative detections.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

RB was purchased in its pure form (Pfaltz & Bauer, Waterbury, Conn.) and added in 0.5 wt. %, 1.0 wt. %, 2.0 wt. %, and 5.0 wt. % loadings to commercially-available, MIL-PRF-85285 compliant, aerospace coatings (obtained from PPG Industries, Irvine, Calif.) and tested against chemical warfare agent simulants under simulated light and dark conditions.

Figure 3:
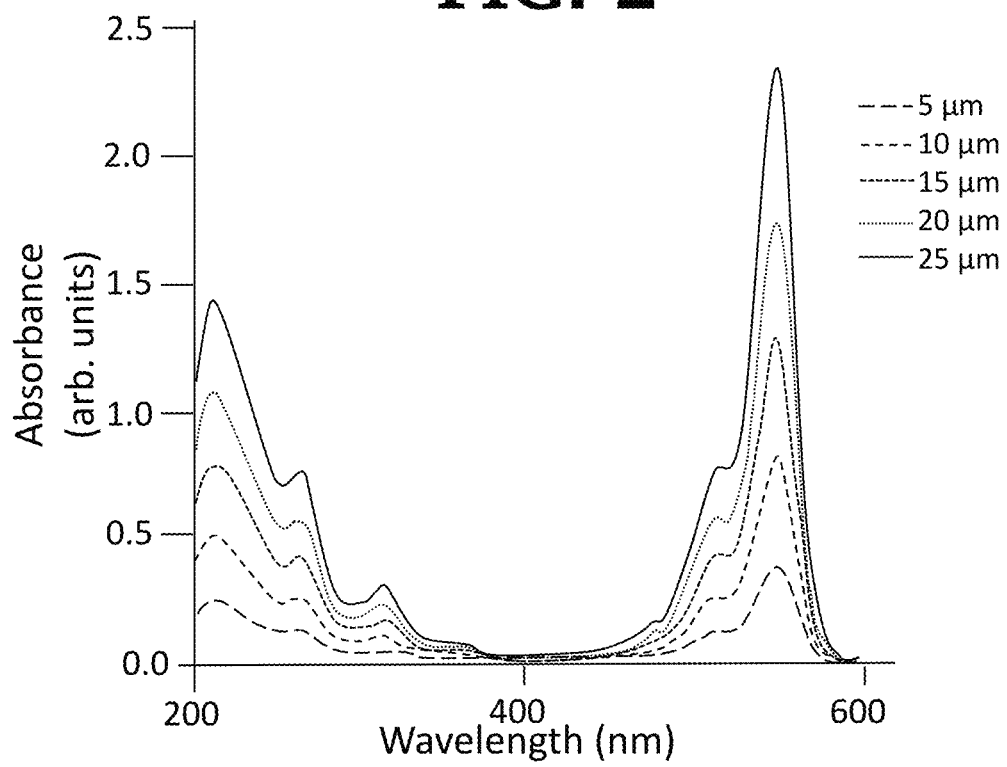
FIG. 3 is the absorption spectrum of Rose Bengal over the visible light spectrum for various concentrations of Rose Bengal (5 μM to 25 μM).
Figure 5:
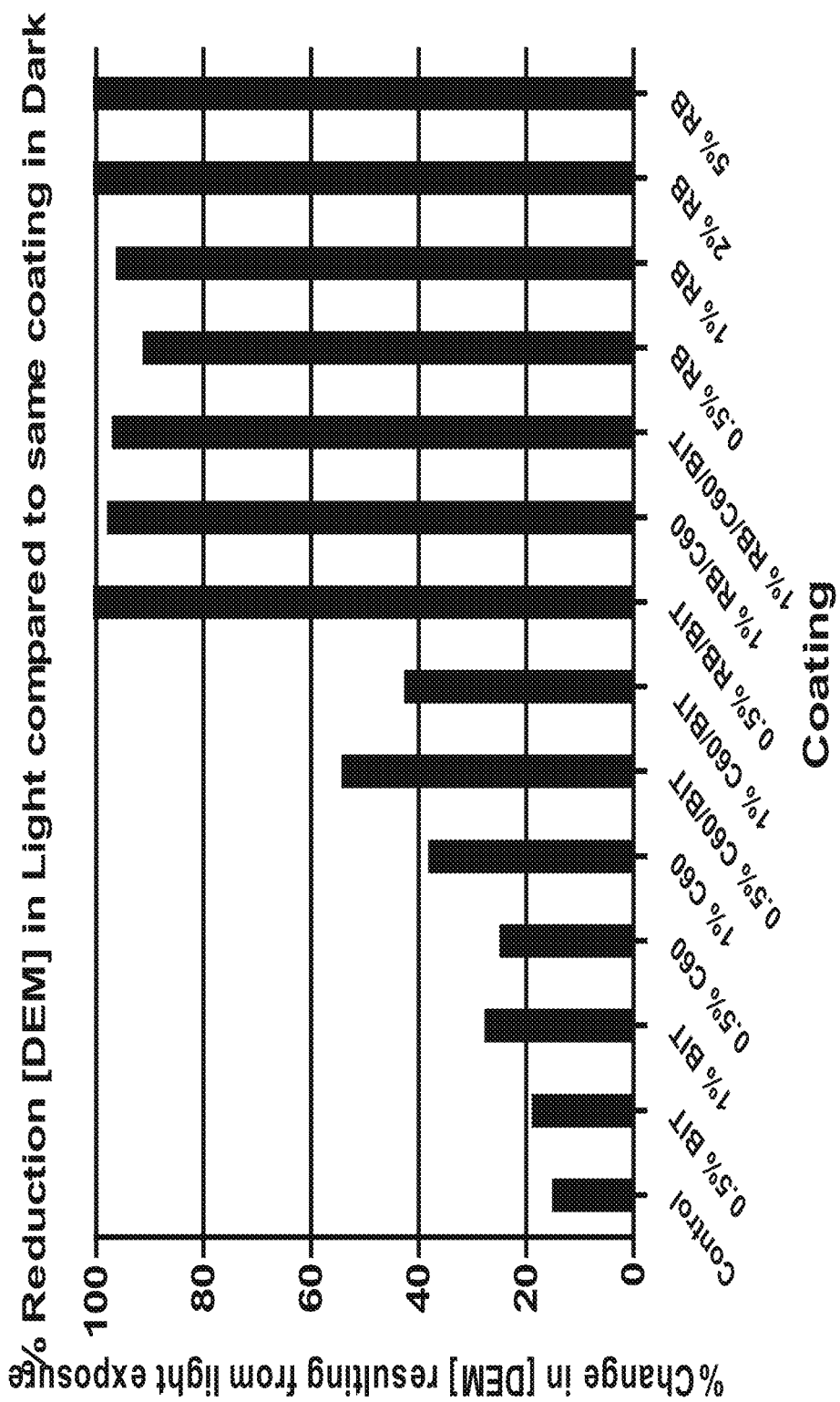
FIG. 5 is a bar graph illustrating a percent change in a concentration of Demeton-S (illustrated as "[DEM]") resulting from light exposure.

As shown in FIG. 3, all compositions containing RB demonstrated high levels of agent and simulant decomposition. In FIG. 5, changes in a percent concentration of DEM resulting from light and dark conditions are shown as bar graphs for each coating tested.

Example 2

The coatings of Example 1 were subjected to 4 $g/m^2$ Demeton-S ("DEM") for 24 hr in complete darkness, simulated indirect sun, and simulated direct sun conditions.

Figure 6:
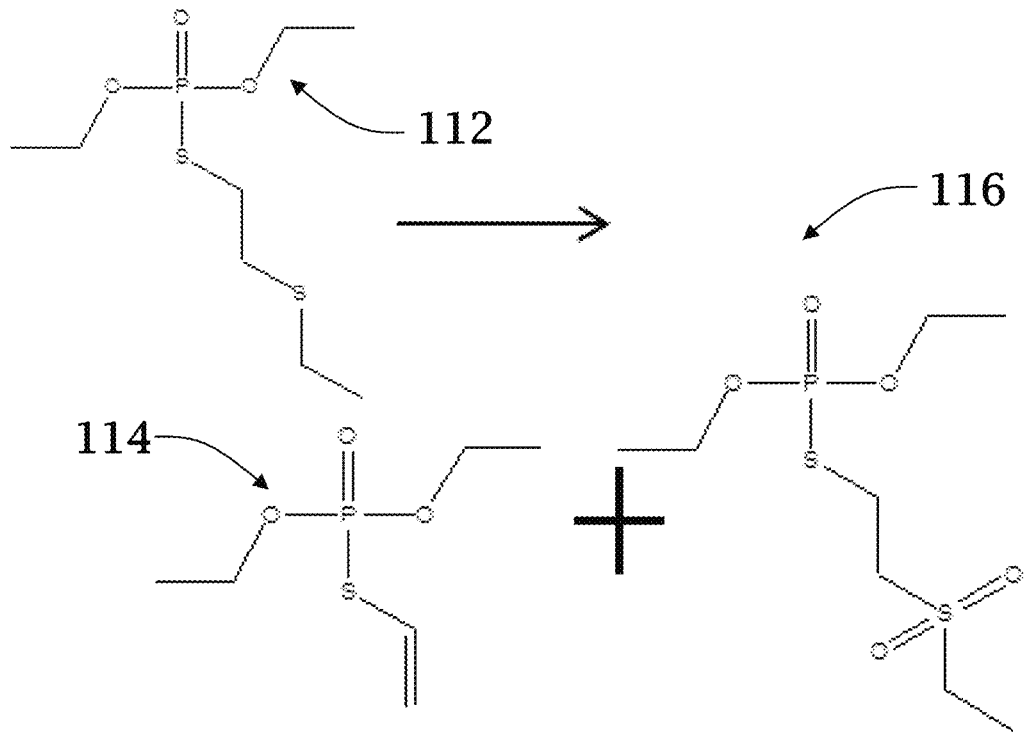
FIG. 6 is a skeletal formula illustrating a mechanism of Rose Bengal photocatalytic oxidation of Demeton-S.
Figure 7A:
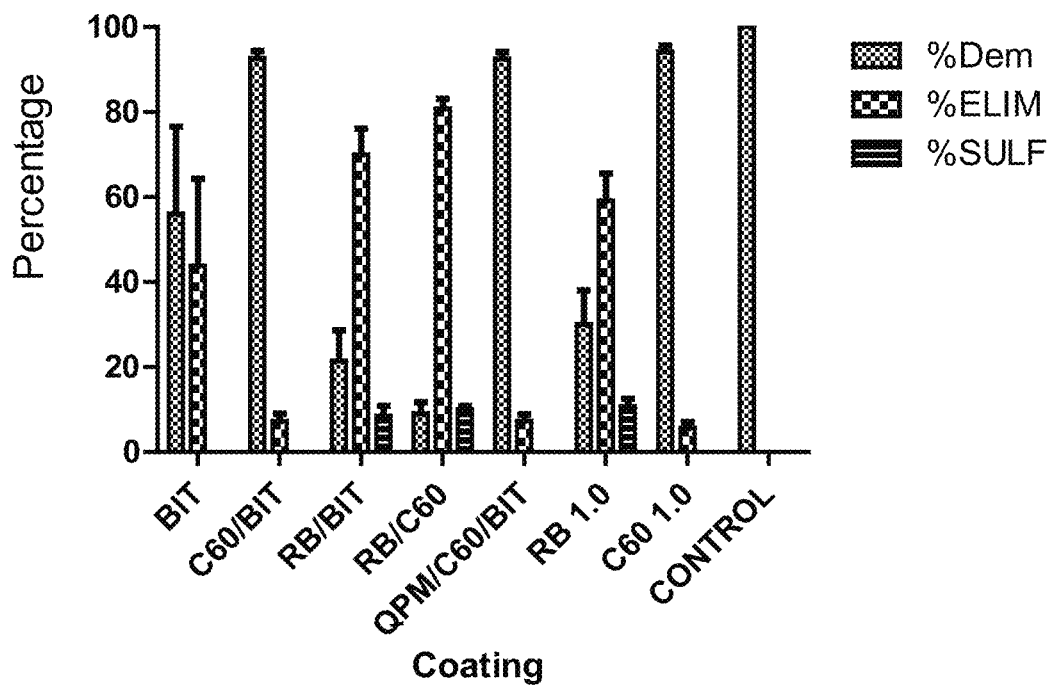
FIGS. 7A-7C are bar graphs illustrating percentage of end products resulting from the Rose-Bengal included photocatalytic oxidation of contaminants at 10,000 LUX, 4,000 LUX, and Dark conditions, respectively.
Figure 7B:
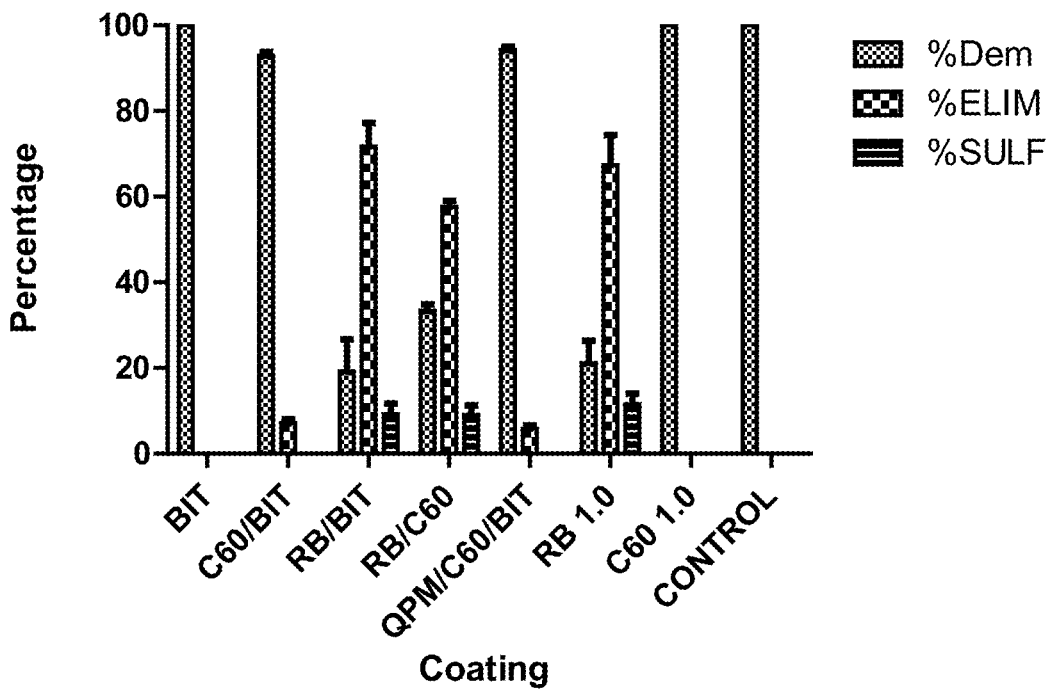
Figure 7C:
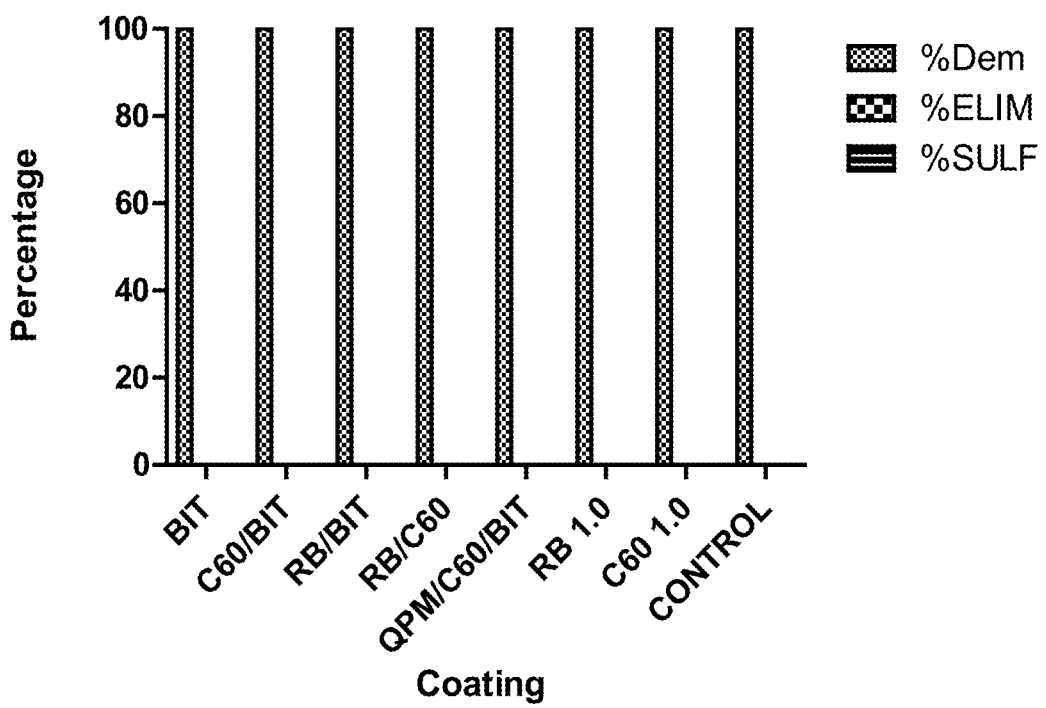

FIG. 6 illustrates a RB-based photocatalytic oxidation mechanism of Demeton-S 112 into an elimination product and while FIGS. 7A-7C are graphical representations of data obtained when coatings having RB as described above and exposed to DEM are irradiated at 10,000 LUX, 4,000 LUX, and Dark conditions, respectively. Each graph illustrates a relative percentage of unreacted Demeton-S ("% DEM"), the elimination product ("% ELIM"), and the neutralized Demeton-S Sulfone ("% SULF").

Figure 8A:
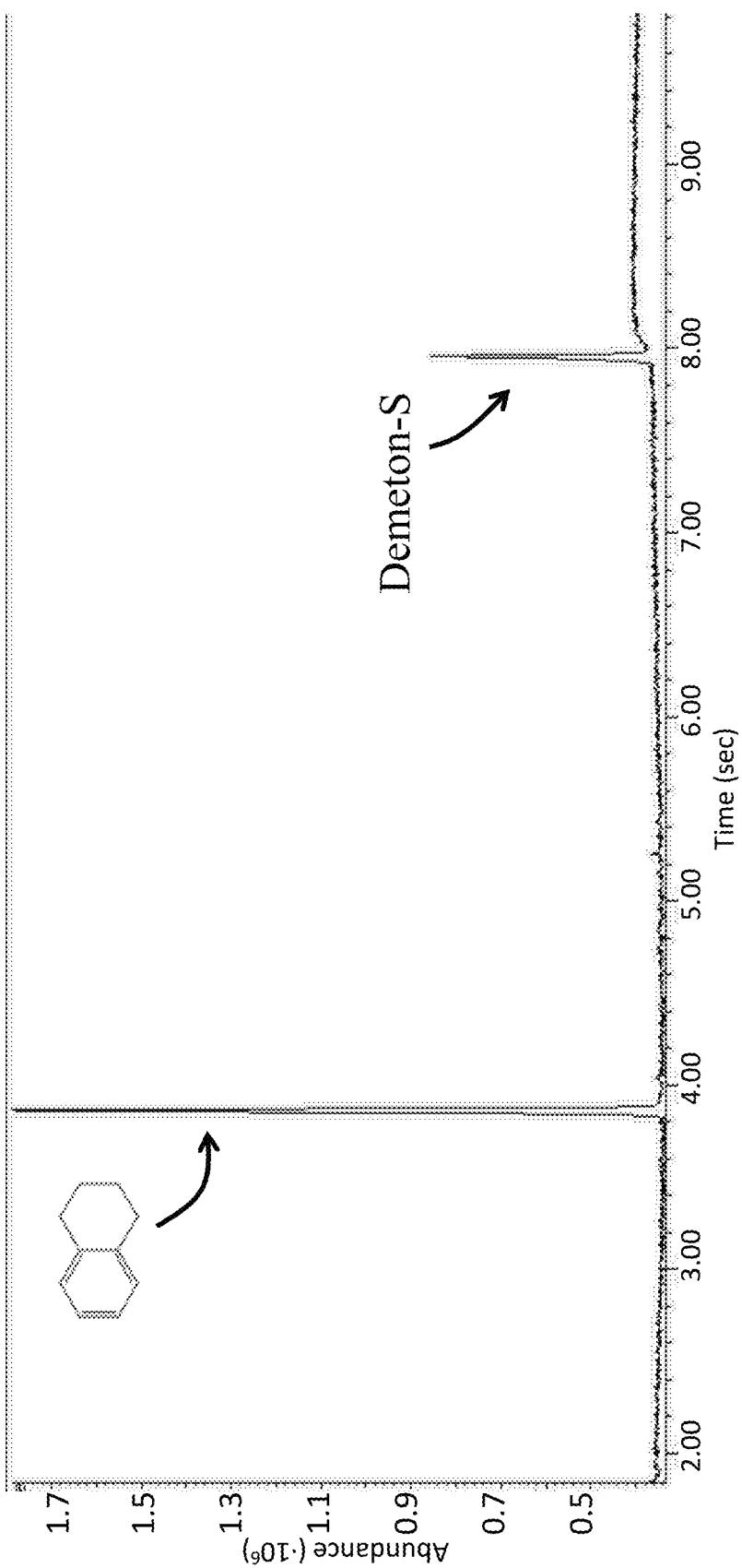
FIGS. 8A-8F are chromatographs of end products of the photocatalytic oxidation of Demeton-S over a 24 hr residence time.
Figure 8B:
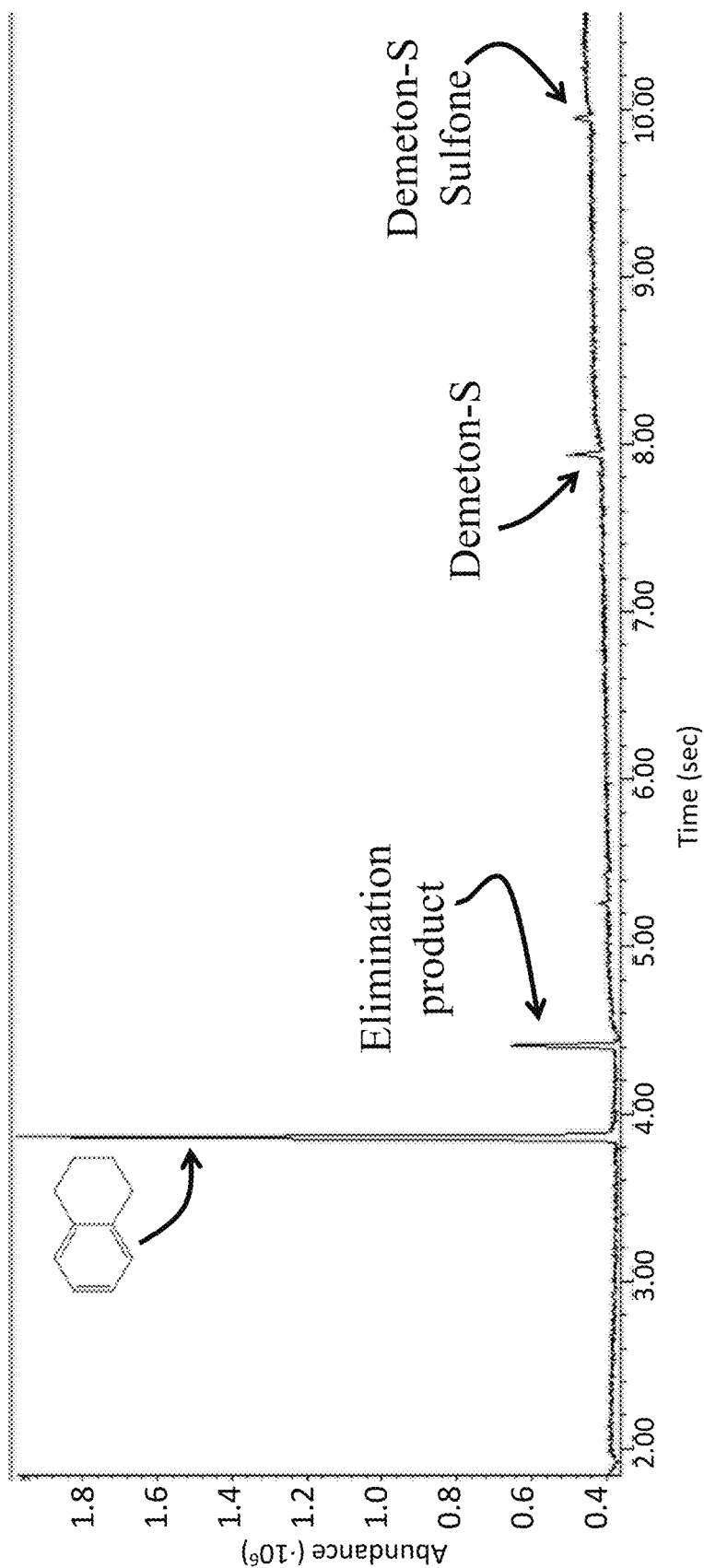

FIGS. 8A-8F are graphical representations of chromatographs of the 24 hr residence time photoactivity versus Demeton-S. The internal standard, tetralin, is the predominate peak appearing at about 3.85 hr. More particularly, FIG. 8A is a graphical representation of the chromatograph of 1.0 wt. % RB photocatalytic oxidation of DEM in MIL-PRF-85285 paint (obtained from PPG Industries) under dark conditions; FIG. 8B a graphical representation of the chromatograph of 1.0 wt. % RB photocatalytic oxidation of DEM in MIL-PRF-85285 under indirect light (4,000 LUX) conditions; and FIG. 8C a graphical representation of the chromatograph of 1.0 wt. % RB photocatalytic oxidation of DEM in MIL-PRF-85285 under direct light (10,000 LUX) conditions.

Figure 8C:
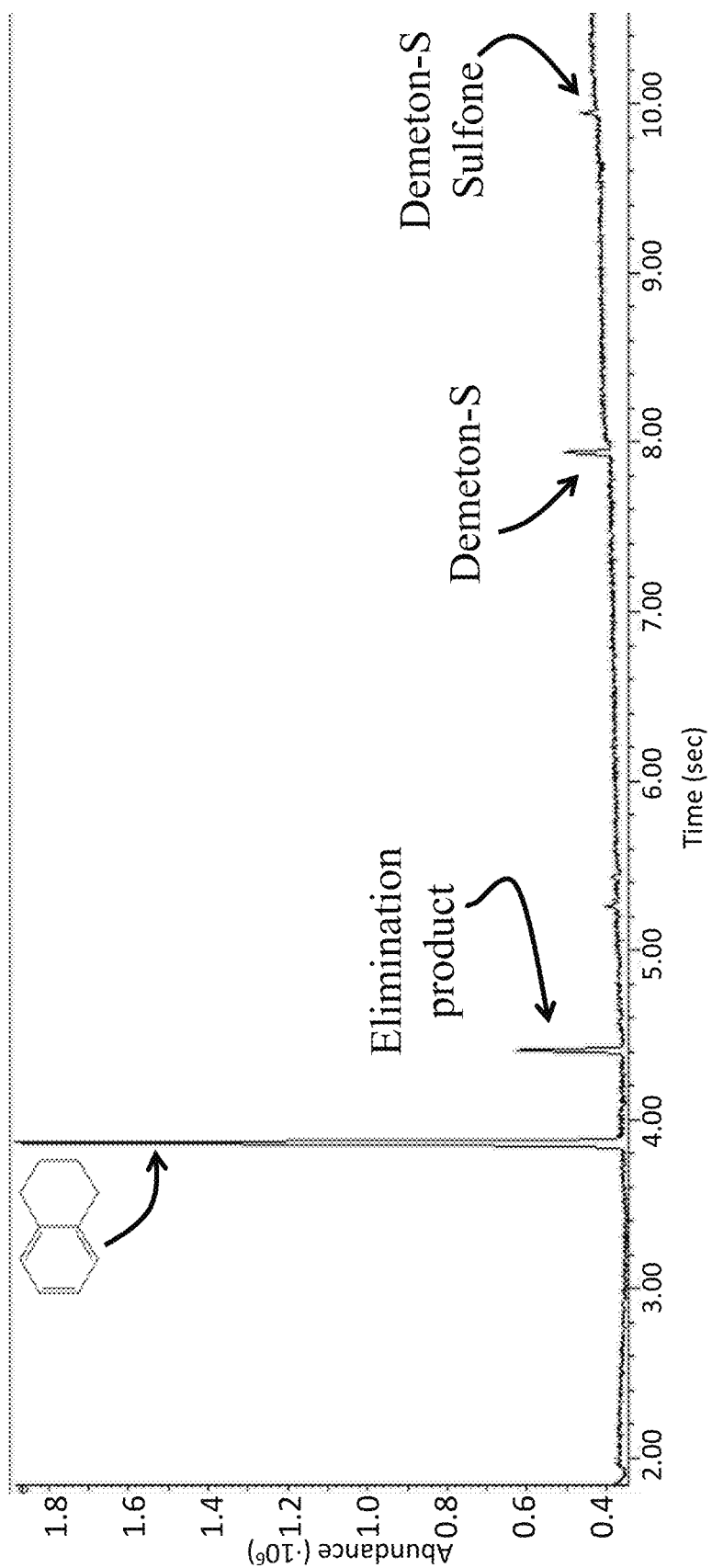
Figure 8D:
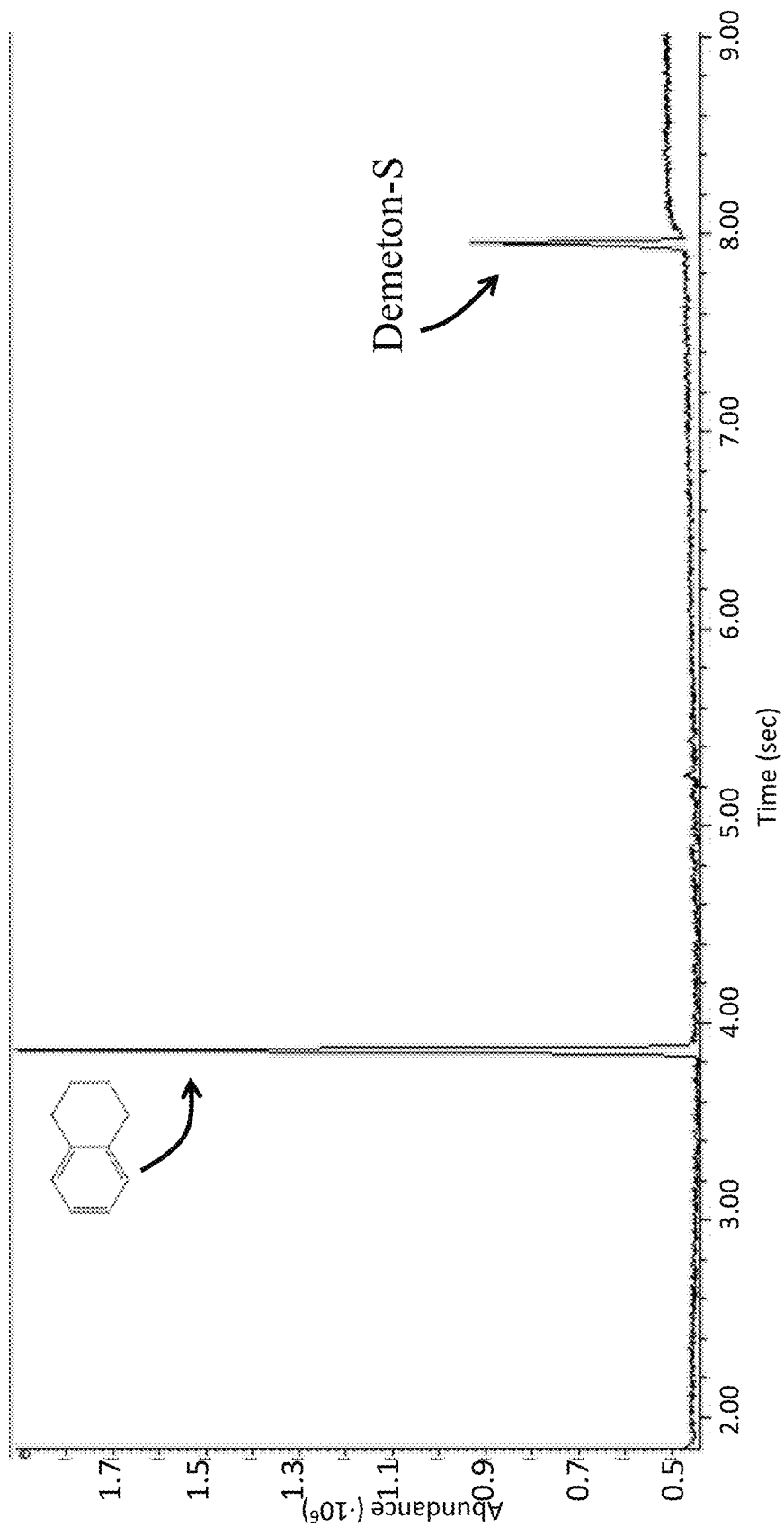
Figure 8E:
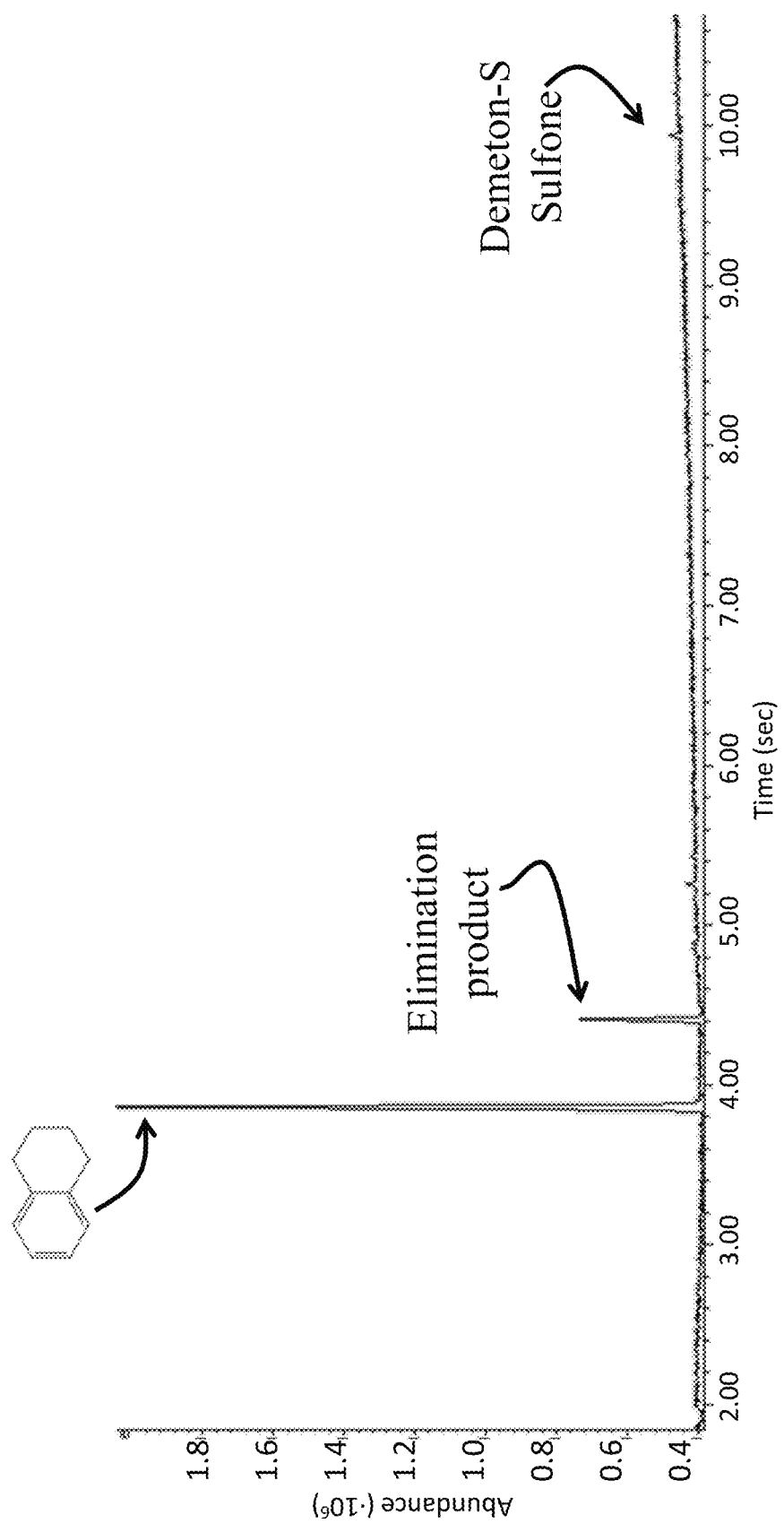
Figure 8F:
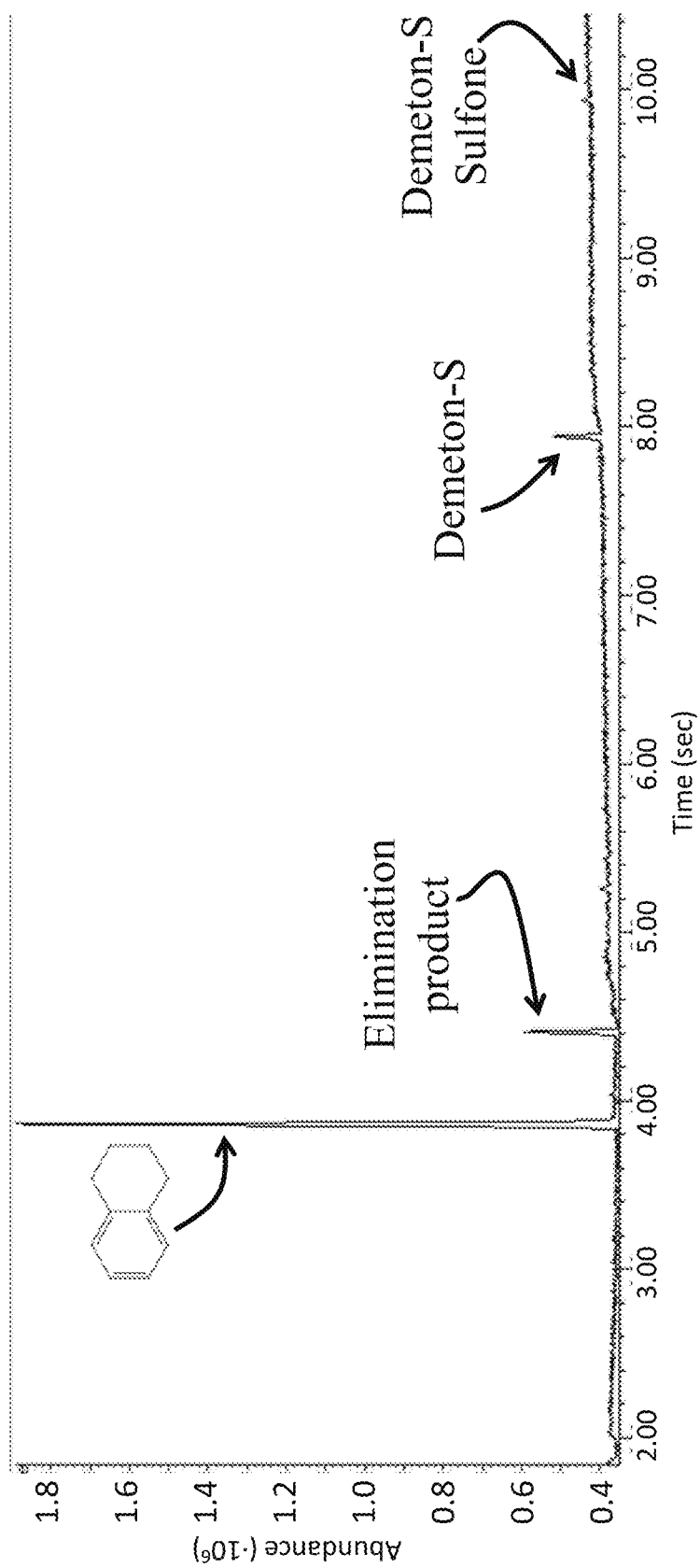

FIGS. 8D-8F are similar to FIGS. 8A-8C, but demonstrate synergistic effects of 0.5 wt. % RB with 0.5 wt. % 1,2-benzisothiaole-3(2H)-one ("BIT").

Example 3

RB was cross-linked into silica nanoparticles fabricated in accordance with the methods described in U.S. Provisional Application No. 61/829,557; International Application No. PCT/GB2014/051644; U.S. Non-Provisional application Ser. No. 14/290,336, which are discussed above. One particular method is described in detail below. Subsequently, the RB-cross-linked silica nanoparticles were cross-linked onto cotton fibers using microwave assisted synthesis methods. RB was also combined with at least one secondary dye, Rhodamine 560 ("R560"), Rhodamine 640 ("R640"), or both, which were also cross-linked into silica nanoparticles and cotton fibers employing similar methods. The silica nanoparticles were tested using absorbance and fluorescent spectra in the presence of each of three chemical agent simulants: Demeton-S, diisopropyl fluorophosphates ("DFP"), and bis(2-chloroethyl) sulfide ("Mustard," or otherwise known to those skilled in the art as "sulfur mustard").

According to one example, 0.7 mL of $H_2O$ is mixed with 1 mL of HCl and 1 mL of tetraethyl orthosilicate ("TEOS"). The solution was mixed for 30 sec. X mg (0.25 mg to 0.75 mg) of R560, 1.00 mg of RB, and Z mg (1.00 mg to 3.00 mg) of R640 were added to 40 mL of acetone and mixed. 0.35 mL of the hydrolyzed TEOS solution were added to the dye solution and mixed for 30 sec. 5 mL of the final solution were placed in a 10 mL CEM vial and subjected to microwave field (300 W) until the surface of the vial has reached 125° C., which was then maintained for 60 sec.

Figure 9:
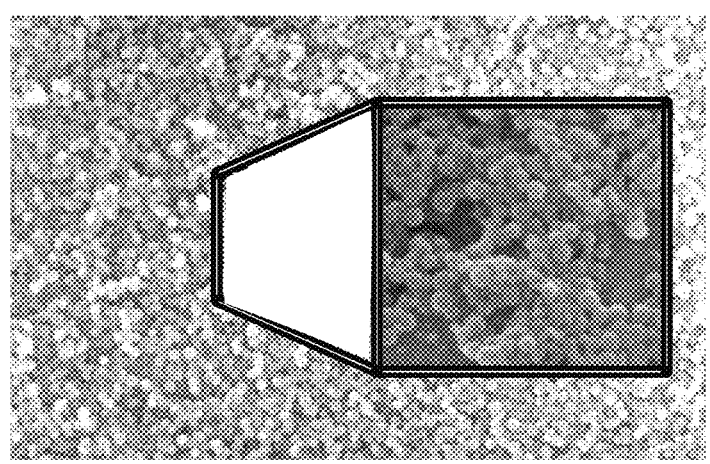
FIG. 9 is an exemplary Scanning Electron Microscopy image of nanoparticles produced in accordance with an embodiment of the present invention.

Diameters of resultant particles ranged from about 200 nm to about 300 nm, as measured by a scanning electron microscope ("SEM") (S-2600N, Hitachi, Ltd., Tokyo, Japan) and dynamic light scattering ("DLS") (Nano-ZS90, Malvern Instruments Ltd., Worcestershire, UK). An exemplary SEM image of the resultant nanoparticles is shown in FIG. 9.

Example 4

A 100 µL suspension of nanoparticles formed according to the method described in Example 3 was injected into each well of a 96-well plate and mixed with 200 µL of water. 1 µL of a contaminant (either Demeton-S or DFP) was carefully placed on top of the suspension surface without mixing. Time dependent spectra were collected using a plate reader (BioTek Synergy™ 4 Hybrid Microplate Reader (BioTek Instruments, Inc., Winooski, Vt.)) using 2 excitation wavelengths: 450 nm and 485 nm. Each run was 50 min long with 10 min time intervals between measurements. Each plot was normalized with respect to a corresponding reference sample.

Figure 10A:
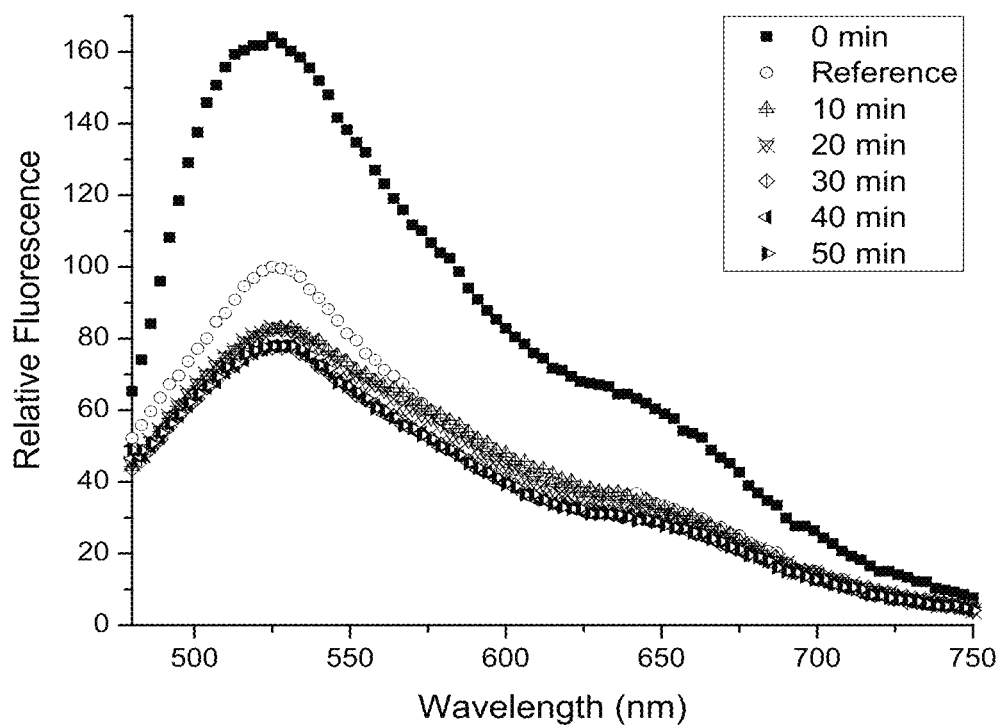
FIGS. 10A-10F are spectra of 0.25 R560+1.00 RB+3.00 R640 nanoparticles exposed to Demeton-S, diisopropyl fluorophosphates, and bis(2-chloroethyl) sulfide for 50 min with data collection every 10 min.
Figure 10B:
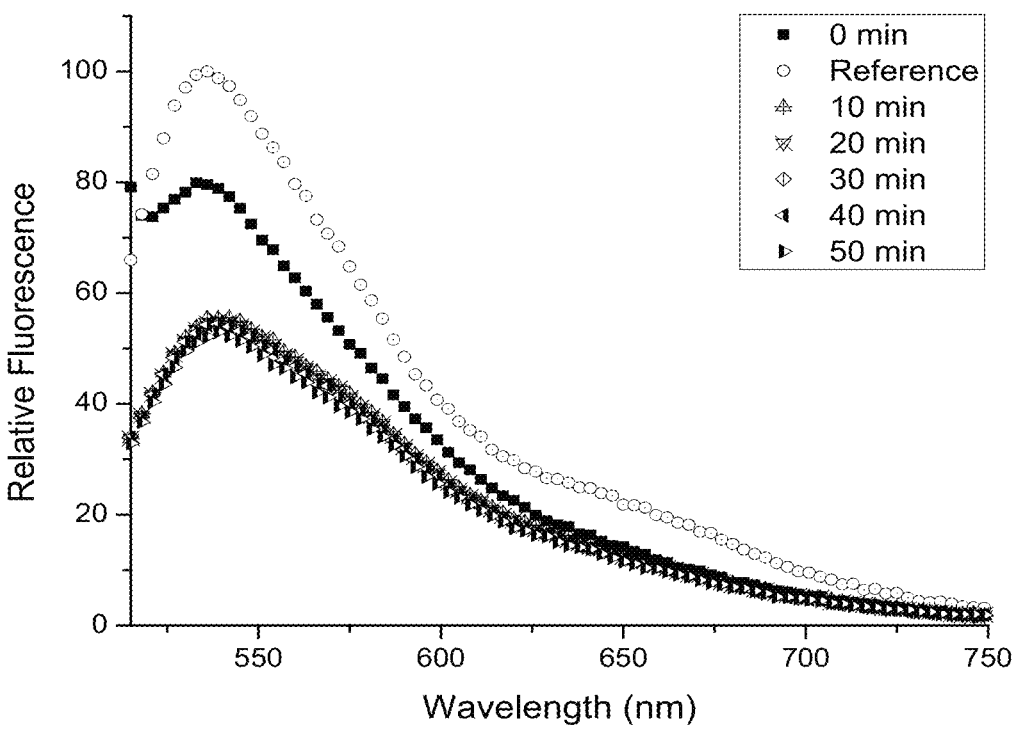
Figure 10C:
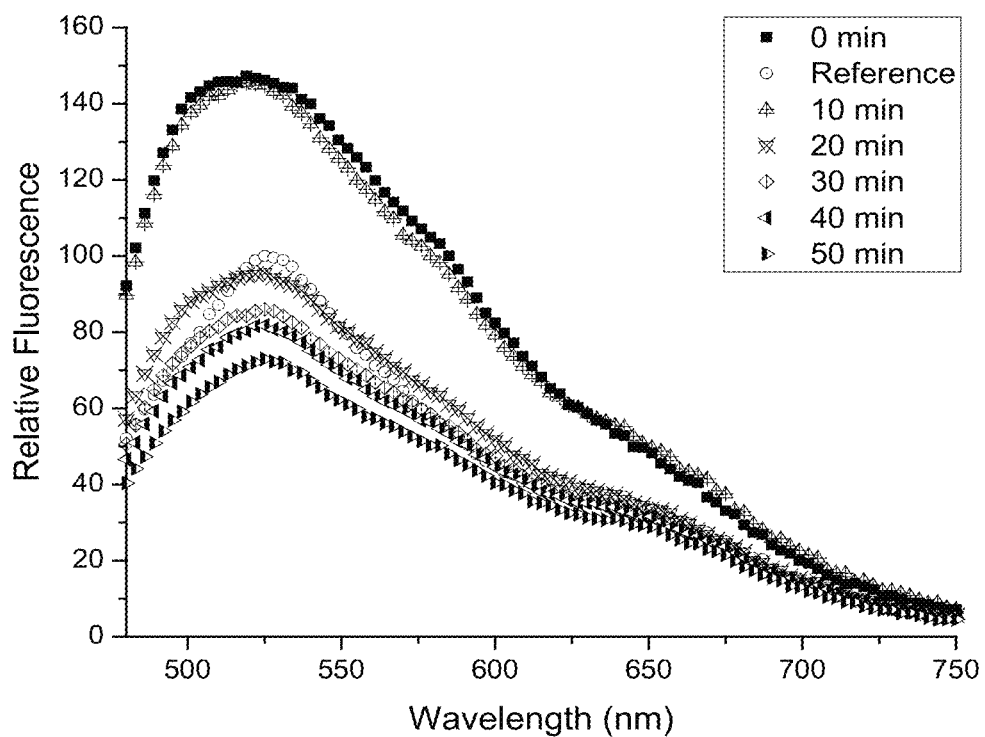
Figure 10D:
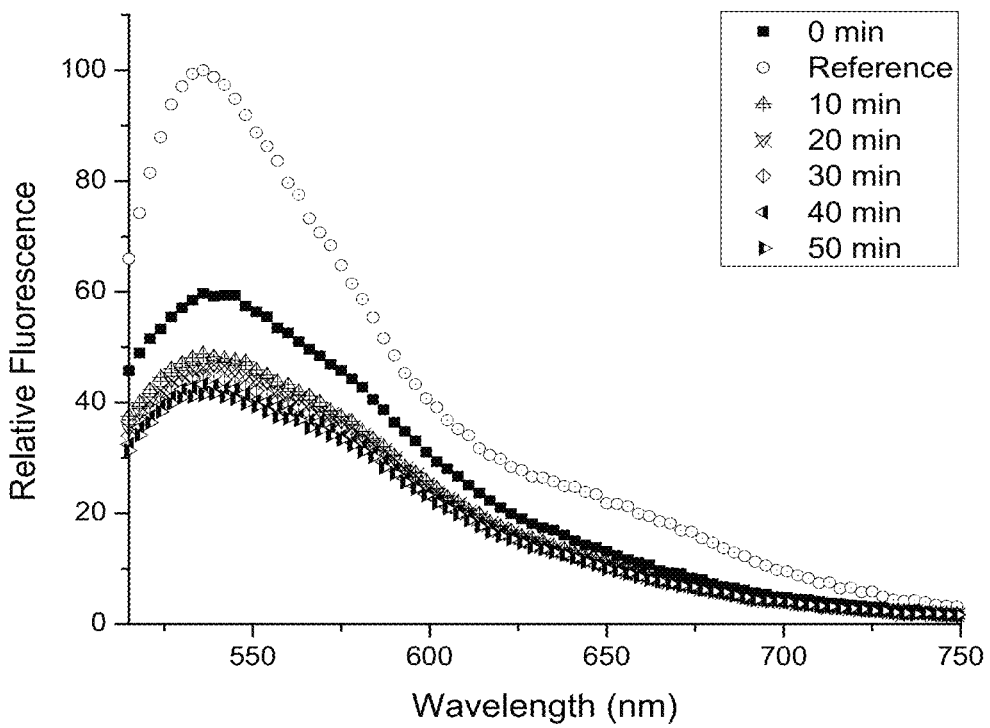
Figure 10E:
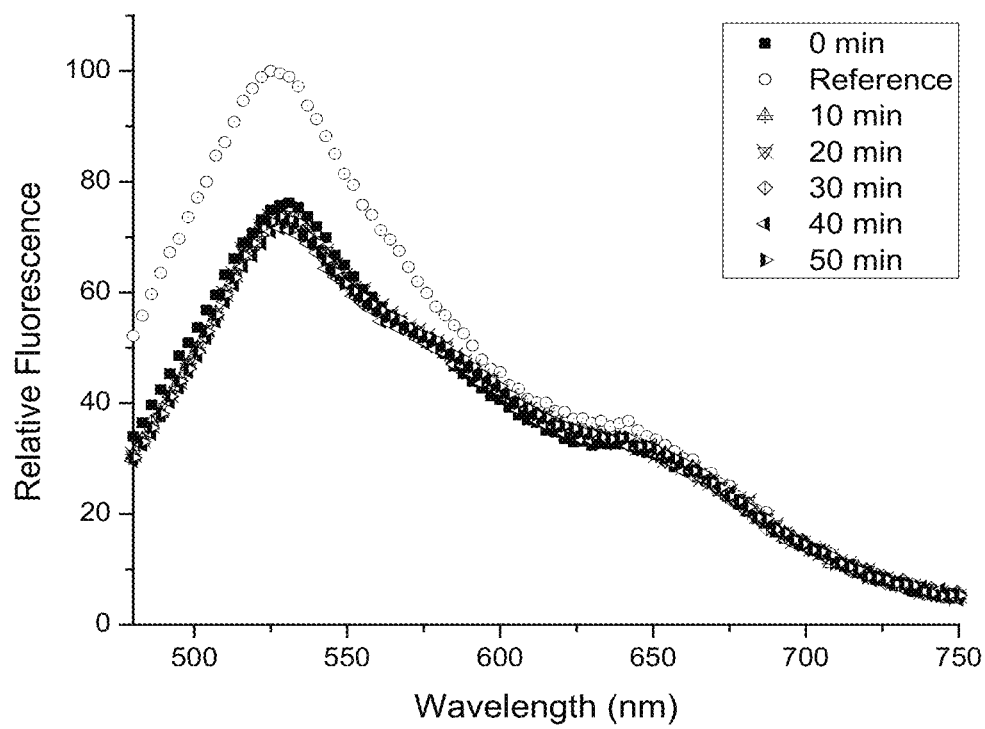
Figure 10F:
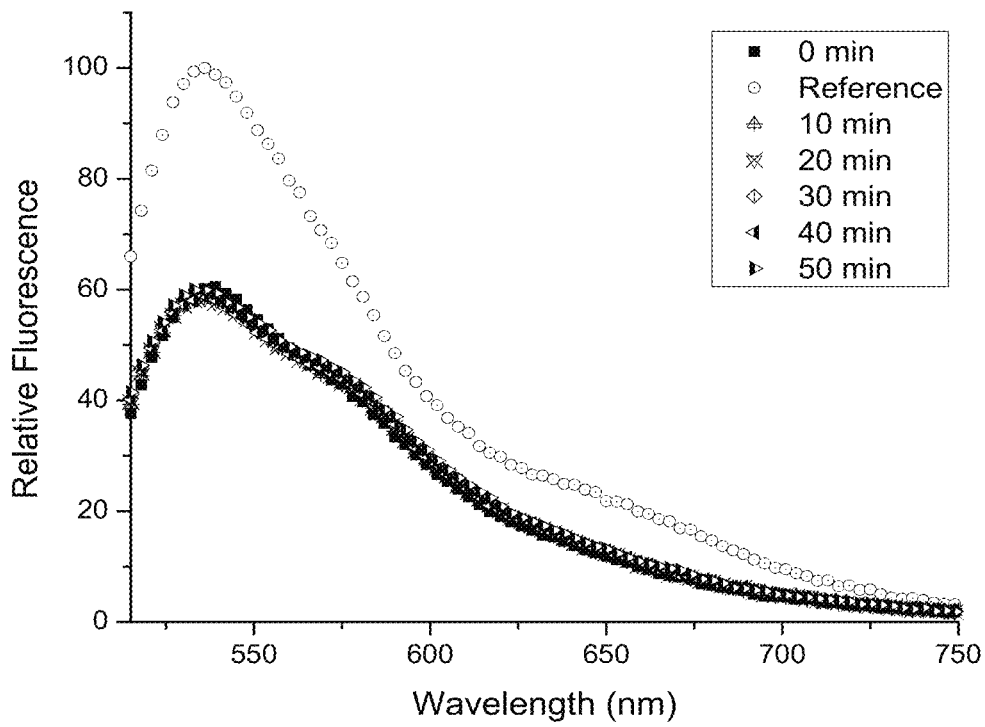

0.25 R560+1.00 RB+3.00 R640: FIGS. 10A-10F are spectra from a sample comprising 0.25 R560+1.00 RB+3.00 R640 nanoparticles and exposed to Demeton-S, DFP, and Mustard for 50 min with data collection every 10 min. FIGS. 10A and 10B illustrate results versus Demeton-S at 450 nm and 485 nm, respectively; FIGS. 10C and 10D illustrate results versus DFP at 450 nm and 485 nm, respectively; and FIGS. 10E and 10F illustrate results versus Mustard at 450 nm and 485 nm, respectively. These data demonstrate that the nanoparticles respond to the presence of simulants for both excitation wavelengths. The spectra produced by excitation at 485 nm shows similar response to each of the three simulants with stabilization time at about 20 min.

Figure 11A:
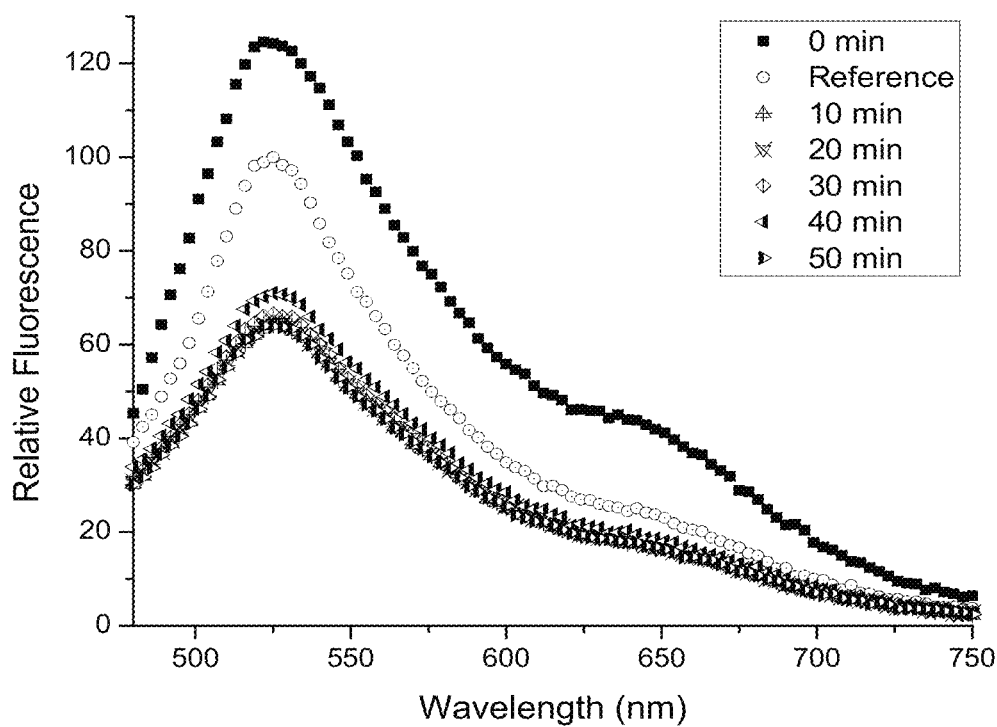
FIGS. 11A-11F are spectra of 0.50 R560+1.00 RB+3.00 R640 nanoparticles exposed to Demeton-S, diisopropyl fluorophosphates, and bis(2-chloroethyl) sulfide for 50 min with data collection every 10 min.
Figure 11B:
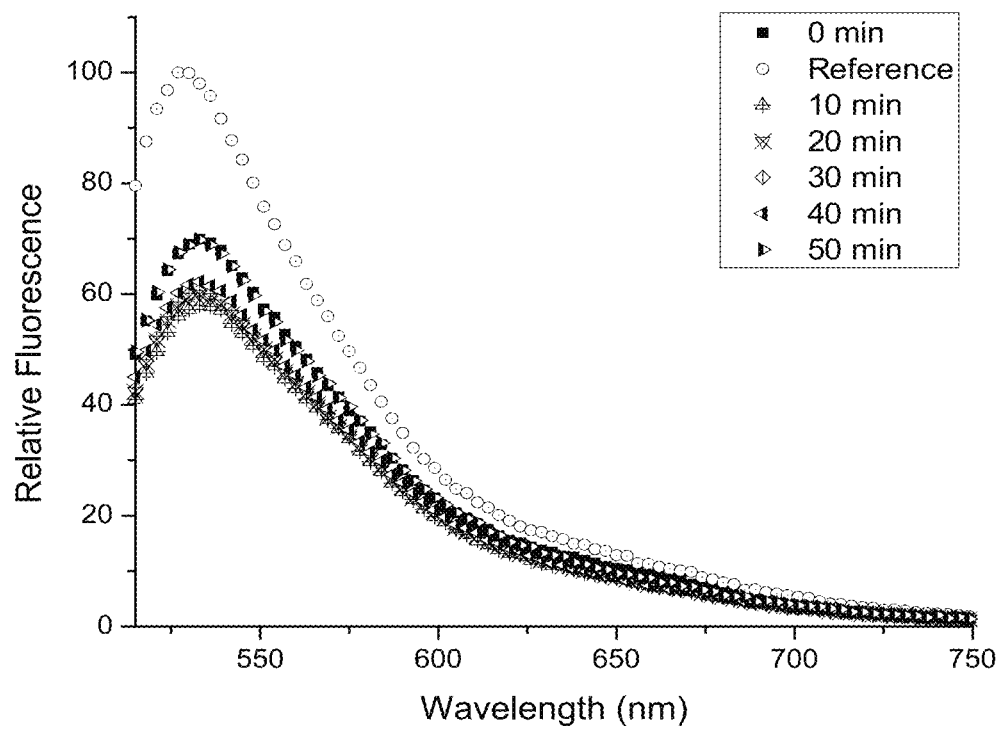
Figure 11C:
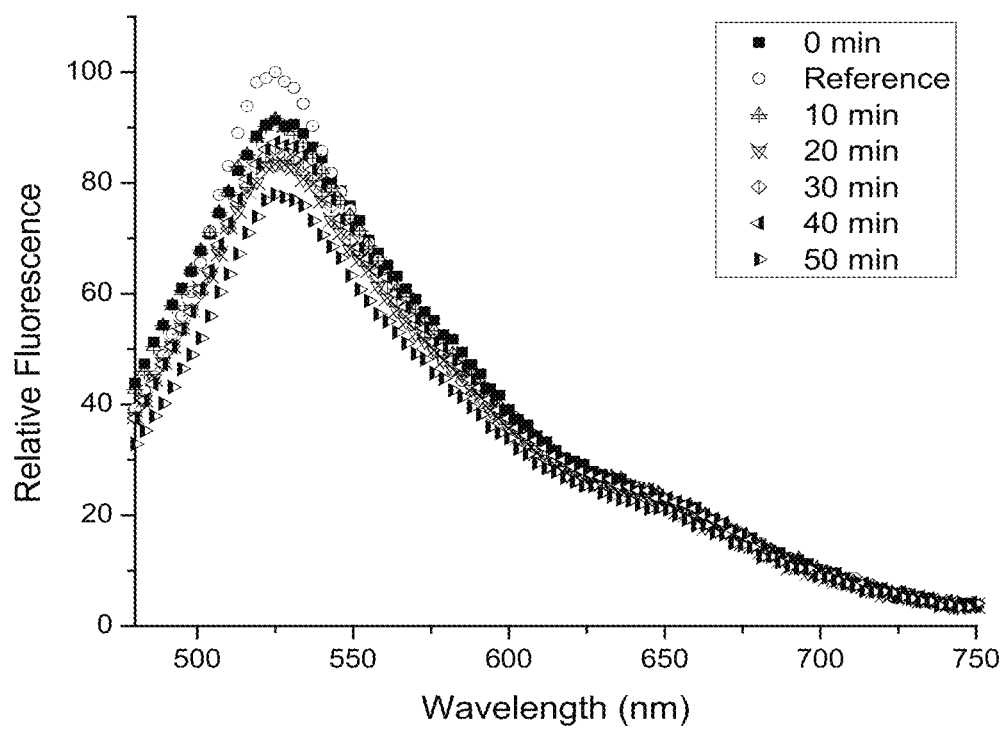
Figure 11D:
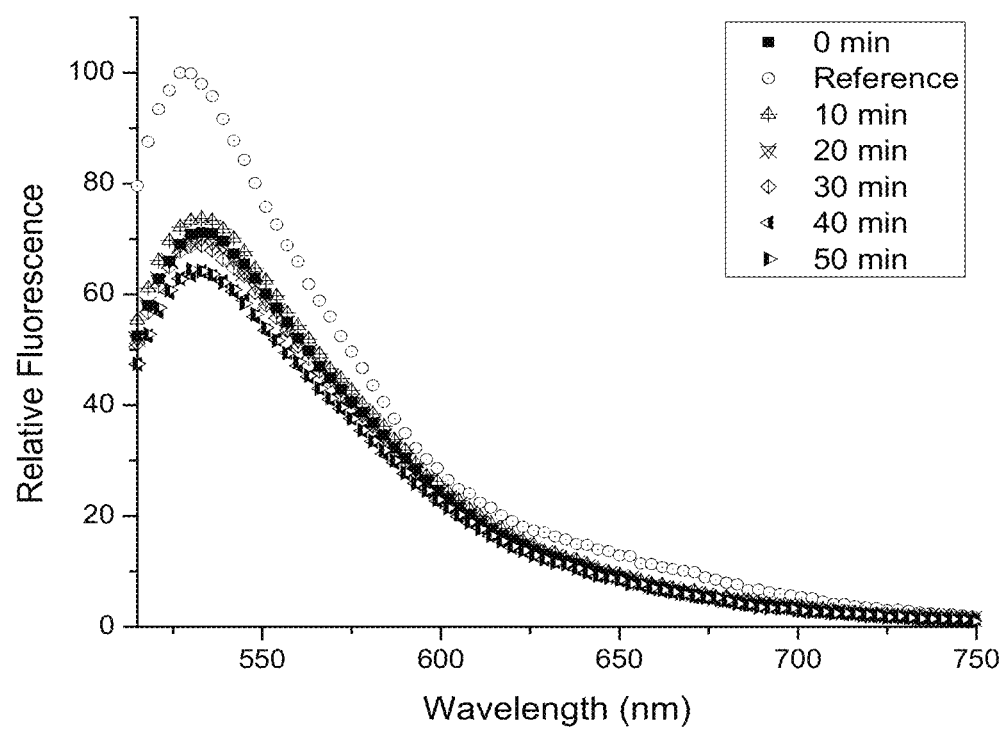
Figure 11E:
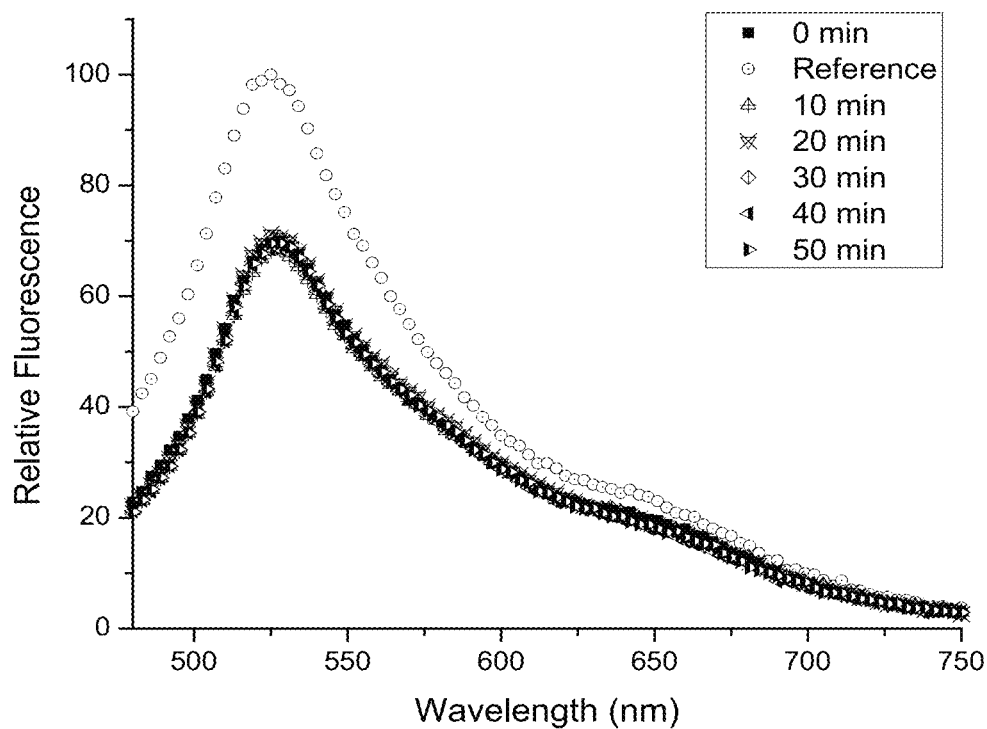
Figure 11F:
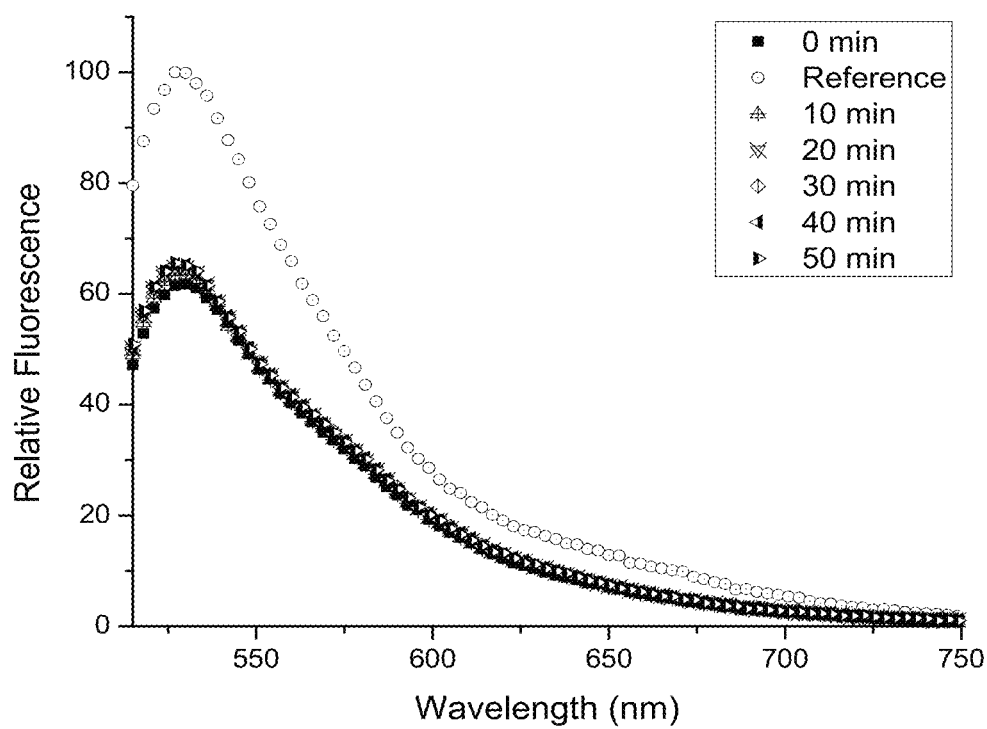

0.50 R560+1.00 RB+3.00 R640: FIGS. 11A-11F are spectra of a sample comprising 0.50 R560+1.00 RB+3.00 R640 nanoparticles and exposed to Demeton-S, DFP, and Mustard for 50 min with data collection every 10 min. FIGS. 11A and 11B illustrate results versus Demeton-S at 450 nm and 485 nm, respectively; FIGS. 11C and 11D illustrate results versus DFP at 450 nm and 485 nm, respectively; and FIGS. 11E and 11F illustrate results versus Mustard at 450 nm and 485 nm, respectively. The 0.50 R560+RB+3 R640 nanoparticles show responses (FIGS. 11A-11F) similar the responses of the 0.25 R560+1.00 RB+3.00 R640 nanoparticles (FIG. 10A-10F); however, the change in fluorescent spectra is not as dramatic exhibiting equilibration time closer to 10 min rather than 20 min as in the case of the 0.25 R560+1.00 RB+3.00 R640 nanoparticles.

Figure 12A:
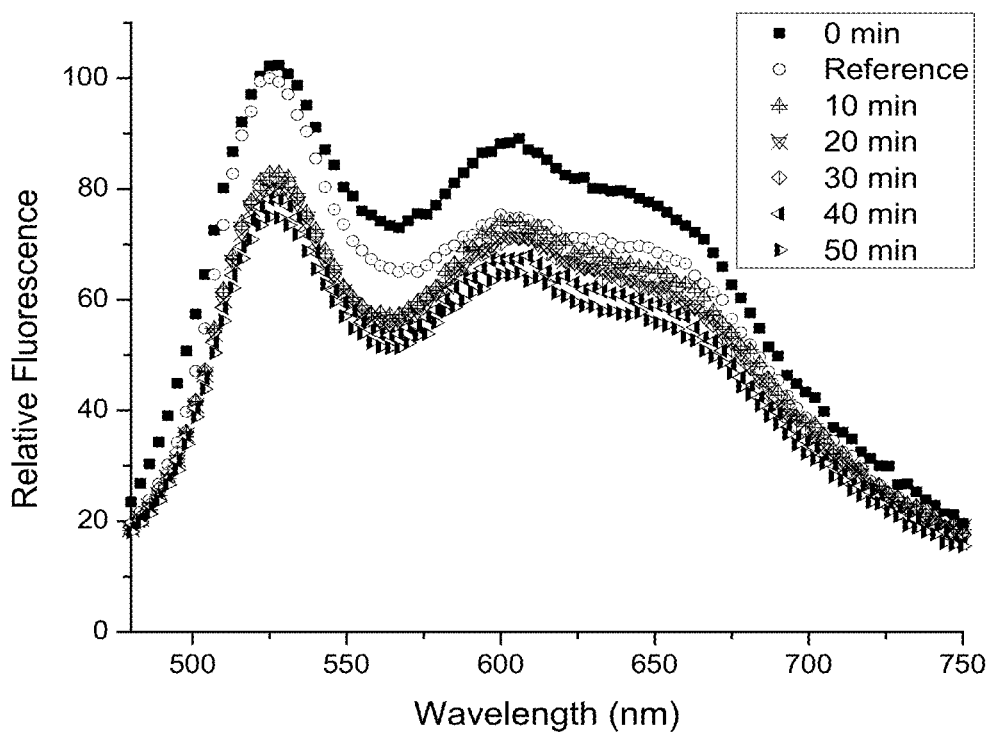
FIGS. 12A-12F are spectra of 0.75 R560+1.00 RB+3.00 R640 nanoparticles exposed to Demeton-S, diisopropyl fluorophosphates, and bis(2-chloroethyl) sulfide for 50 min with data collection every 10 min.
Figure 12B:
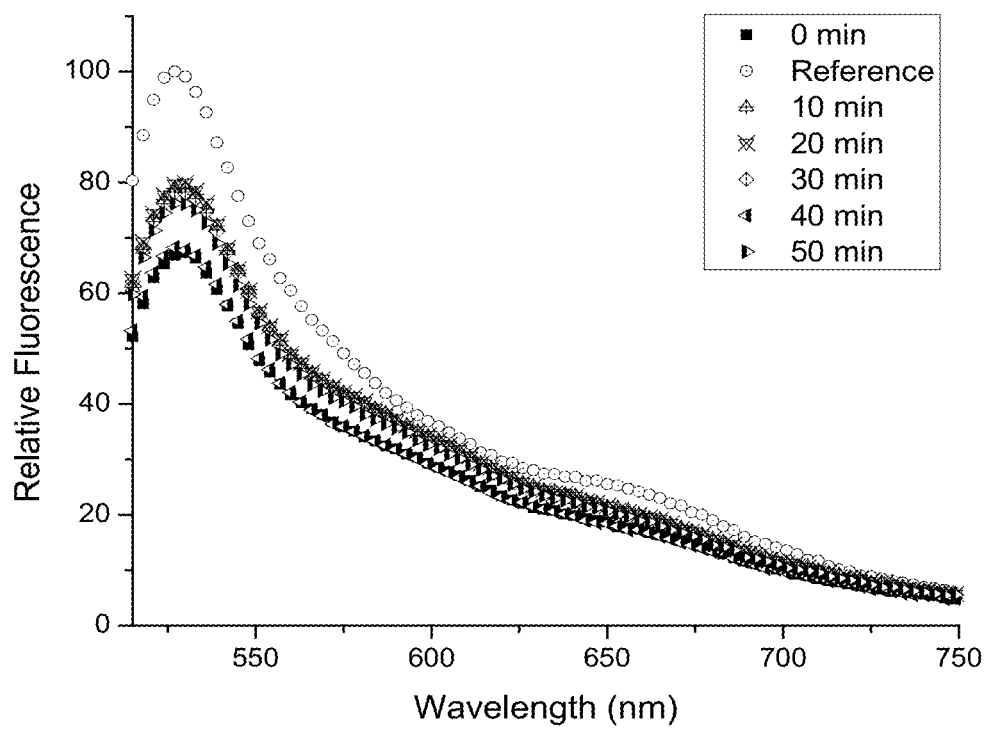
Figure 12C:
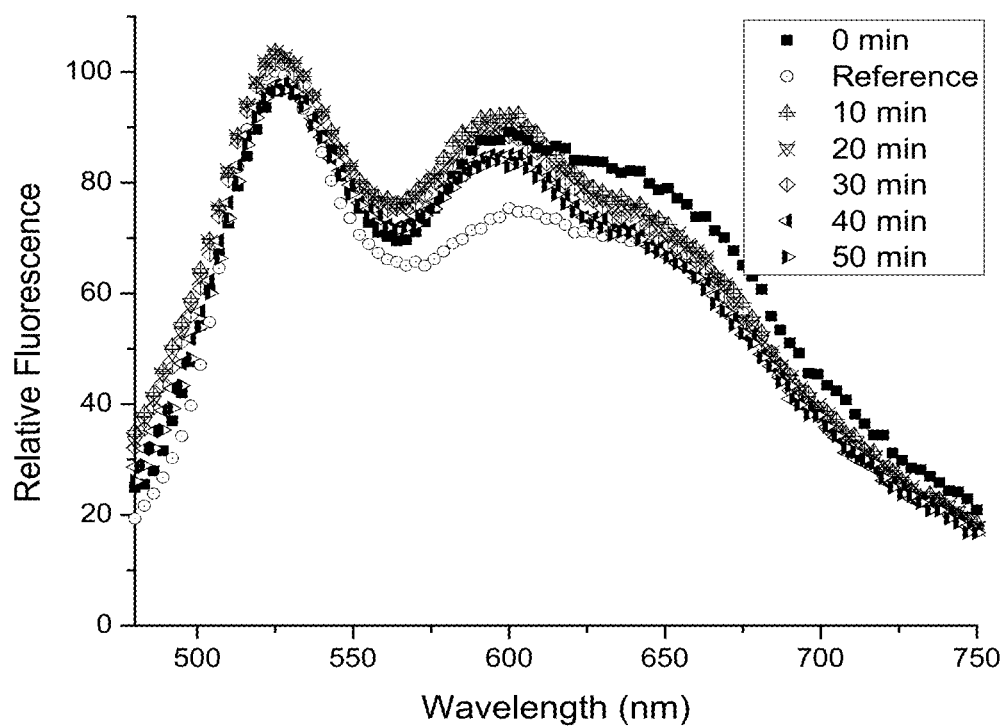
Figure 12D:
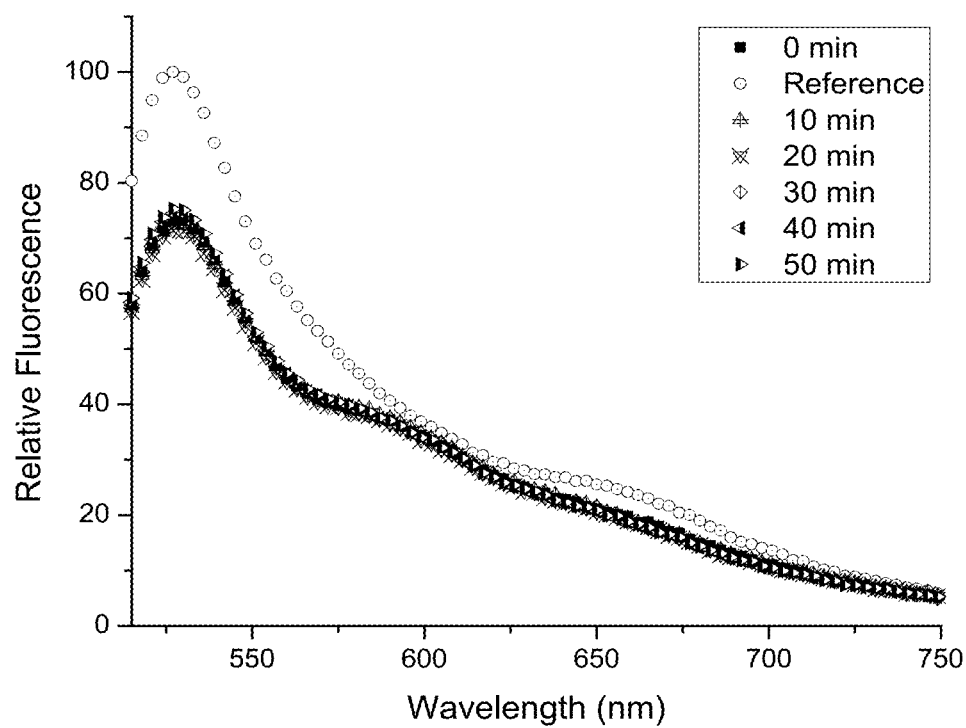
Figure 12E:
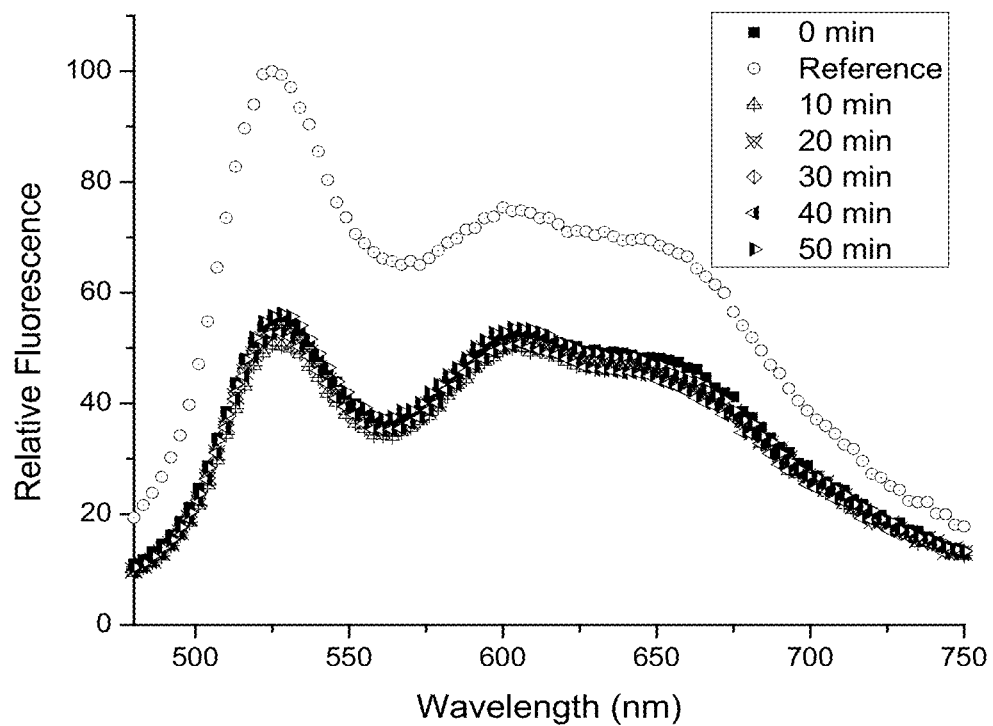
Figure 12F:
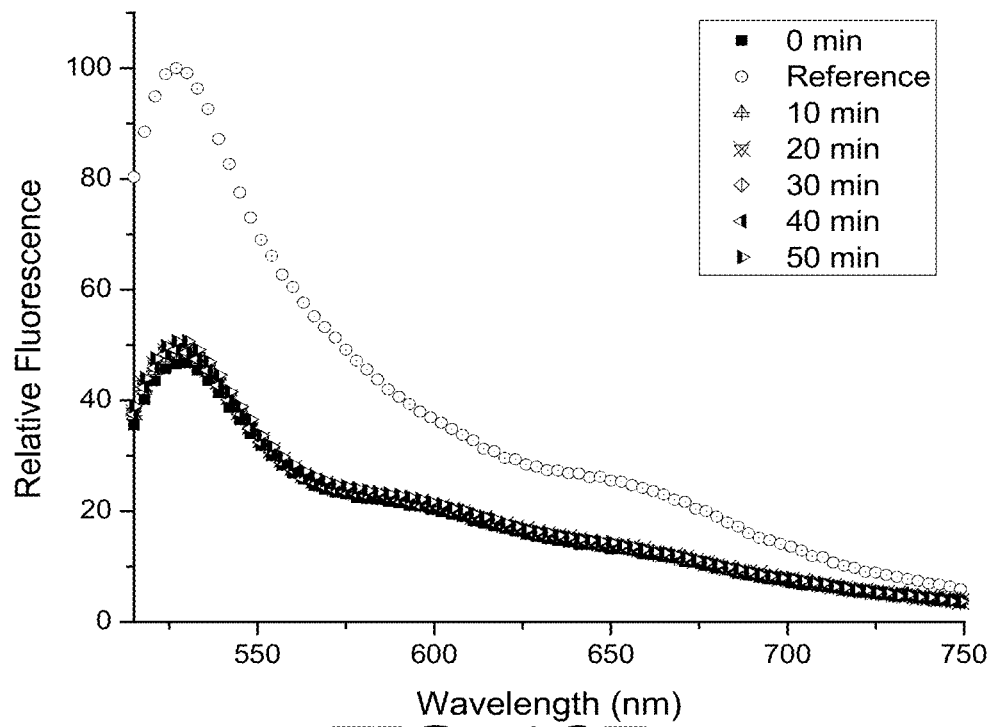

0.75 R560+1.00 RB+3.00 R640: FIGS. 12A-12F are spectra of a sample comprising 0.75 R560+1.00 RB+3.00 R640 nanoparticles and exposed to Demeton-S, DFP, and Mustard for 50 min with data collection every 10 min. FIGS. 12A and 12B illustrate results versus Demeton-S at 450 nm and 485 nm, respectively; FIGS. 12C and 12D illustrate results versus DFP at 450 nm and 485 nm, respectively; and FIGS. 12E and 12F illustrate results versus Mustard at 450 nm and 485 nm, respectively. The 0.75 R560+1.00 RB+3.00 R640 nanoparticles show even less dramatic change in fluorescence spectra with exception of Mustard. The 0.75 R560+1.00 RB+3.00 R640 nanoparticles response time was under 10 min with dramatic change in intensity of the spectra.

Figure 13A:
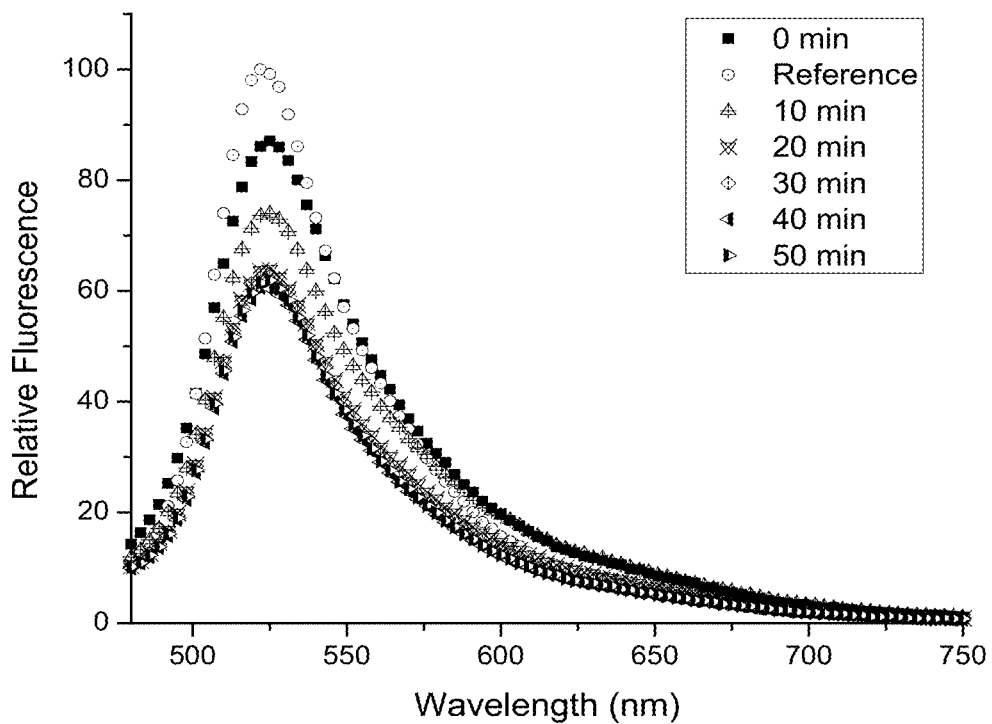
FIGS. 13A-13F are spectra of 1.00 R560+1.00 RB+1.00 R640 nanoparticles exposed to Demeton-S, DFP and Mustard for 50 min with data collection every 10 min.
Figure 13B:
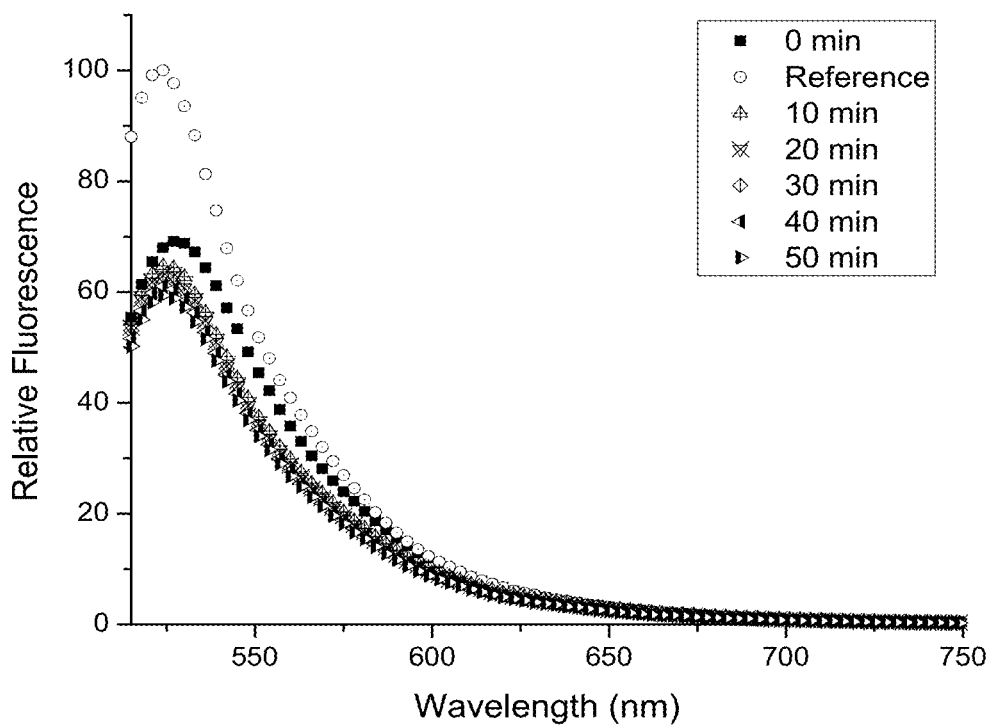
Figure 13C:
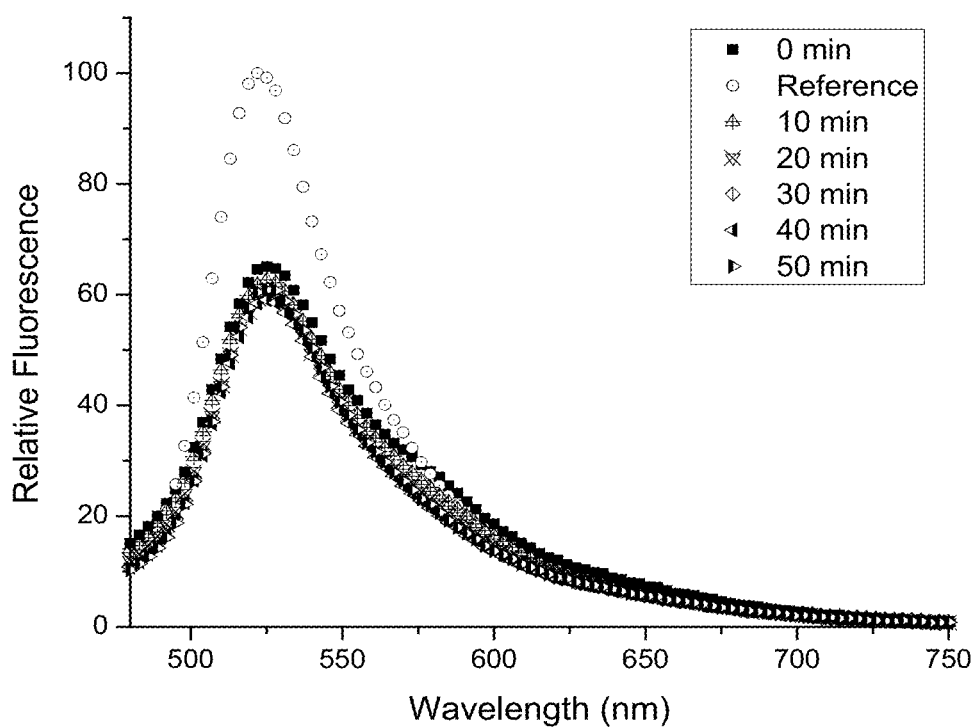
Figure 13D:
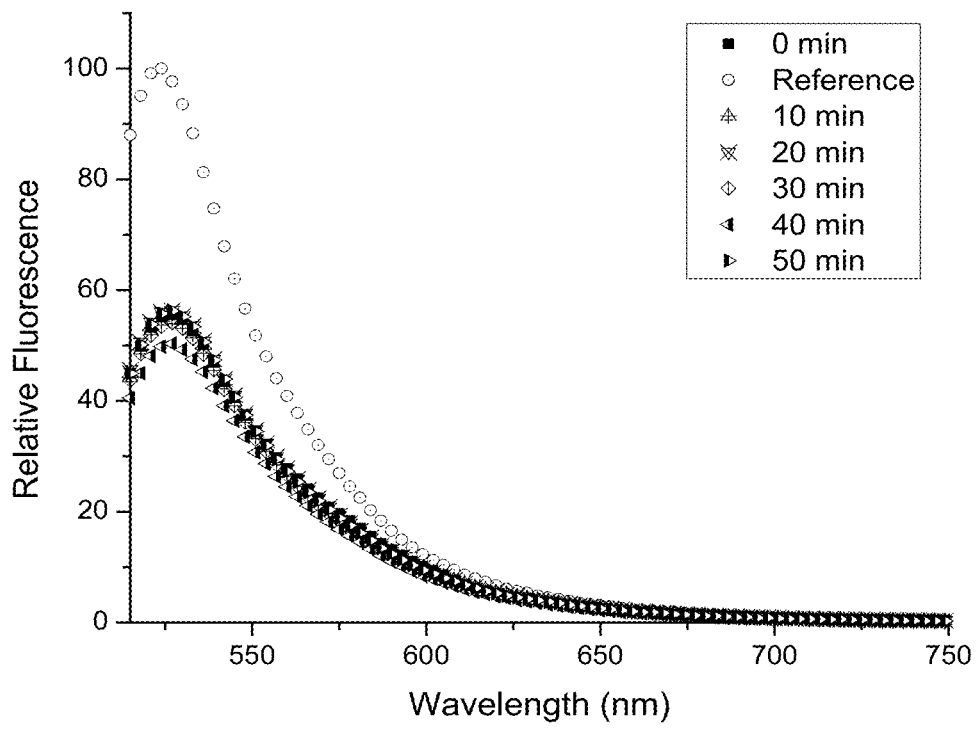
Figure 13E:
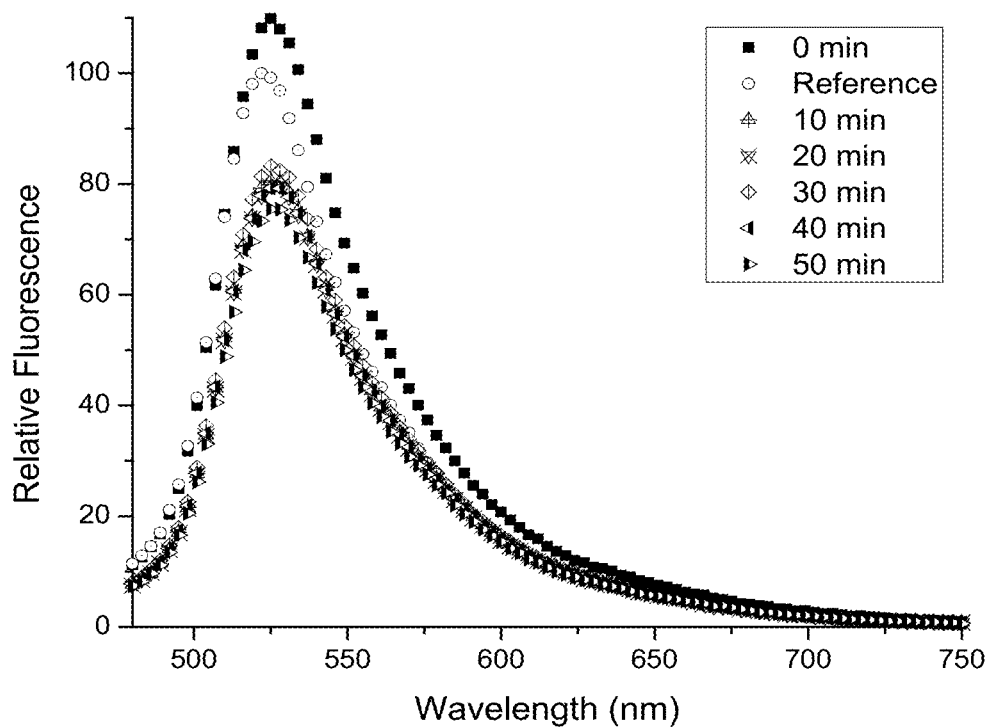
Figure 13F:
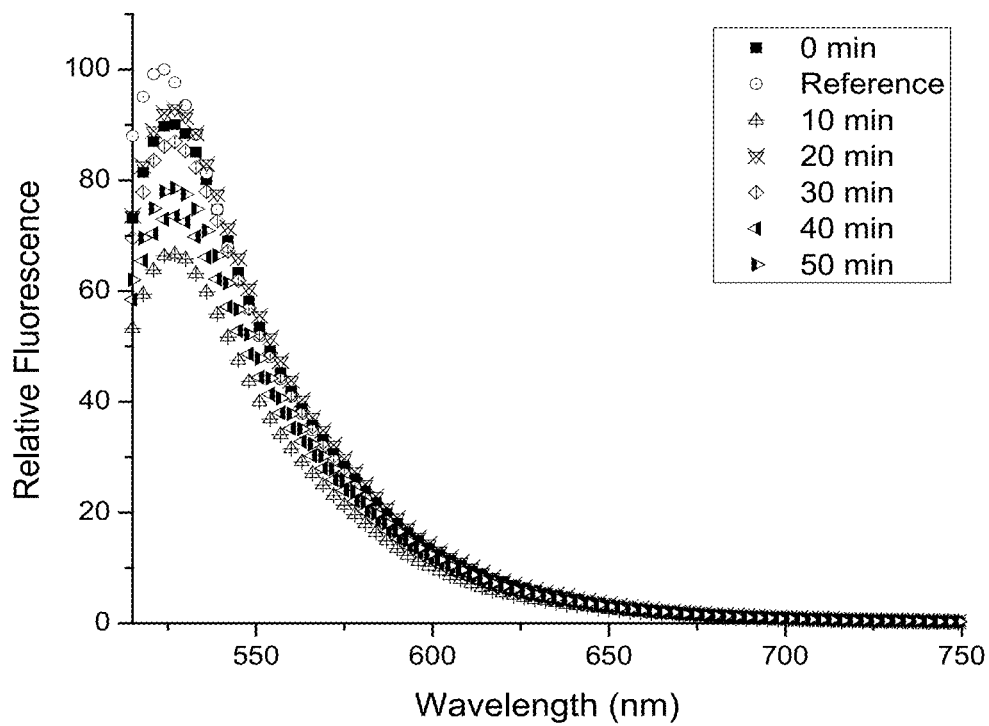

1.00 R560+1.00 RB+1.00 R640: FIGS. 13A-13F are spectra of a sample comprising 1.00 R560+1.00 RB+1.00 R640 nanoparticles and exposed to Demeton S, DFP, and Mustard for 50 min with data collection every 10 min. FIGS. 13A and 13B illustrate results versus Demeton-S at 450 nm and 485 nm, respectively; FIGS. 13C and 13D illustrate results versus DFP at 450 nm and 485 nm, respectively; and FIGS. 13E and 13F illustrate results versus Mustard at 450 nm and 485 nm, respectively. The R560+RB+R640 nanoparticles show good response for DFP regardless of the excitation wavelength; however, a response to Mustard takes under 20 min with 450 nm exposure and 50 min with 485 nm exposure.

Figure 14A:
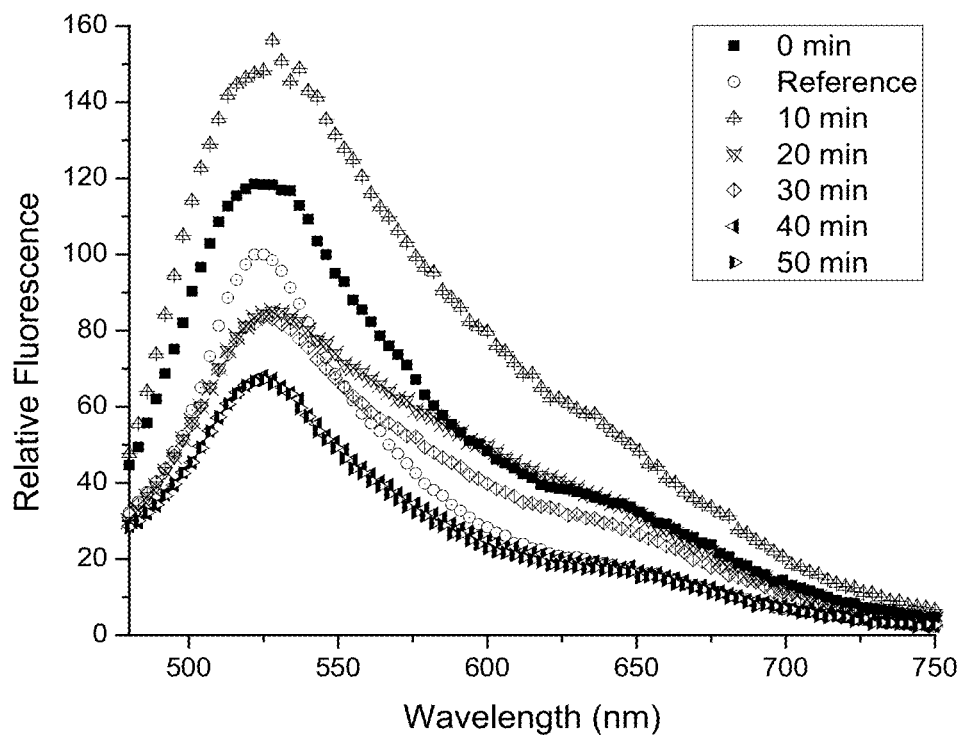
FIGS. 14A-14F are spectra of 1.00 R560+1.00 RB+2.00 R640 nanoparticles exposed to Demeton-S, diisopropyl fluorophosphates, and bis(2-chloroethyl) sulfide for 50 min with data collection every 10 min.
Figure 14B:
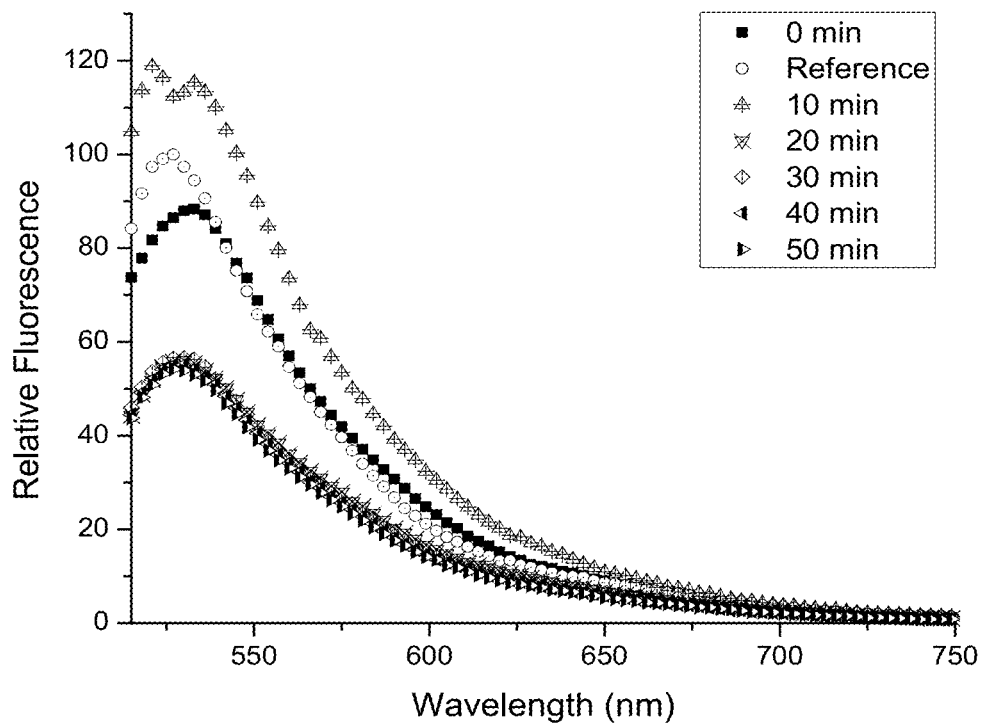
Figure 14C:
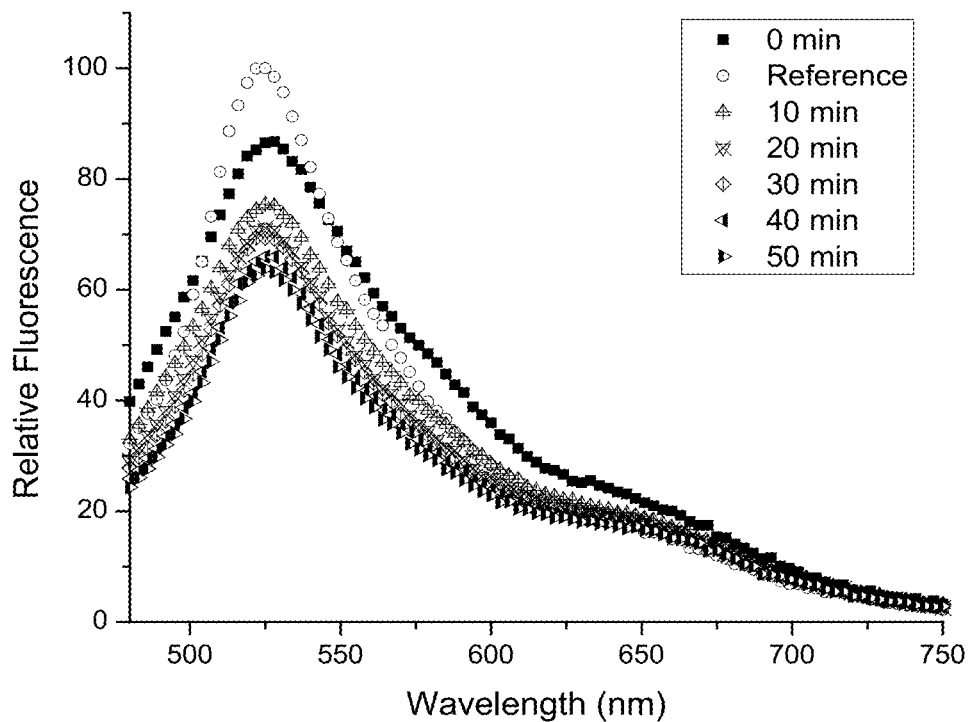
Figure 14D:
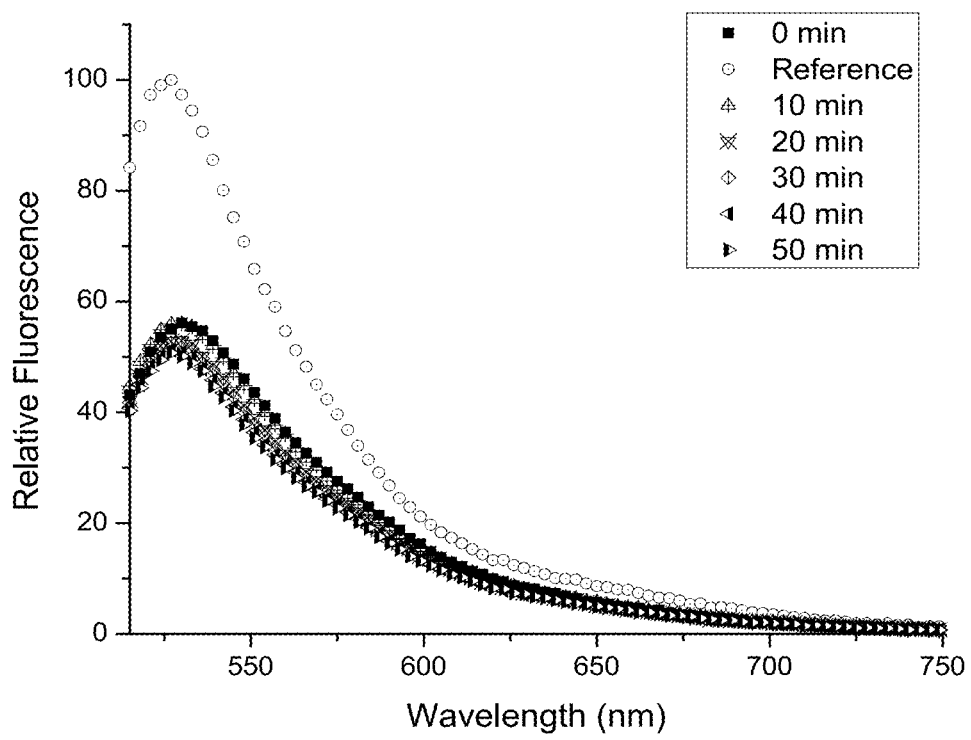
Figure 14E:
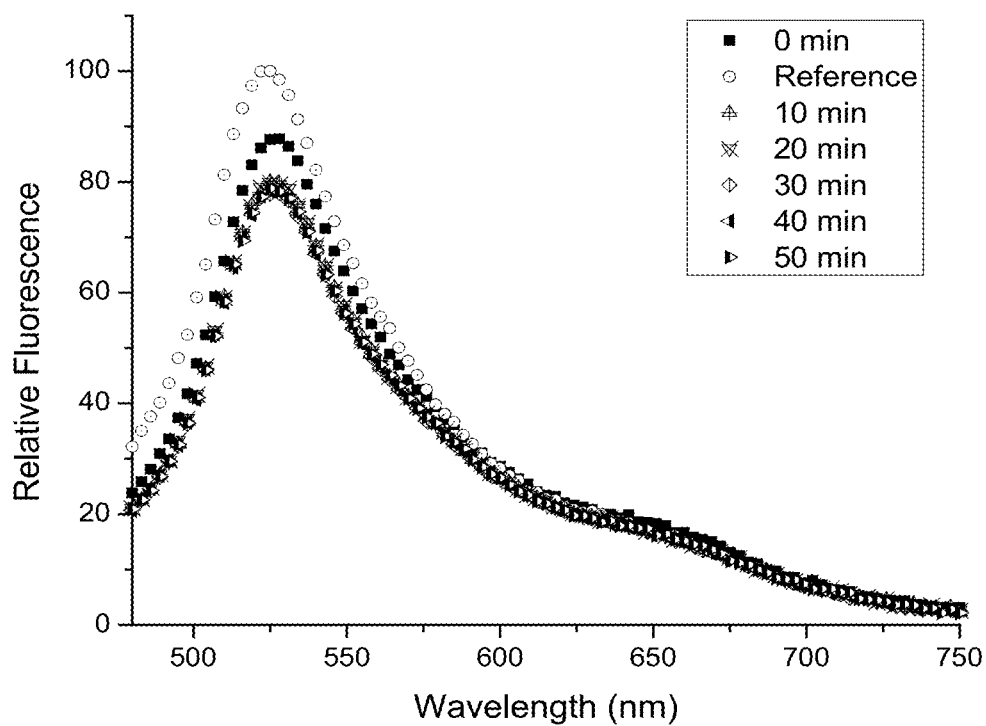
Figure 14F:
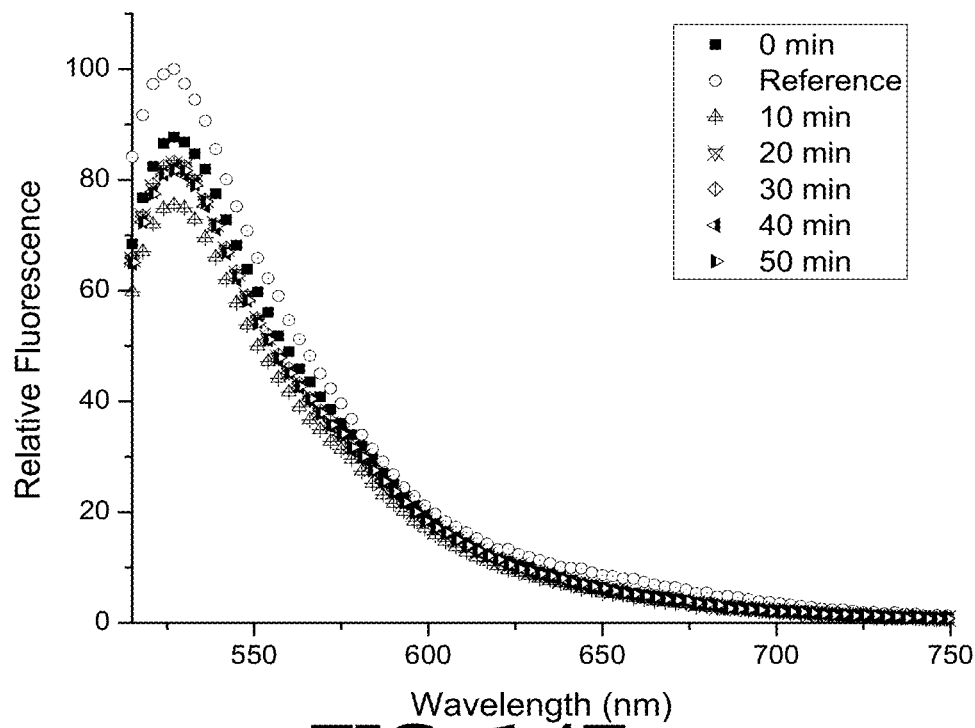

1.00 R560+1.00 RB+2.00 R640: FIGS. 14A-14F are spectra of a sample comprising 1.00 R560+1.00 RB+2.00 R640 nanoparticles and exposed to Demeton-S, DFP, and Mustard for 50 min with data collection every 10 min. FIGS. 14A and 14B illustrate results versus Demeton-S at 450 nm and 485 nm, respectively; FIGS. 14C and 14D illustrate results versus DFP at 450 nm and 485 nm, respectively; and FIGS. 14E and 14F illustrate results versus Mustard at 450 nm and 485 nm, respectively.

Figure 15A:
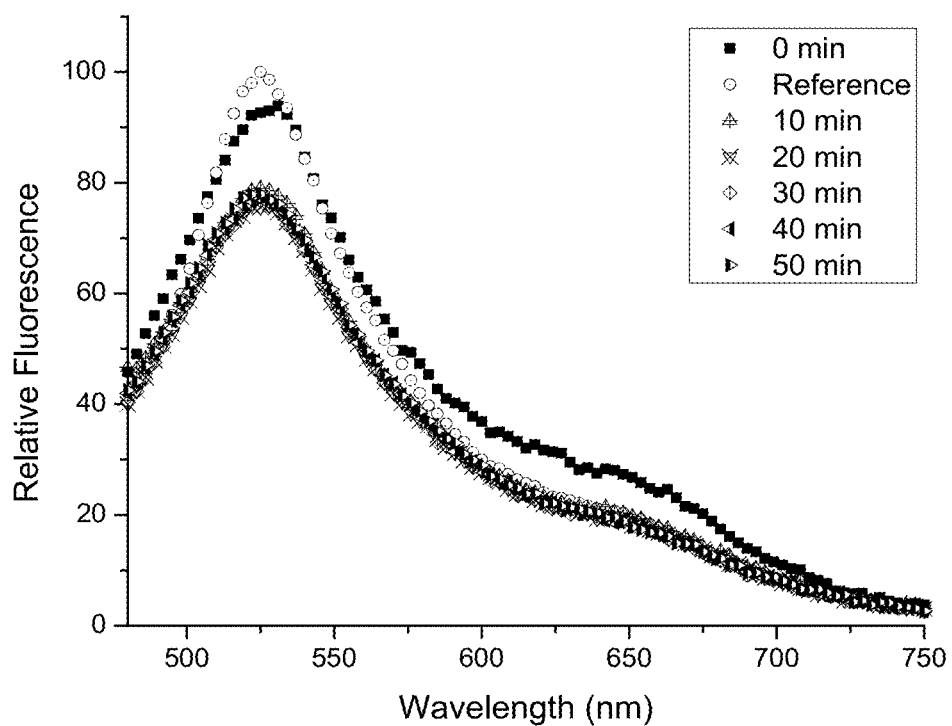
FIGS. 15A-15F are spectra of 1.00 R560+1.00 RB+3.00 R640 nanoparticles exposed to Demeton-S, diisopropyl fluorophosphates, and bis(2-chloroethyl) sulfide for 50 min with data collection every 10 min.
Figure 15B:
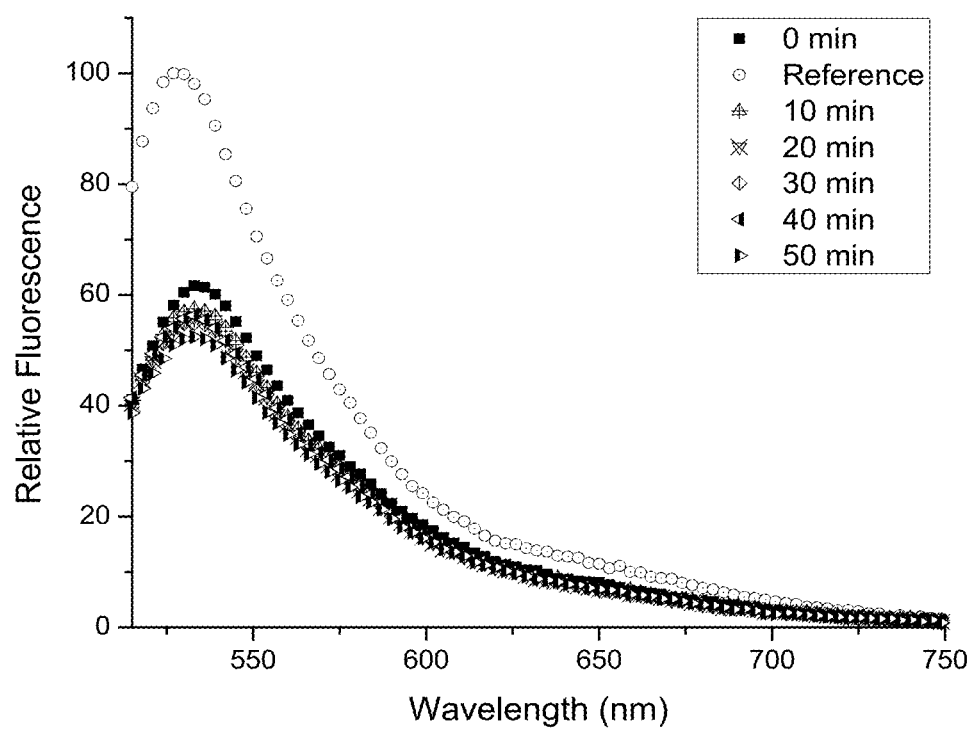
Figure 15C:
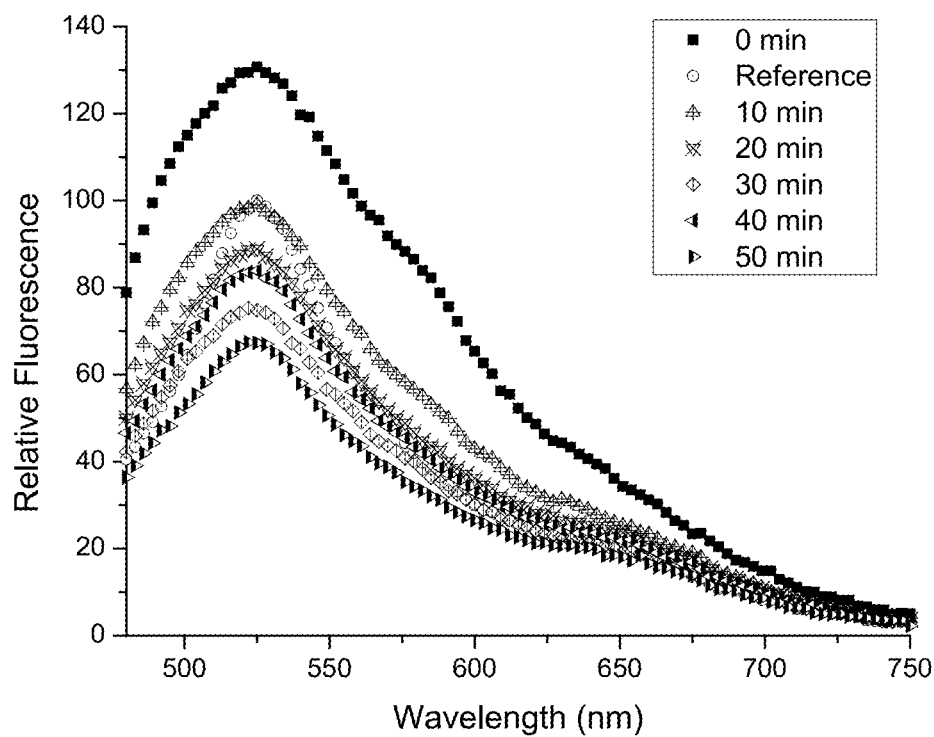
Figure 15D:
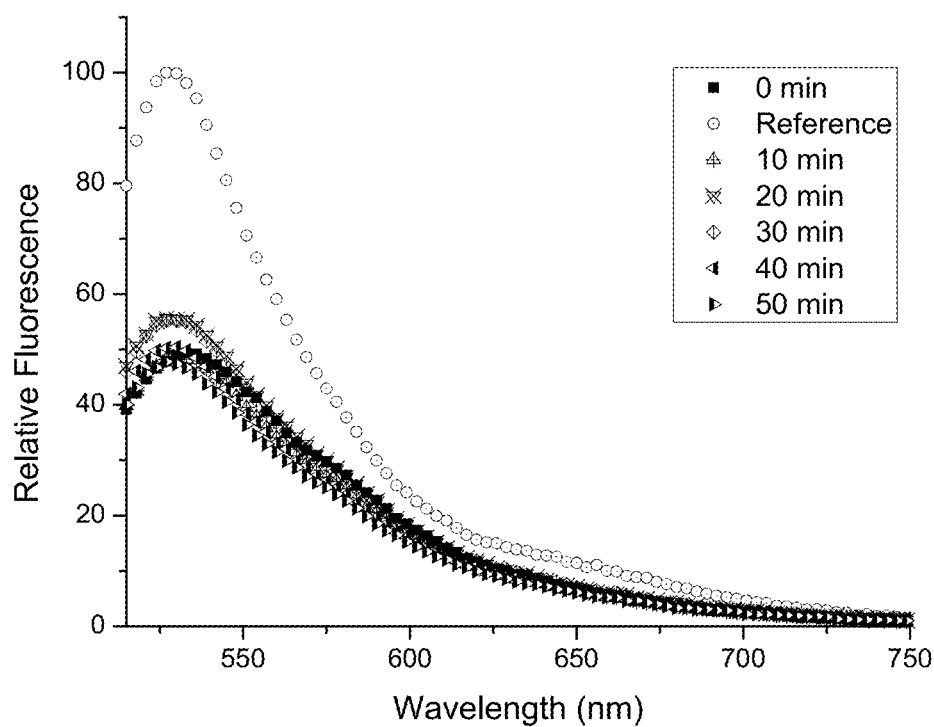
Figure 15E:
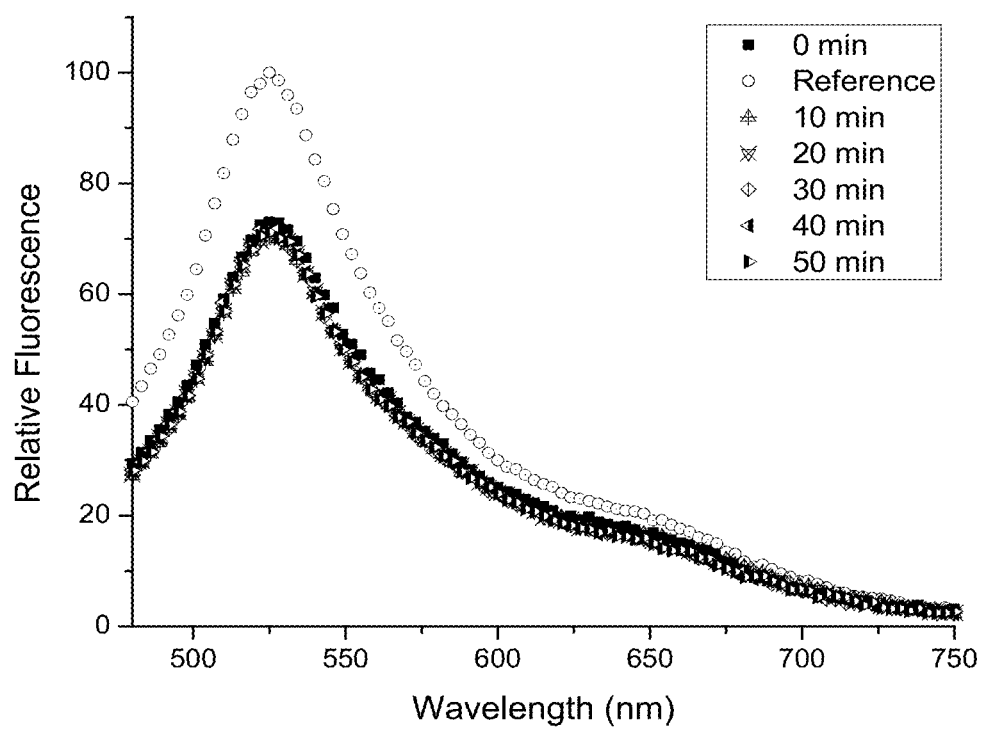
Figure 15F:
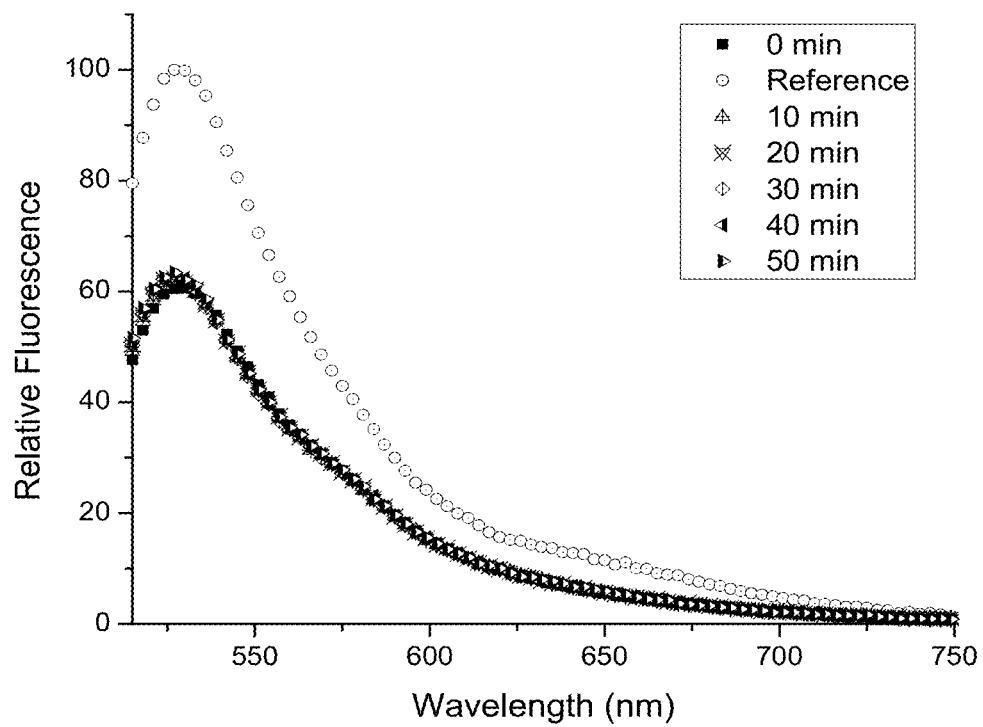

1.00 R560+1.00 RB+3.00 R640: FIGS. 15A-15F are spectra of 1.00 R560+1.00 RB+3.00 R640 nanoparticles and exposed to Demeton-S, DFP, and Mustard for 50 min with data collection every 10 min. FIGS. 15A and 15B illustrate results versus Demeton-S at 450 nm and 485 nm, respectively; FIGS. 15C and 135 illustrate results versus DFP at 450 nm and 485 nm, respectively; and FIGS. 15E and 15F illustrate results versus Mustard at 450 nm and 485 nm, respectively. The 1.00 R560+1.00 RB+3.00 R640 nanoparticles show significant response if excited at 485 nm for all three simulants, exhibiting stabilization times under 10 min.

Example 5

Figure 16A:
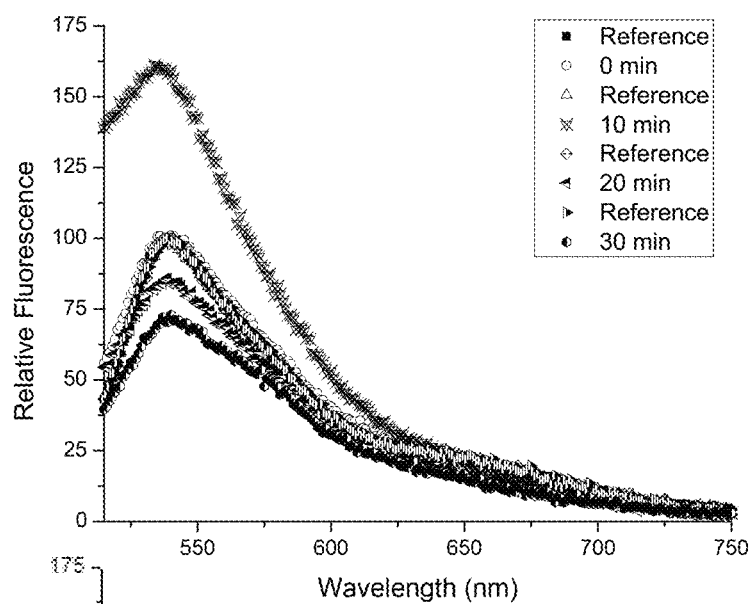
FIGS. 16A-16C are spectra of 1.00 RB nanoparticles exposed to Demeton-S, diisopropyl fluorophosphates, and bis(2-chloroethyl) sulfide, respectively, for 30 min with data collection every 10 min and with an excitation wavelength of about 485 nm.
Figure 16B:
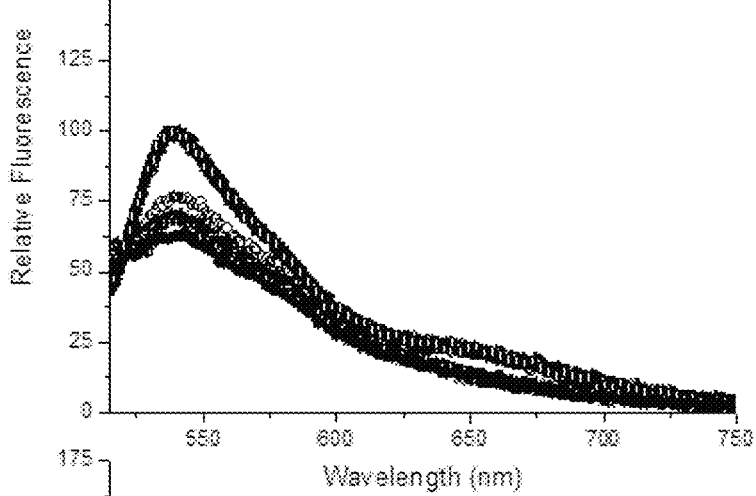
Figure 16C:
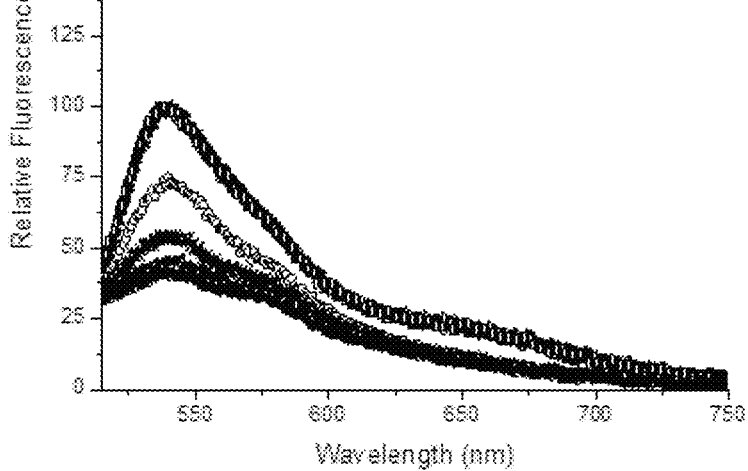

1.00 RB: FIGS. 16A-16C are spectra of a sample comprising 1.00 RB nanoparticles exposed to Demeton-S, DFP, and Mustard, respectively, for 30 min with data collection every 10 min and with an excitation wavelength of about 485 nm. The single dye nanoparticles were exposed only to 485 nm excitation wavelength due to very weak light absorption at 450 nm. The 1.00 RB nanoparticles demonstrated a response to DFP (FIG. 16B) and Mustard (FIG. 16C) with stabilization times ranging from 10 min to 20 min respectively. Demeton-S (FIG. 16A) caused an initial rise in the spectrum upon addition of the chemical warfare agent simulant, followed by a decrease of the intensity to below the reference line.

Figure 17A:
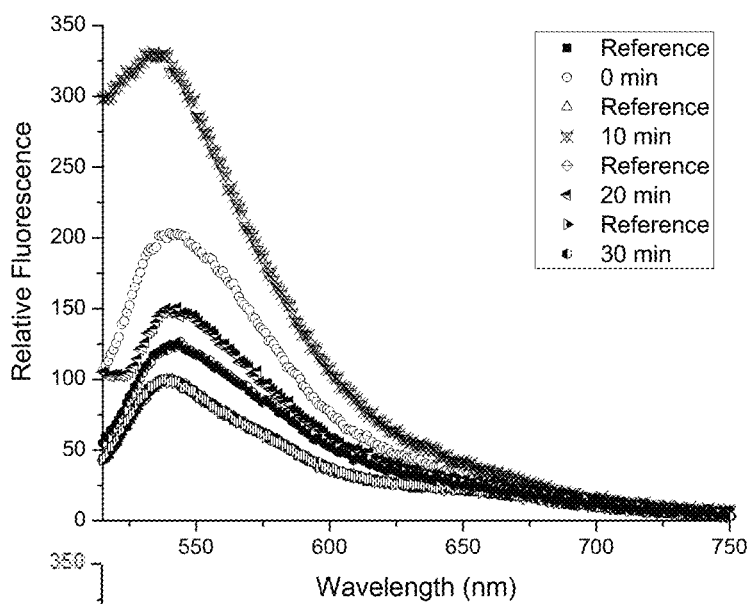
FIGS. 17A-17C are spectra of 2.00 RB nanoparticles exposed to Demeton-S, diisopropyl fluorophosphates, and bis(2-chloroethyl) sulfide, respectively for 30 min with data collection every 10 min and with an excitation wavelength of about 485 nm.
Figure 17B:
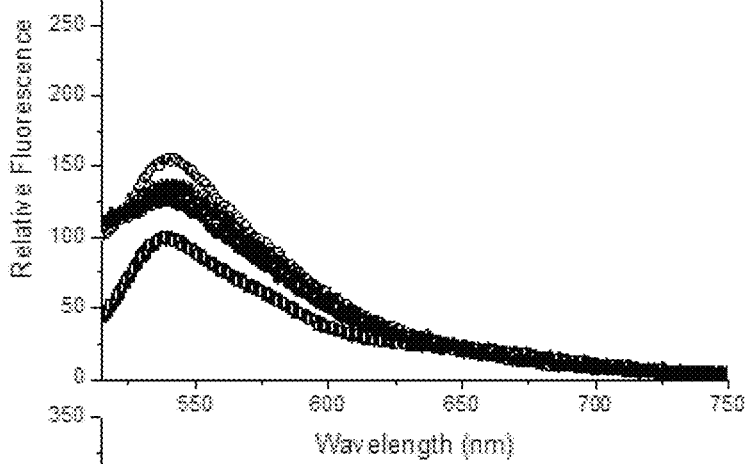
Figure 17C:
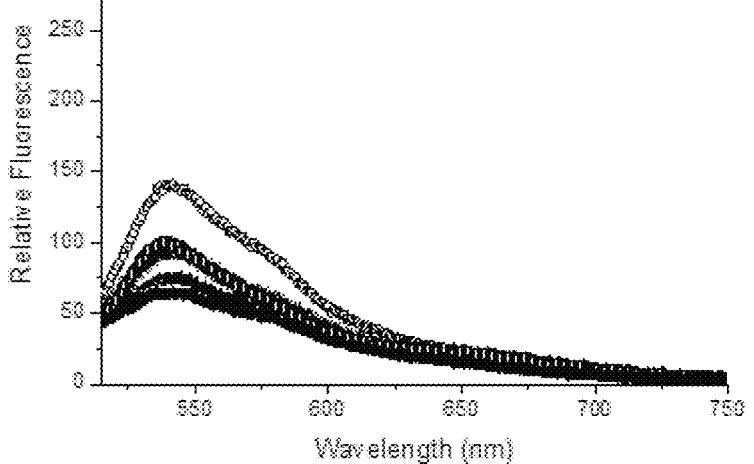

2.00 RB: FIGS. 17A-17C are spectra of a sample comprising 2.00 RB nanoparticles exposed to Demeton-S, DFP, and Mustard, respectively for 30 min with data collection every 10 min and with an excitation wavelength of about 485 nm. The 2.00 RB nanoparticles demonstrate an "oscillating" behavior of the spectra, with an initial increase above reference line followed by a drop below the reference line.

Figure 18A:
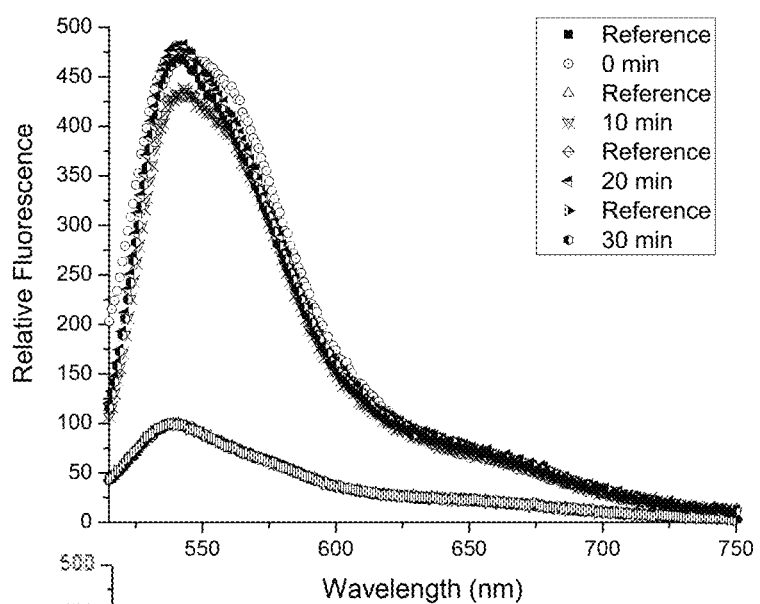
FIGS. 18A-18C are spectra of 3.00 RB nanoparticles exposed to Demeton-S, diisopropyl fluorophosphates, and bis(2-chloroethyl) sulfide for 30 min with data collection every 10 min and with an excitation wavelength of about 485 nm.
Figure 18B:
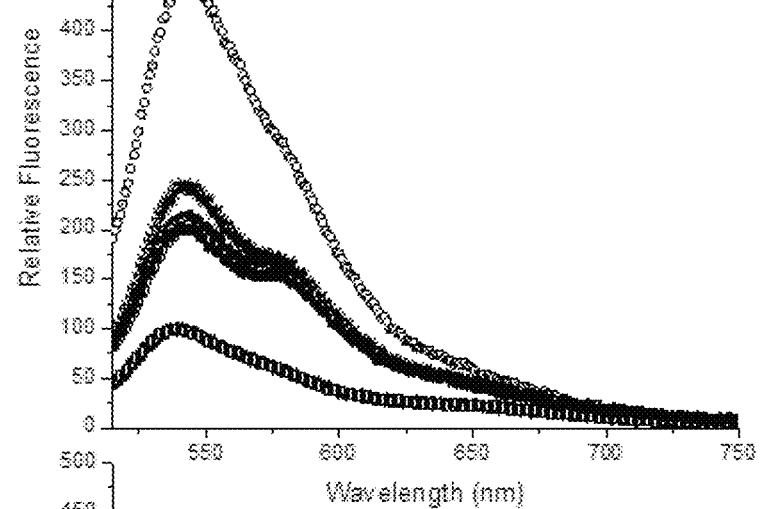
Figure 18C:
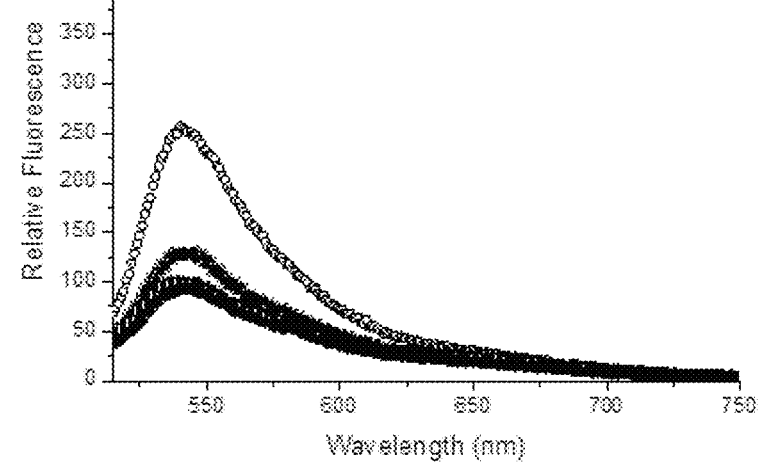

3.00 RB: FIGS. 18A-18C are spectra of a sample comprising 3.00 RB nanoparticles exposed to Demeton-S, DFP, and Mustard for 30 min with data collection every 10 min and with an excitation wavelength of about 485 nm. The 3.00 RB nanoparticles were very responsive to Demeton-S (FIG. 18A) and DFP (FIG. 18B) while the 3.00 RB nanoparticles with Mustard (FIG. 18C) had spectra coinciding with reference spectra after 30 min. The presence of DFP caused the fluorescence peak to split.

Figure 19A:
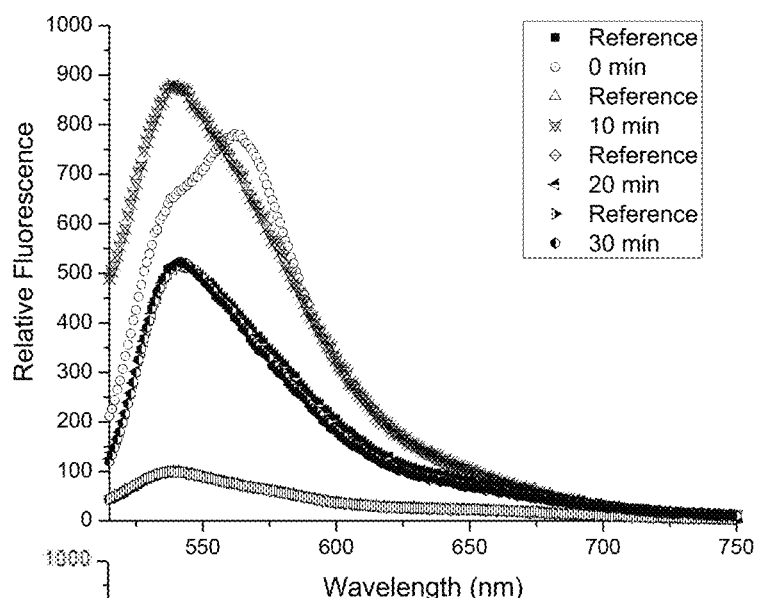
FIGS. 19A-19C are spectra of 4.00 RB nanoparticles exposed to Demeton-S, diisopropyl fluorophosphates, and bis(2-chloroethyl) sulfide for 30 min with data collection every 10 min and with an excitation wavelength of about 485 nm.
Figure 19B:
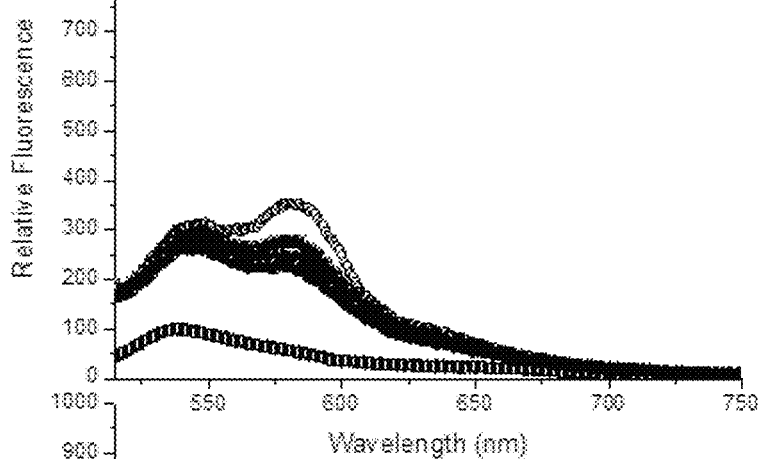
Figure 19C:
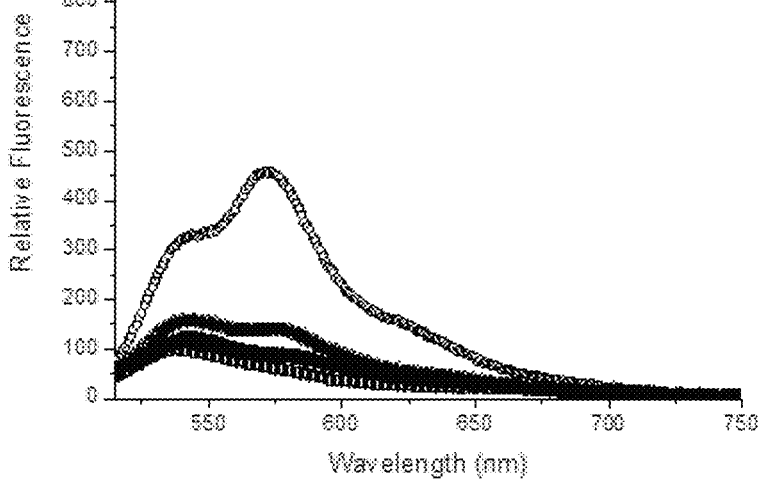

4.00 RB: FIGS. 19A-19C are spectra of a sample comprising 4.00 RB nanoparticles exposed to Demeton-S, DFP, and Mustard for 30 min with data collection every 10 min and with an excitation wavelength of about 485 nm. The 4.00 RB nanoparticles were very responsive to Demeton-S (FIG. 19A) and DFP (FIG. 19B) while the 4.00 RB nanoparticles with Mustard (FIG. 19C) had spectra coinciding with reference spectra after 30 min. The presence of DFP caused the fluorescence peak to split.

Figure 20A:
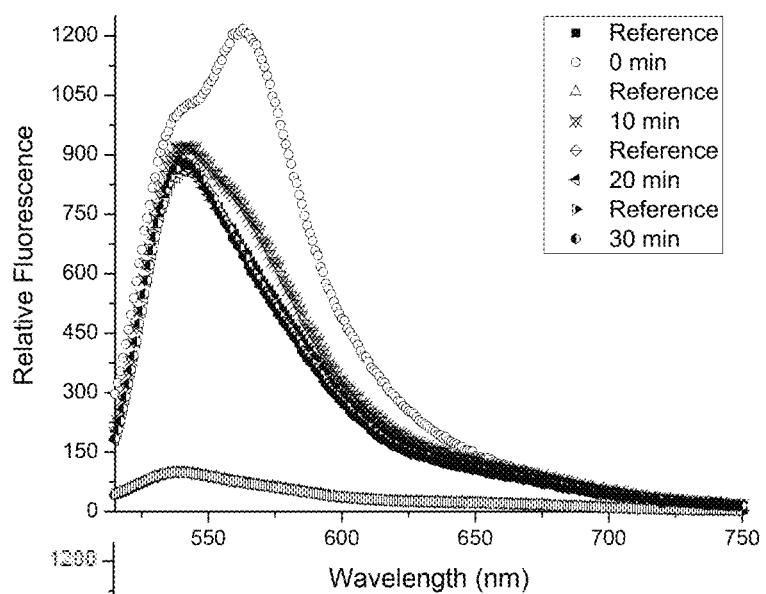
FIGS. 20A-20C are spectra of 6.00 RB nanoparticles exposed to Demeton-S, diisopropyl fluorophosphates, and bis(2-chloroethyl) sulfide for 30 min with data collection every 10 min and with an excitation wavelength of about 485 nm.
Figure 20B:
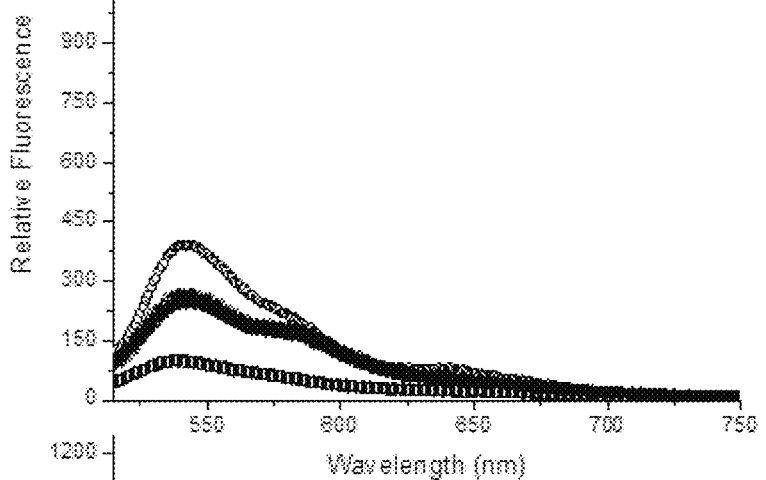
Figure 20C:
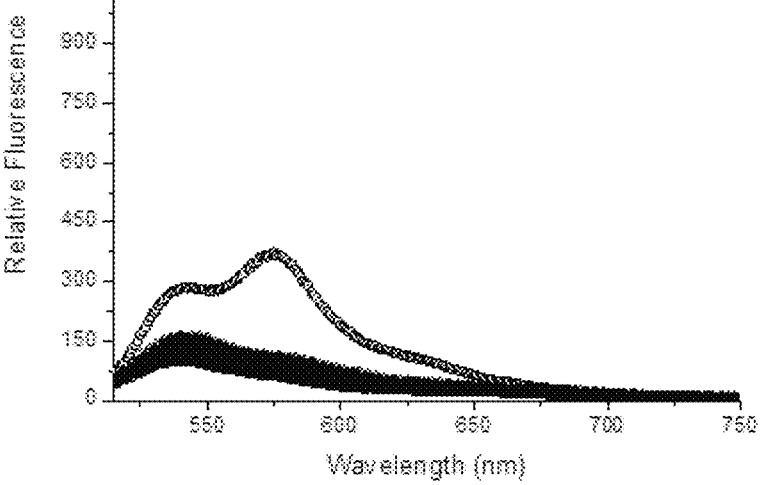

6.00 RB: FIGS. 20A-20C are spectra of a sample comprising 6.00 RB nanoparticles exposed to Demeton-S, DFP, and Mustard for 30 min with data collection every 10 min and with an excitation wavelength of about 485 nm. The 6.00 RB nanoparticles were very responsive to Demeton-S (FIG. 20A) and DFP (FIG. 20B) while the 6.00 RB nanoparticles with Mustard (FIG. 20C) had spectra coinciding with reference spectra after 30 min. The presence of any of one of the chemical warfare agent simulants caused the fluorescence peak to split.

Example 6

X RB: FIGS. 21A-25C demonstrate a high response with fast stabilization time of under 10 min (except for Demeton-S) for X RB nanoparticles, wherein X ranges from 1.00 to 6.00.

Figure 21A:
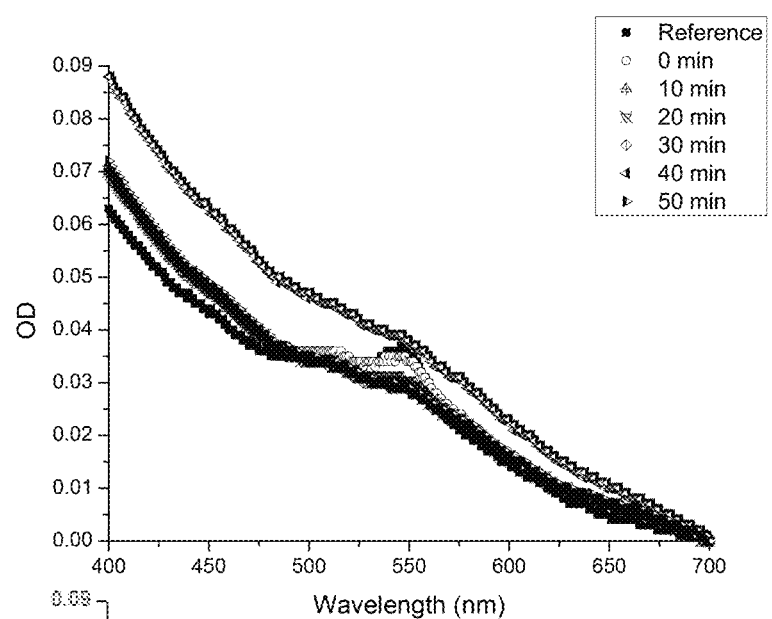
FIGS. 21A-21C are spectra of 1.00 RB against Demeton-S, diisopropyl fluorophosphates, and bis(2-chloroethyl) sulfide, respectively.
Figure 21B:
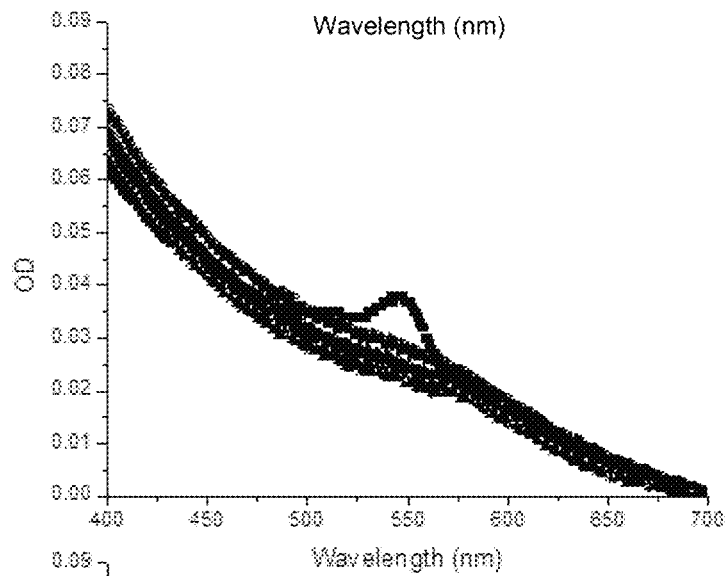
Figure 21C:
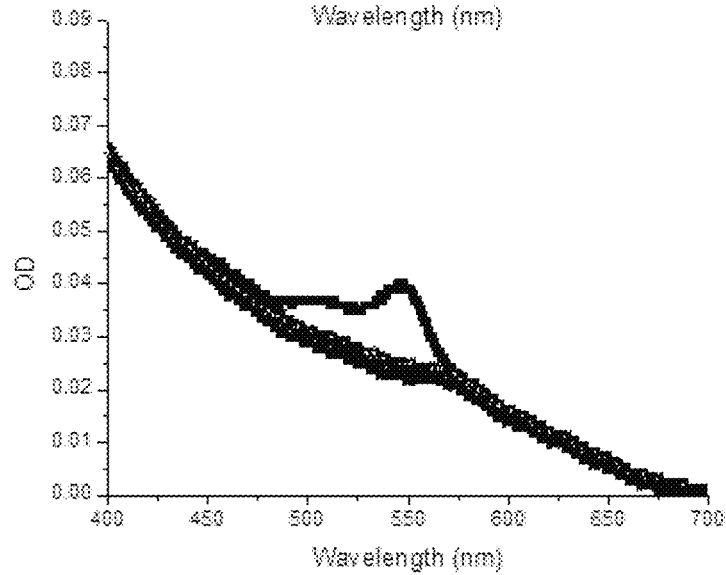

FIGS. 21A-21C are spectra of 1.00 RB against Demeton-S, DFP, and Mustard, respectively.

Figure 22A:
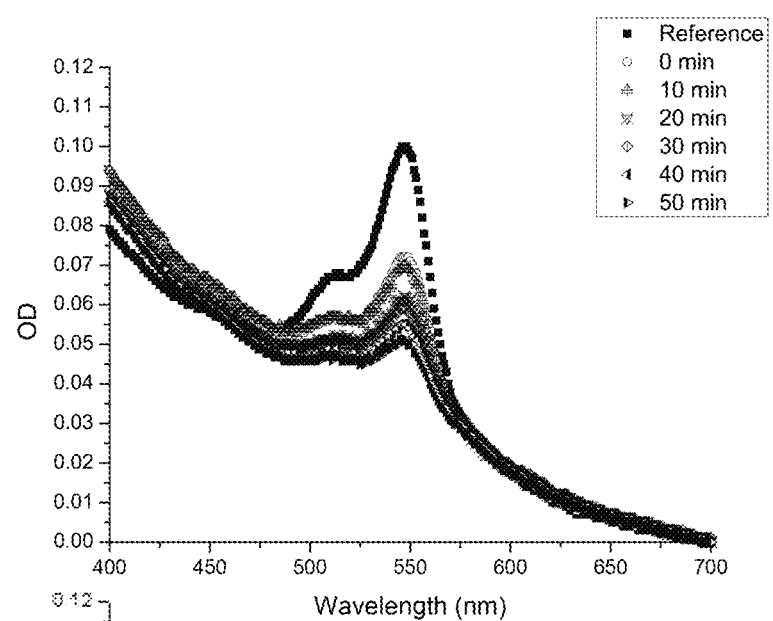
FIGS. 22A-22C are spectra of 2.00 RB against Demeton-S, diisopropyl fluorophosphates, and bis(2-chloroethyl) sulfide, respectively.
Figure 22B:
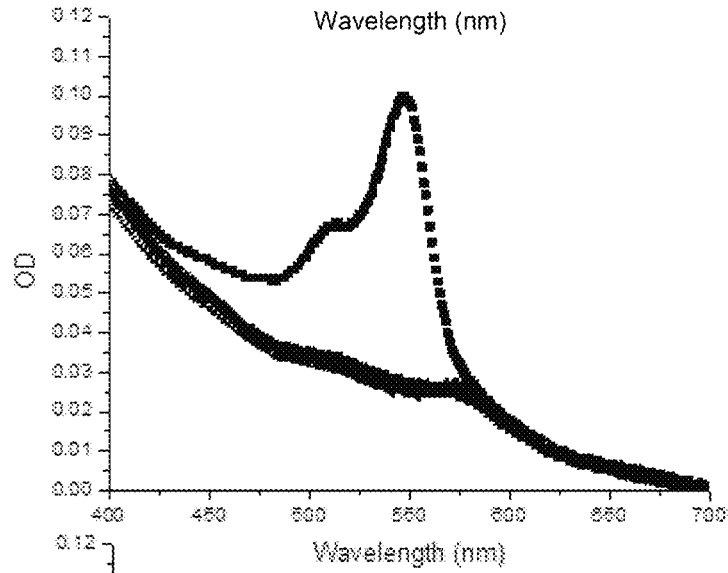
Figure 22C:
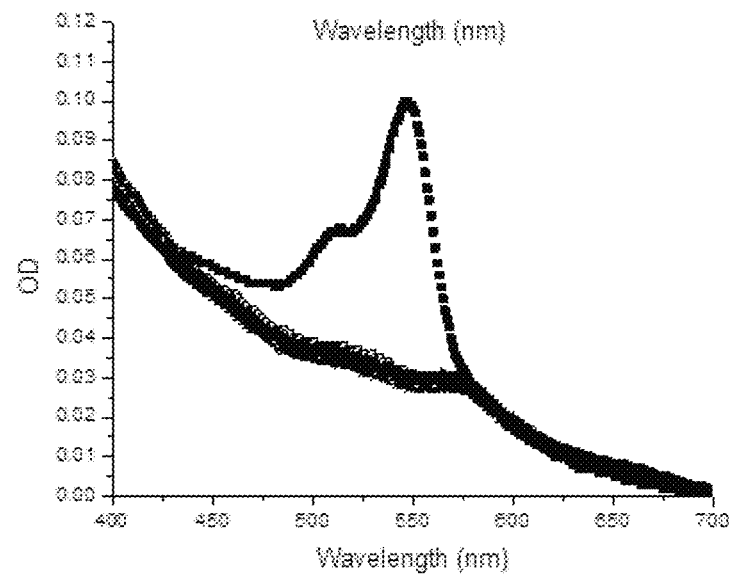

FIGS. 22A-22C are spectra of 2.00 RB against Demeton-S, DFP, and Mustard, respectively.

Figure 23A:
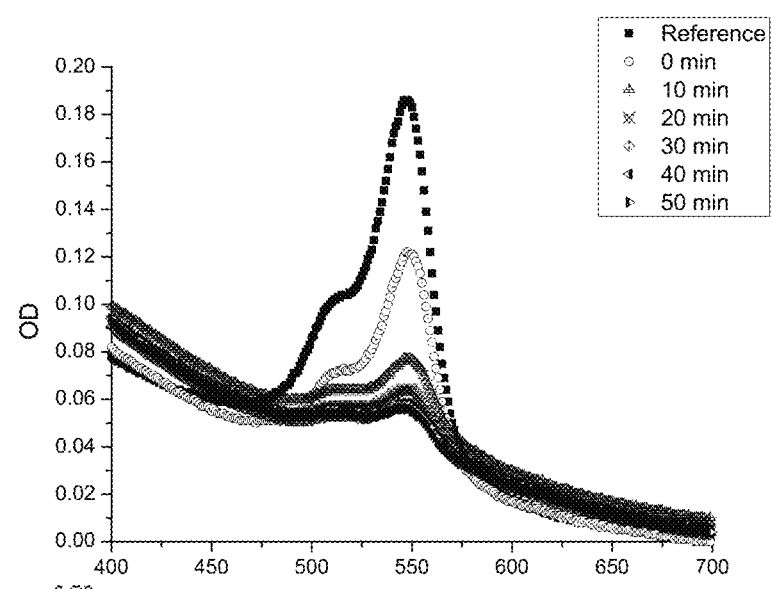
FIGS. 23A-23C are spectra of 3.00 RB against Demeton-S, diisopropyl fluorophosphates, and bis(2-chloroethyl) sulfide, respectively.
Figure 23B:
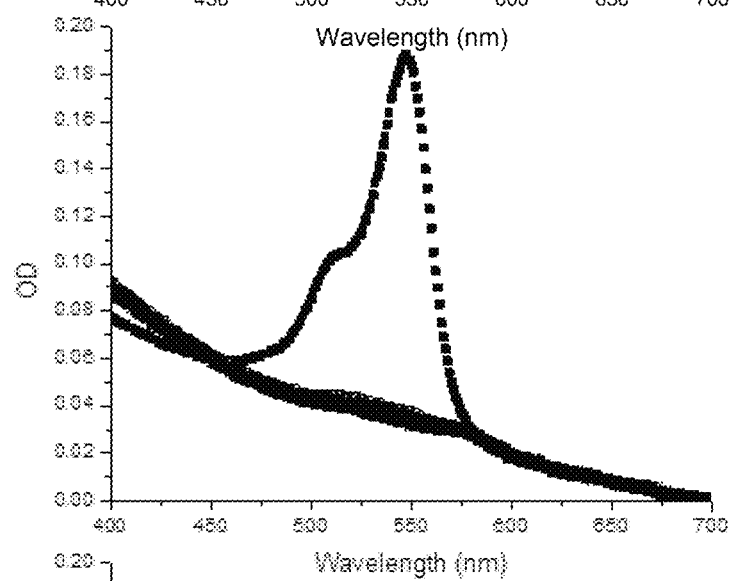
Figure 23C:
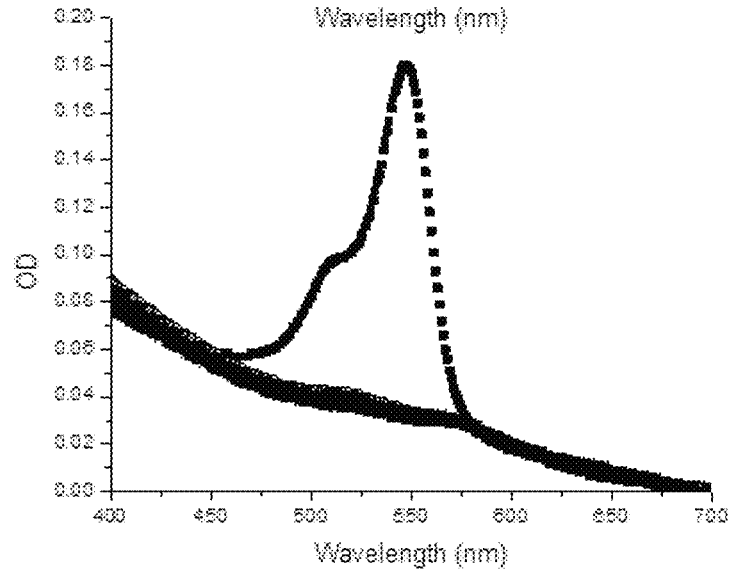

FIGS. 23A-23C are spectra of 3.00 RB against Demeton-S, DFP, and Mustard, respectively.

Figure 24A:
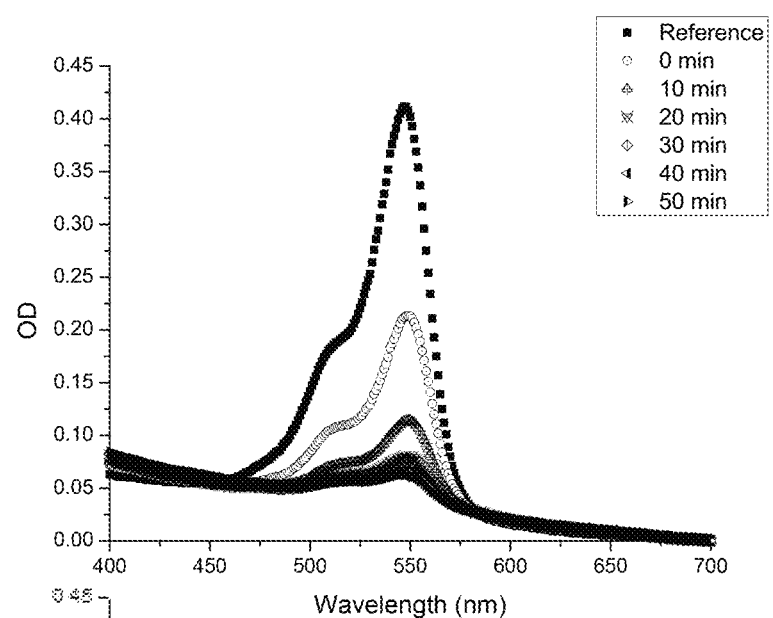
FIGS. 24A-24C are spectra of 4.00 RB against Demeton-S, diisopropyl fluorophosphates, and bis(2-chloroethyl) sulfide, respectively.
Figure 24B:
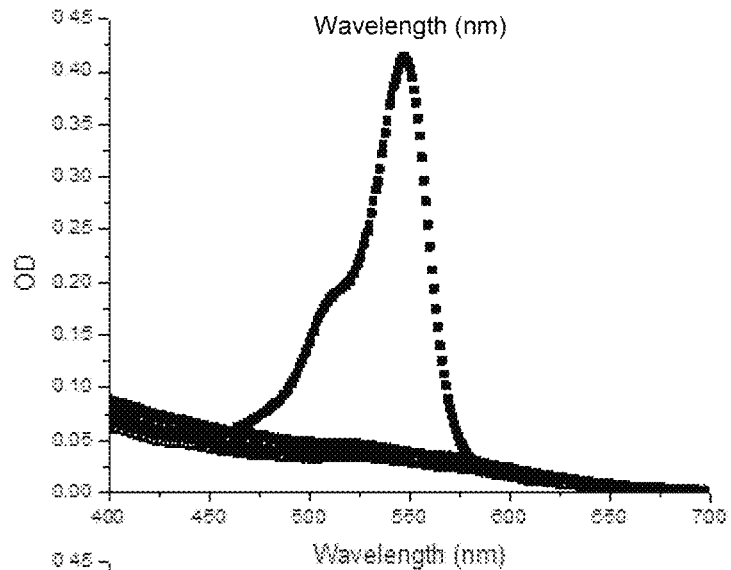
Figure 24C:
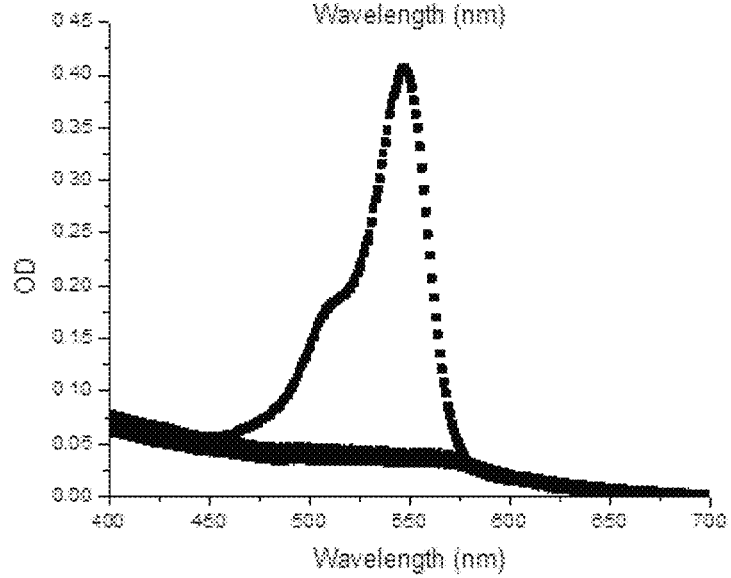

FIGS. 24A-24C are spectra of 4.00 RB against Demeton-S, DFP, and Mustard, respectively.

Figure 25A:
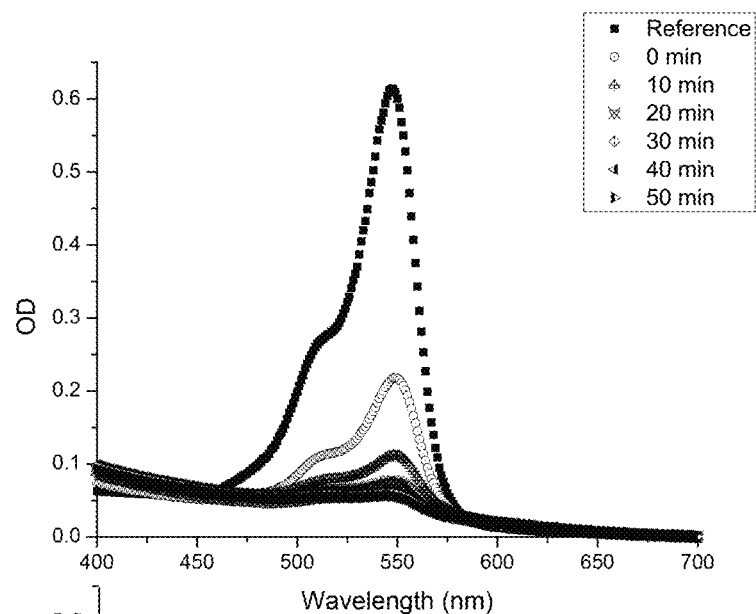
FIGS. 25A-25C are spectra of 6.00 RB against Demeton-S, diisopropyl fluorophosphates, and bis(2-chloroethyl) sulfide, respectively.
Figure 25B:
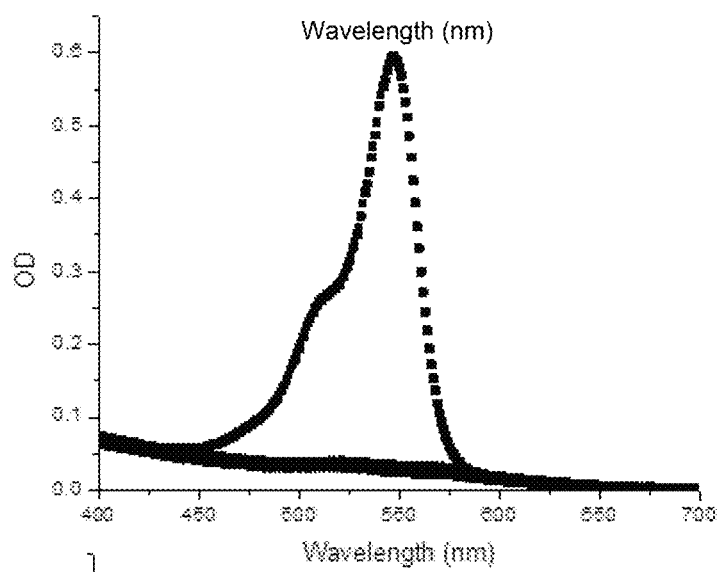
Figure 25C:
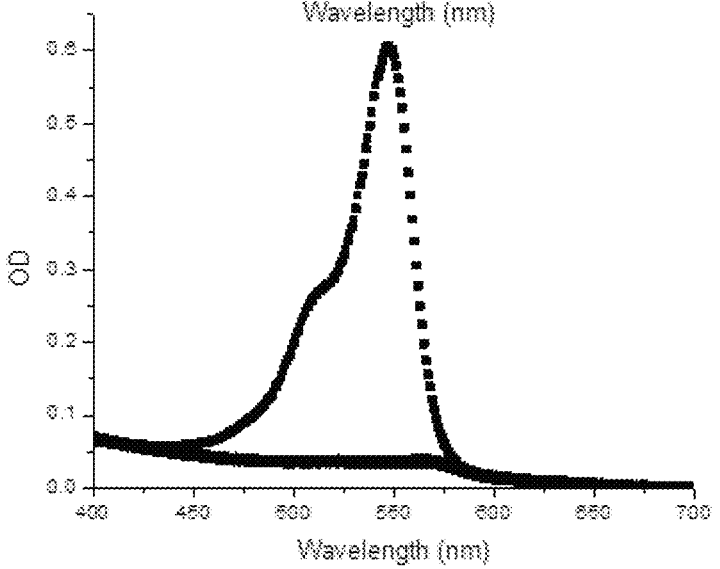

FIGS. 25A-25C are spectra of 6.00 RB against Demeton-S, DFP, and Mustard, respectively.

All samples responded to the presence of simulants and have fast stabilization time under 10 min.

Example 7

X RB dilutions: FIGS. 26A-36C demonstrate the response of RB versus various dilutions with each chemical warfare agent simulant, wherein X ranges from 3.00 to 6.00.

Figure 26A:
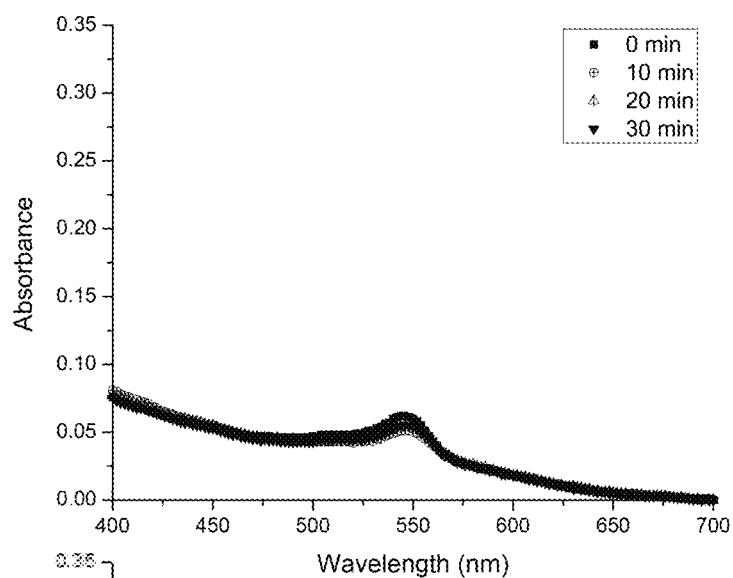
FIGS. 26A-26C are spectra of 3.00 RB, 4.00 RB, and 6.00 RB, respectively, in a 1:2 dilution with Demeton-S.
Figure 26B:
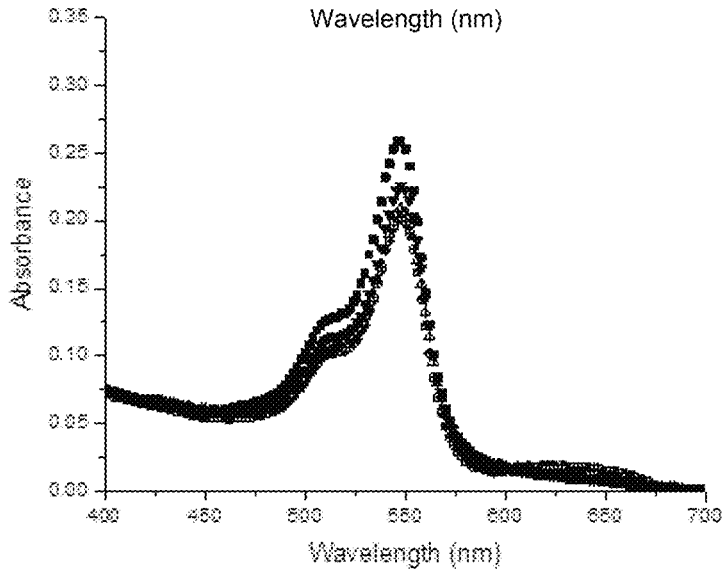
Figure 26C:
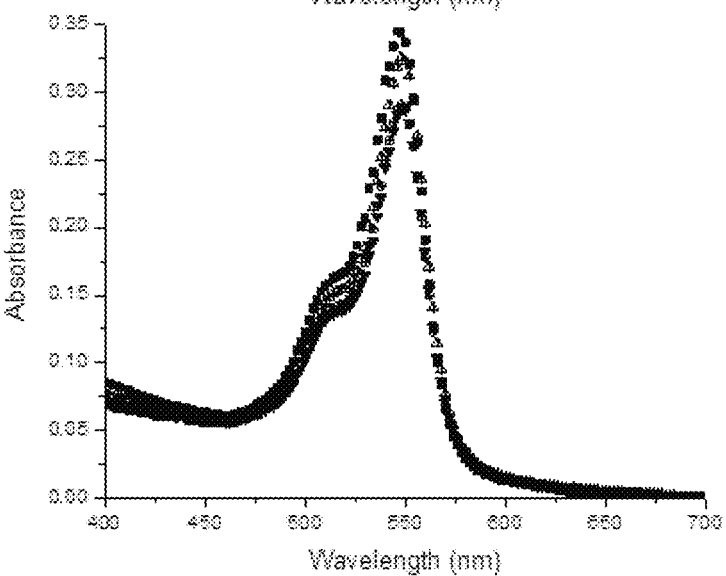
Figure 27A:
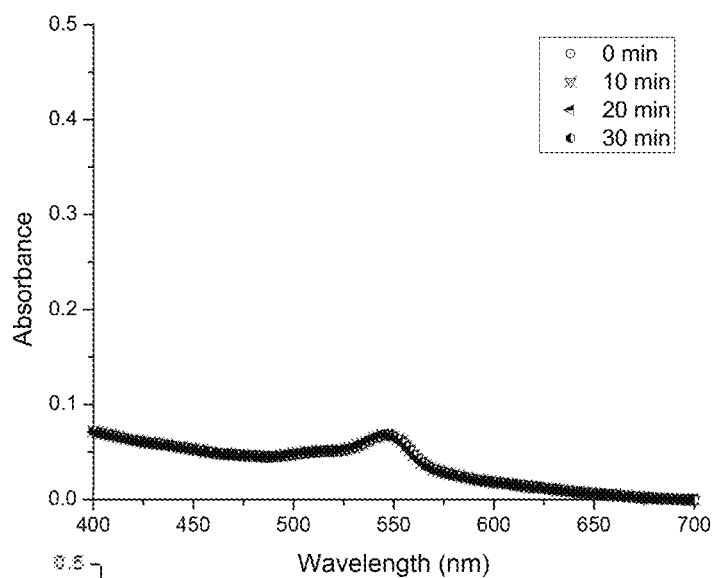
FIGS. 27A-27C are spectra of 3.00 RB, 4.00 RB, and 6.00 RB, respectively, in a 1:5 dilution with Demeton-S.
Figure 27B:
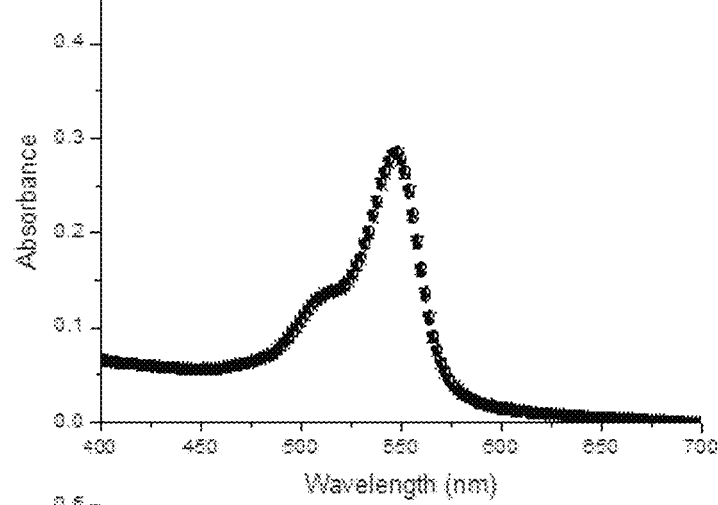
Figure 27C:
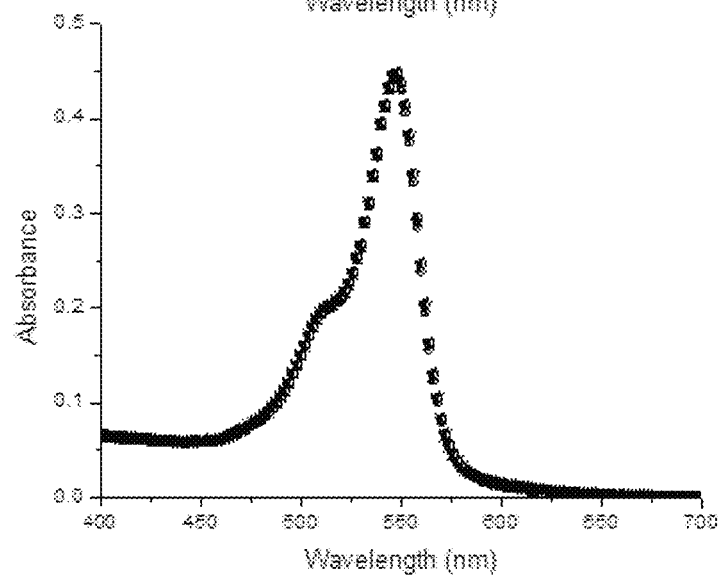
Figure 28A:
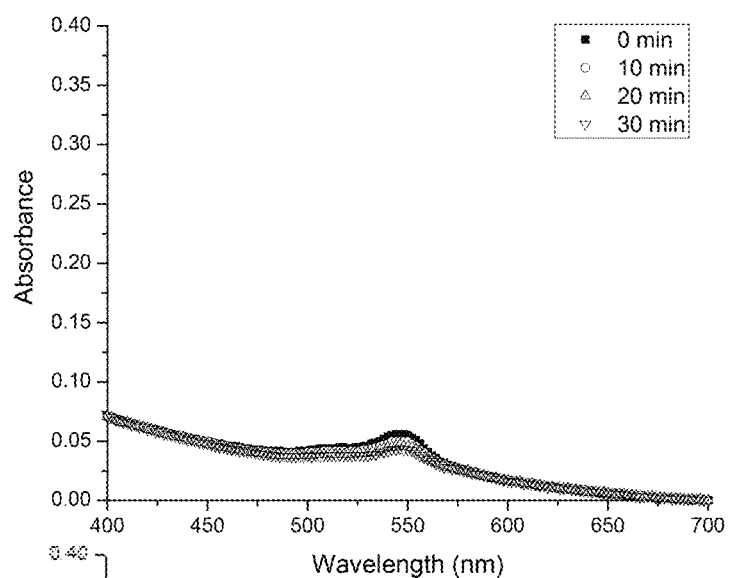
FIGS. 28A-28C are spectra of 3.00 RB, 4.00 RB, and 6.00 RB, respectively, in a 1:10 dilution with Demeton-S.
Figure 28B:
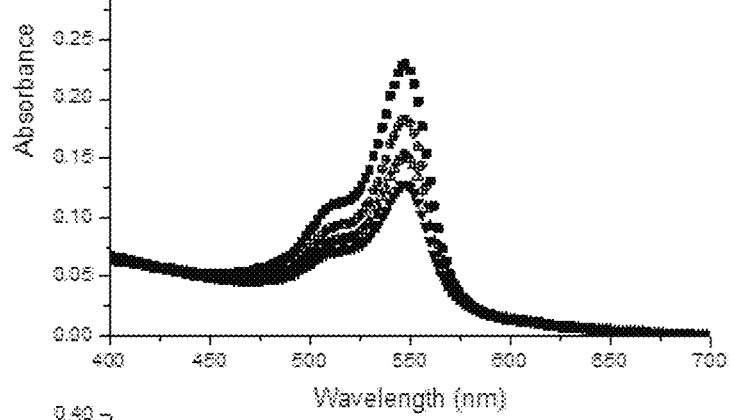
Figure 28C:
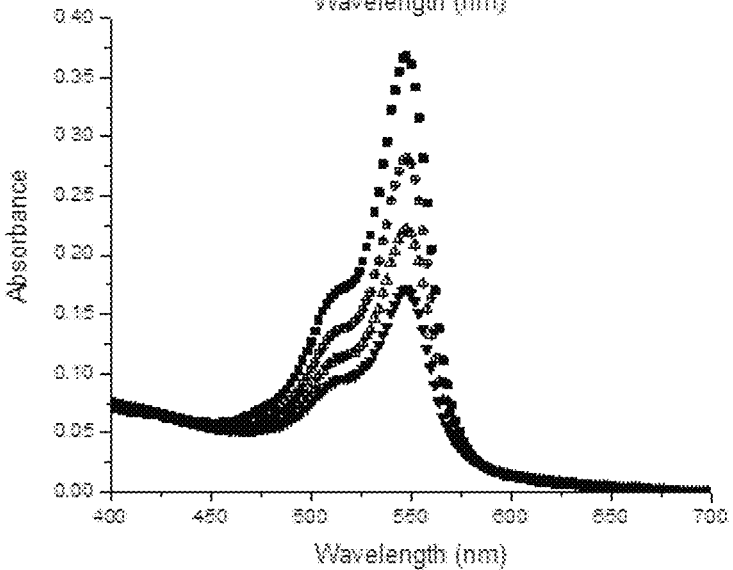

100 μL aliquots of samples each comprising one of 3.00 RB nanoparticles, 4.00 RB nanoparticles, and 6.00 RB nanoparticles were mixed with 200 μL of water and either 0.5 μL or 0.25 μL (i.e., 1-to-2 and 1-to-5 dilutions, respectively) of Demeton-S. FIGS. 26A-26C are spectra of 3.00 RB, 4.00 RB, and 6.00 RB, respectively, in a 1:2 dilution with Demeton-S; FIGS. 27A-27C are spectra of 3.00 RB, 4.00 RB, and 6.00 RB, respectively, in a 1:5 dilution with Demeton-S; and FIGS. 28A-28C are spectra of 3.00 RB, 4.00 RB, and 6.00 RB, respectively, in a 1:10 dilution with DFP. A detection limit of 0.5 μL per 300 μL (100 μL of each sample with 200 μL of water) was determined.

Figure 29A:
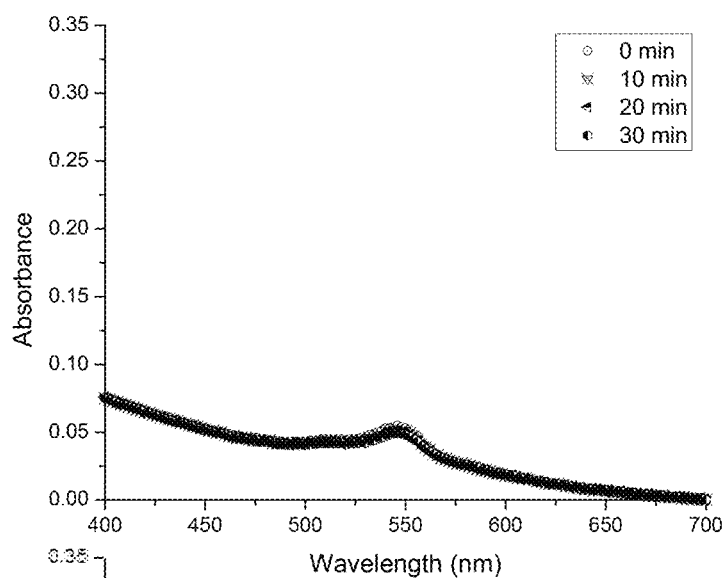
FIGS. 29A-29C are spectra of 2.00 RB, 4.00 RB, and 6.00 RB, respectively, in a 1:20 dilution with diisopropyl fluorophosphates.
Figure 29B:
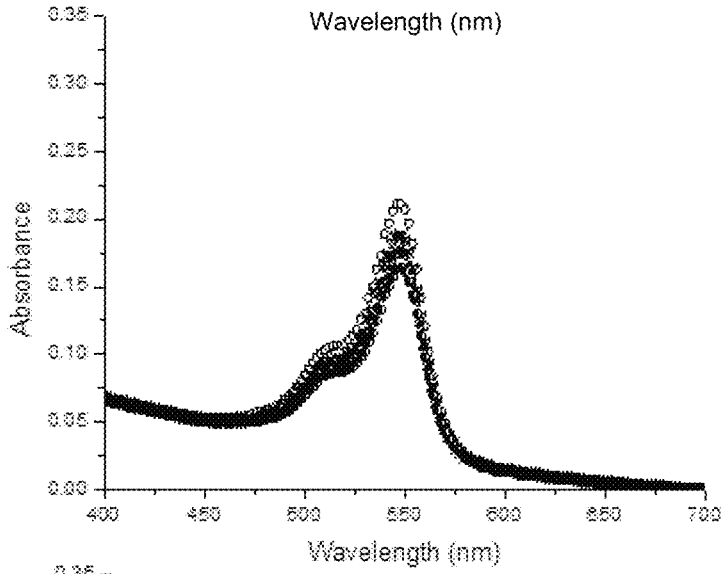
Figure 29C:
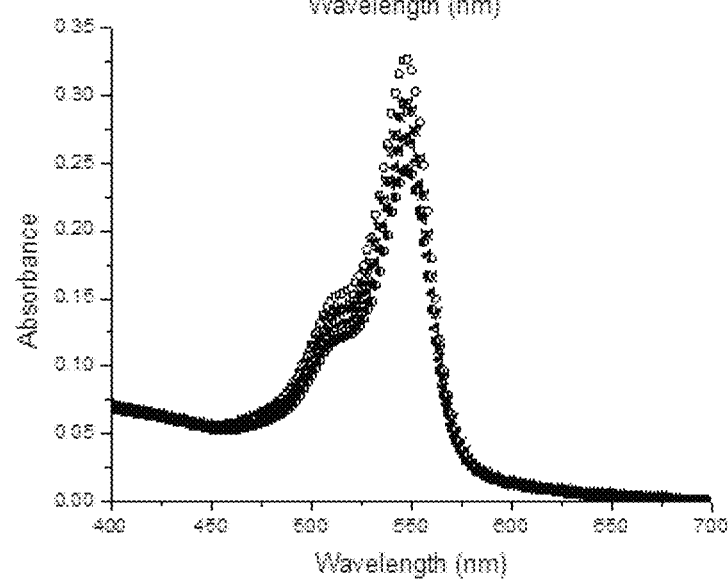
Figure 30A:
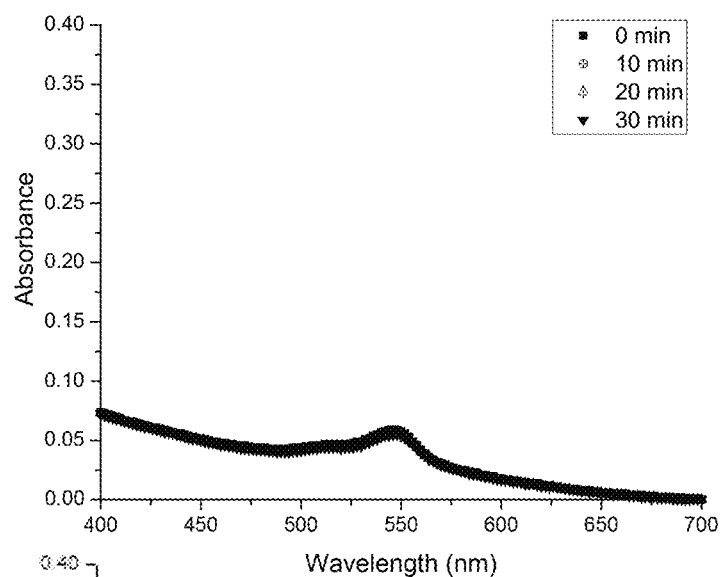
FIGS. 30A-30C are spectra of 3.00 RB, 4.00 RB, and 6.00 RB, respectively, in a 1:30 dilution with diisopropyl fluorophosphates.
Figure 30B:
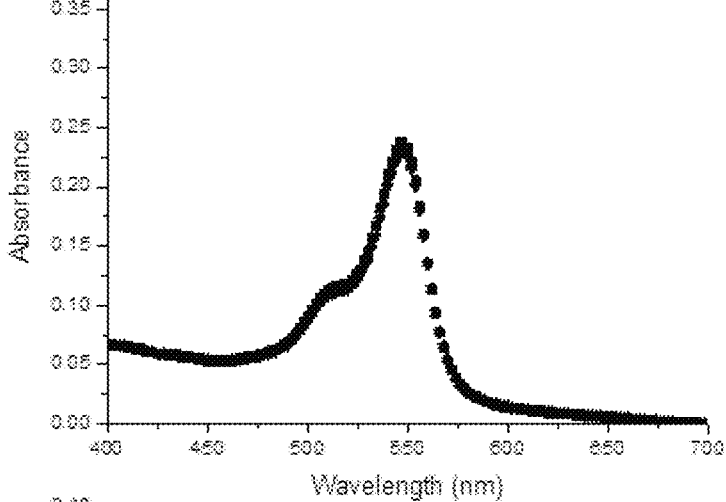
Figure 30C:
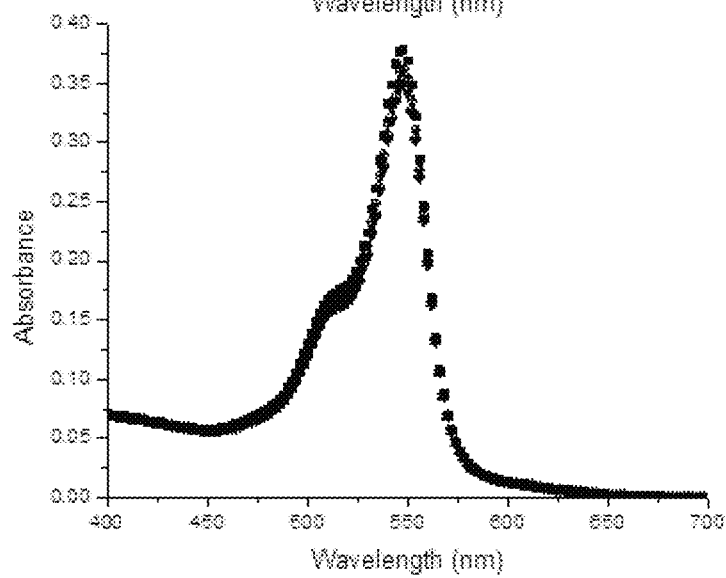
Figure 31A:
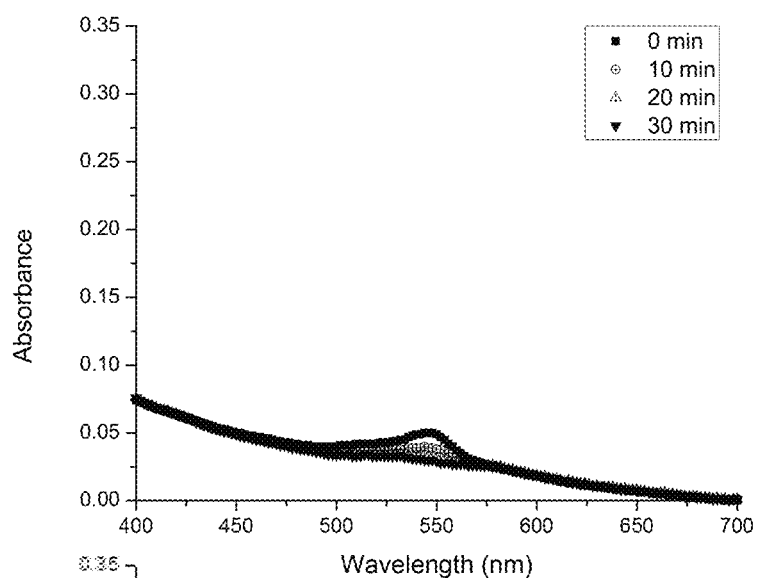
FIGS. 31A-31C are spectra of 3.00 RB, 4.00 RB, and 6.00 RB, respectively, in a 1:10 dilution with diisopropyl fluorophosphates.
Figure 31B:
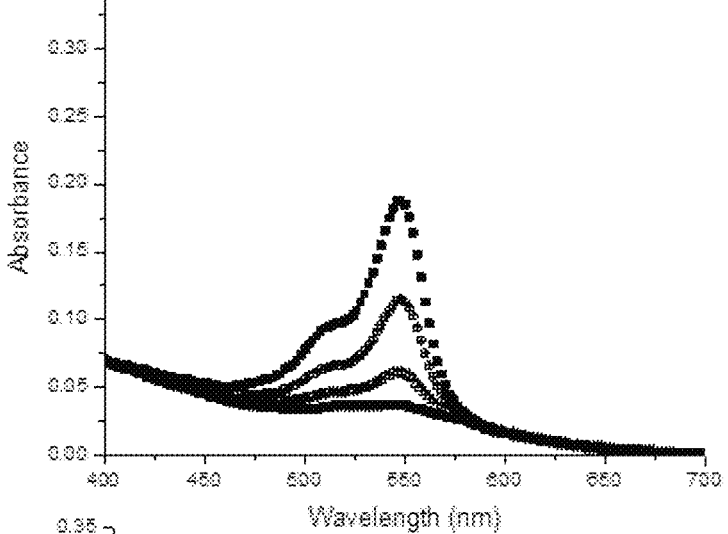
Figure 31C:
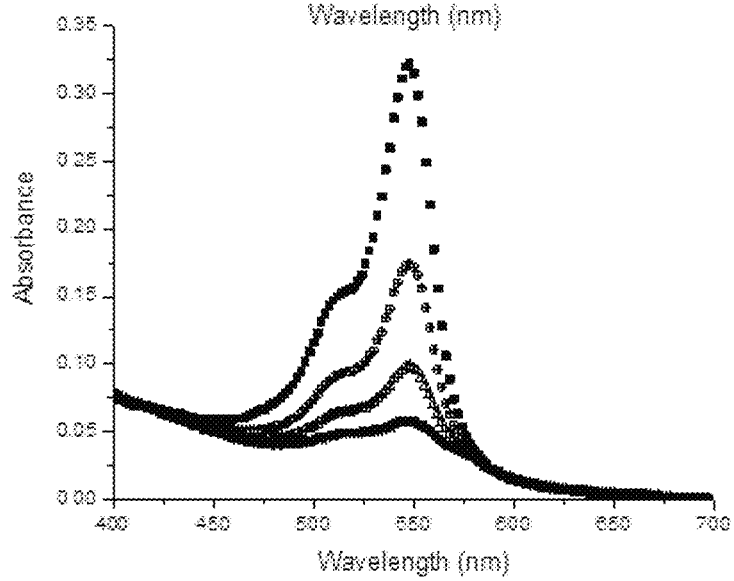

100 μL of samples each comprising one of 2.00 RB nanoparticles, 3.00 RB nanoparticles, 4.00 RB nanoparticles, and 6.00 RB nanoparticles were mixed with 200 μL of water and 0.1 μL, 0.05 μL, or 0.03 μL of DFP. FIGS. 29A-29C are spectra of 2.00 RB, 4.00 RB, and 6.00 RB, respectively, in a 1:20 dilution with DFP; FIGS. 30A-30C are spectra of 3.00 RB, 4.00 RB, and 6.00 RB, respectively, in a 1:30 dilution with DFP; and FIGS. 31A-31C are spectra of 3.00 RB, 4.00 RB, and 6.00 RB, respectively, in a 1:10 dilution with DFP.

Figure 32A:
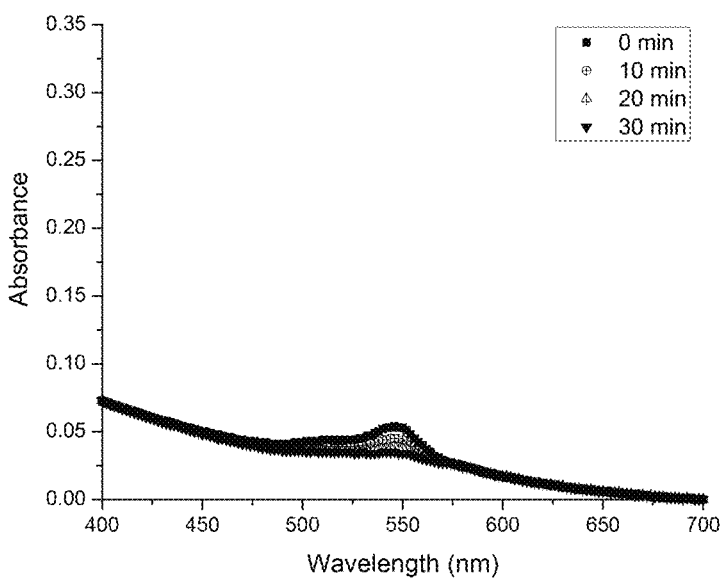
FIGS. 32A-32C are spectra of 3.00 RB, 4.00 RB, and 6.00 RB, respectively, in a 1:20 dilution with bis(2-chloroethyl) sulfide.
Figure 32B:
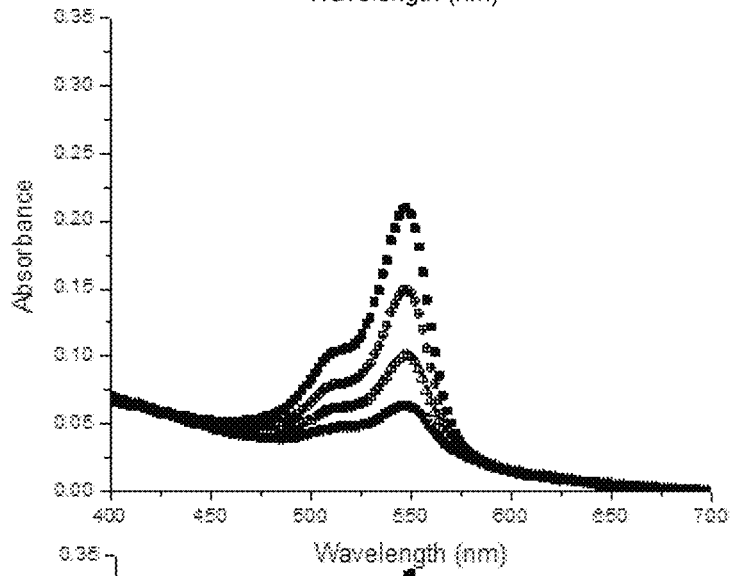
Figure 32C:
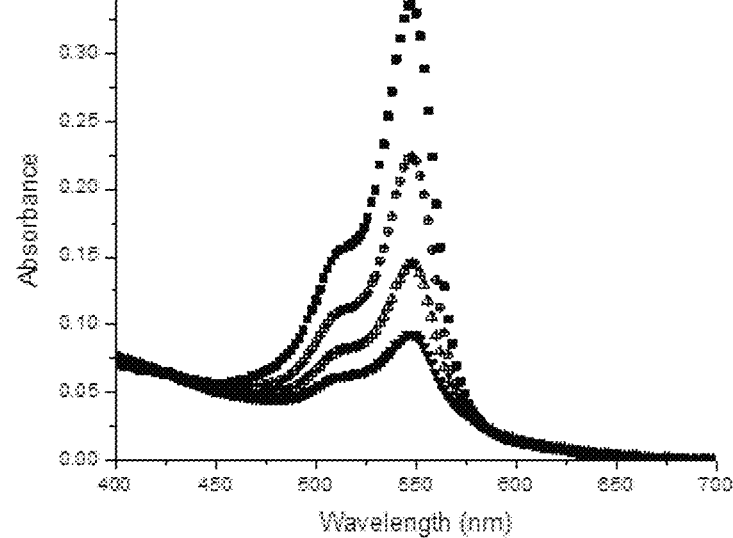
Figure 33A:
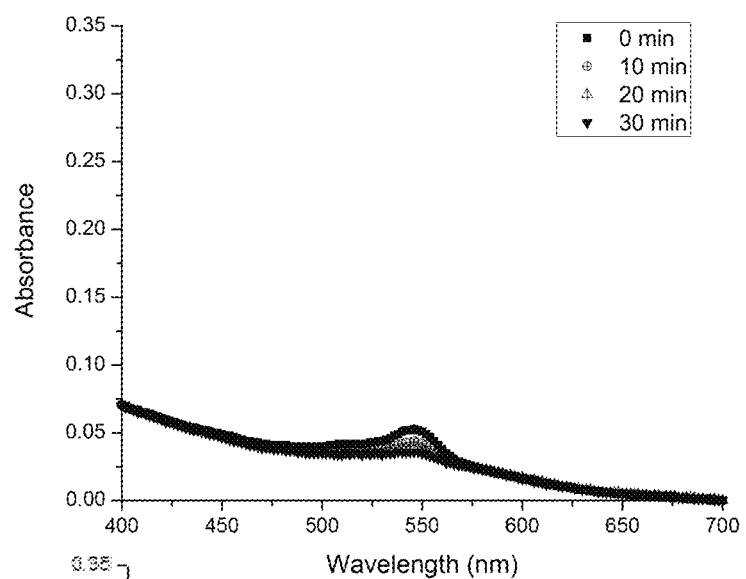
FIGS. 33A-33C are spectra of 3.00 RB, 4.00 RB, and 6.00 RB, respectively, in a 1:40 dilution with bis(2-chloroethyl) sulfide.
Figure 33B:
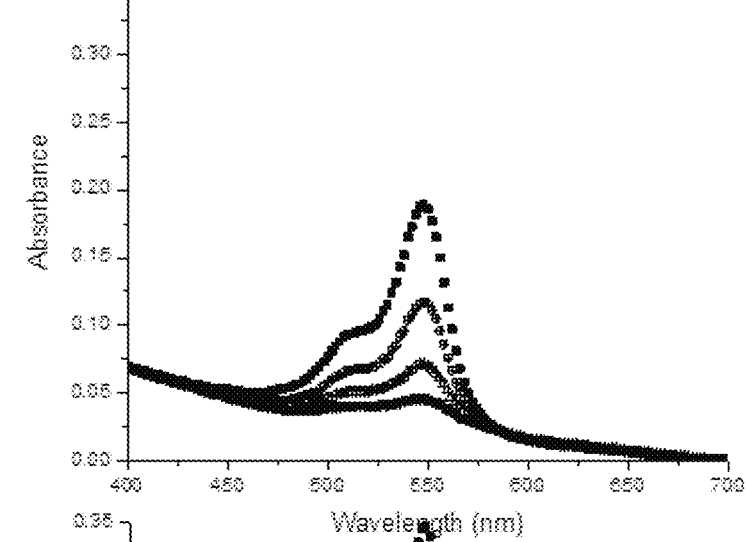
Figure 33C:
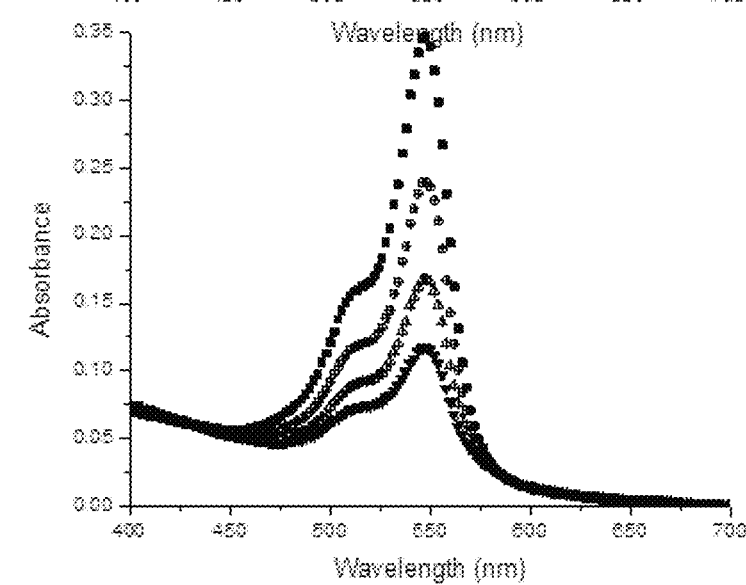
Figure 34A:
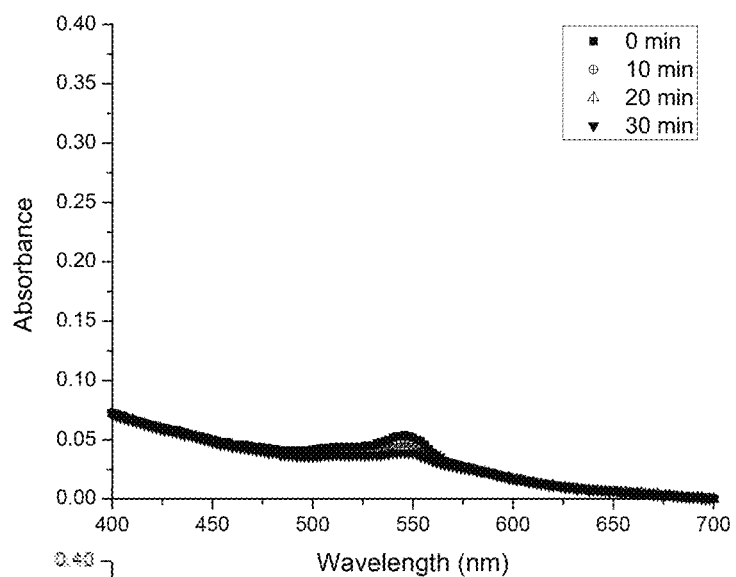
FIGS. 34A-34C are spectra of 3.00 RB, 4.00 RB, and 6.00 RB, respectively, in a 1:60 dilution with bis(2-chloroethyl) sulfide.
Figure 34B:
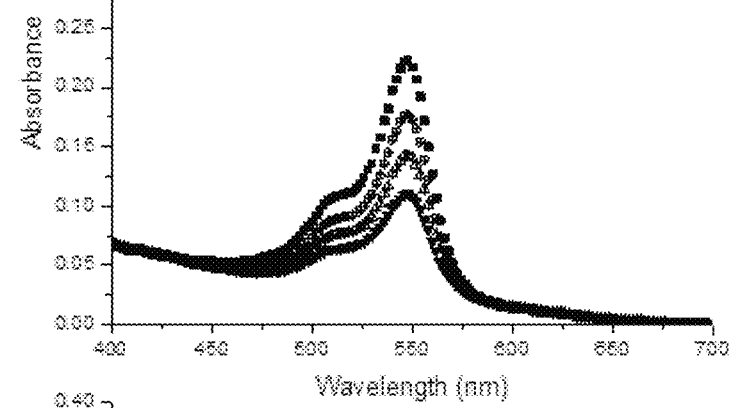
Figure 34C:
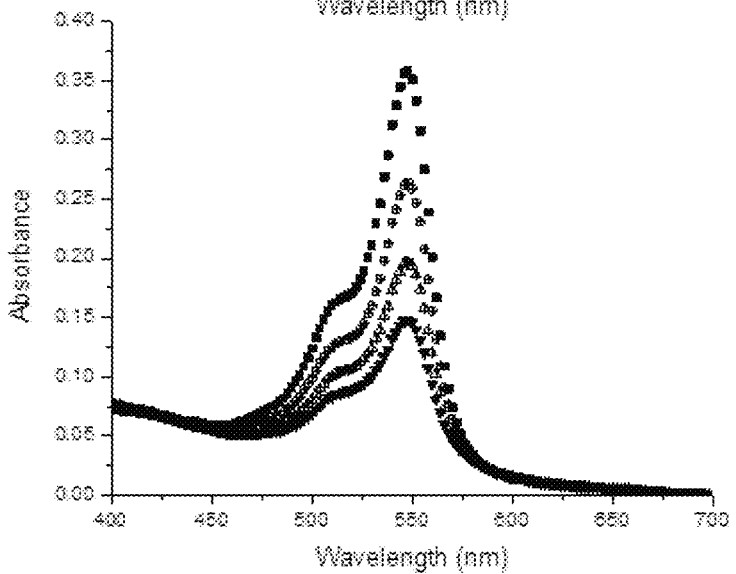
Figure 35A:
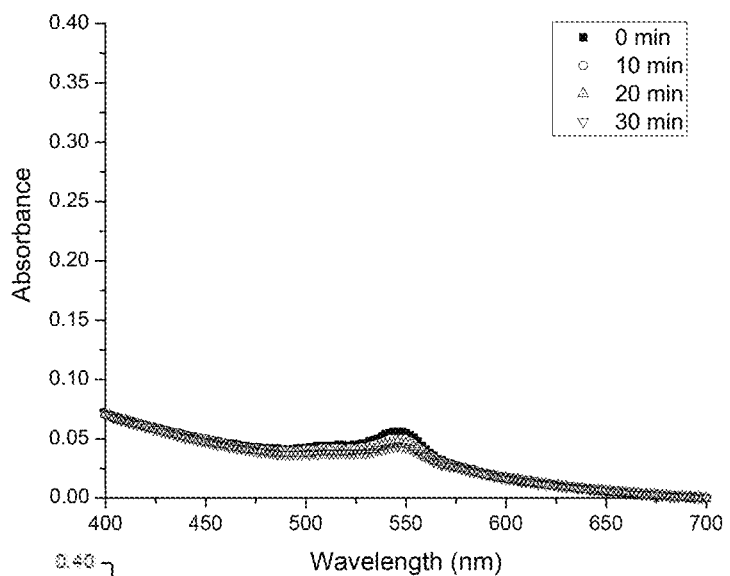
FIGS. 35A-35C are spectra of 3.00 RB, 4.00 RB, and 6.00 RB, respectively, in a 1:40 dilution with bis(2-chloroethyl) sulfide.
Figure 35B:
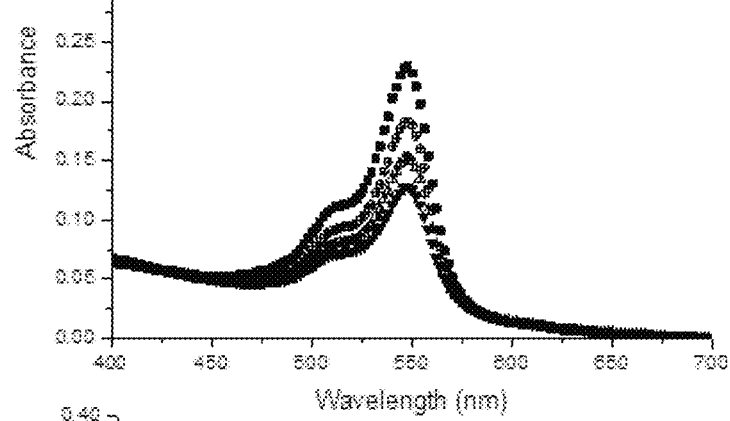
Figure 35C:
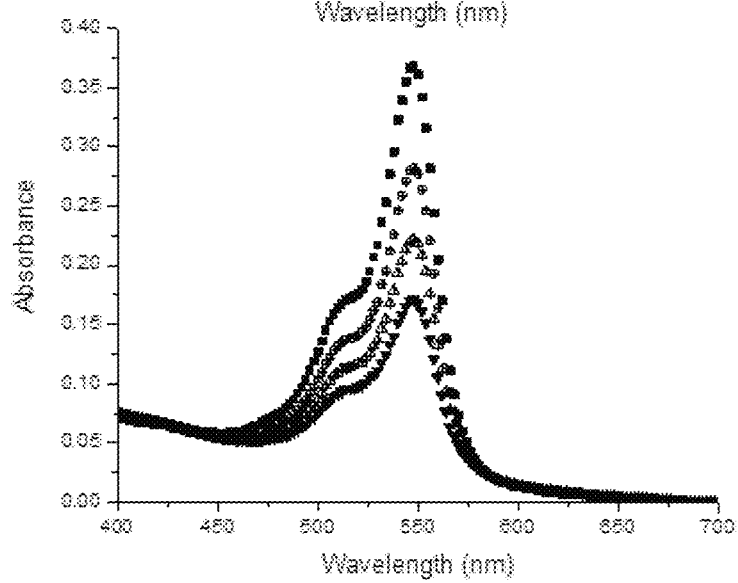
Figure 36A:
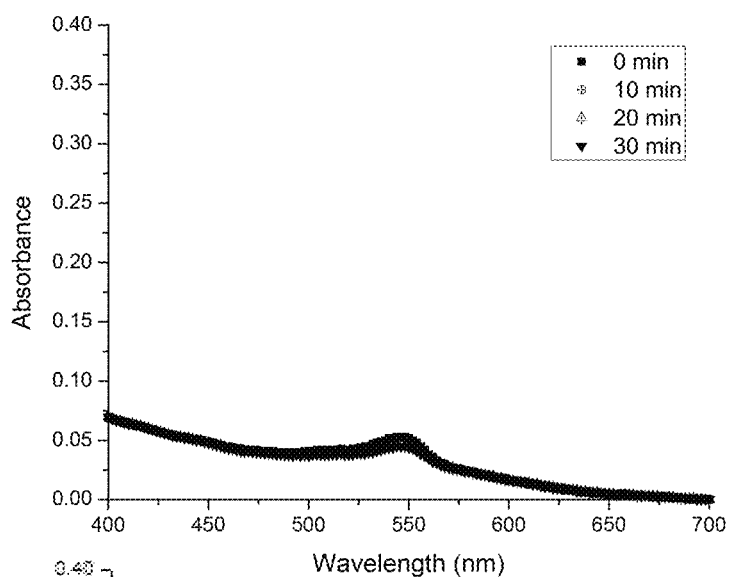
FIGS. 36A-36C are spectra of 3.00 RB, 4.00 RB, and 6.00 RB, respectively, in a 1:160 dilution with bis(2-chloroethyl) sulfide.
Figure 36B:
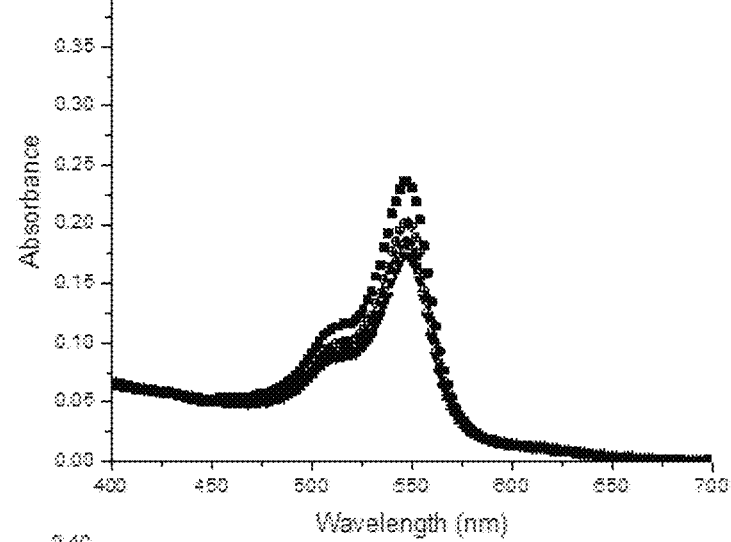
Figure 36C:
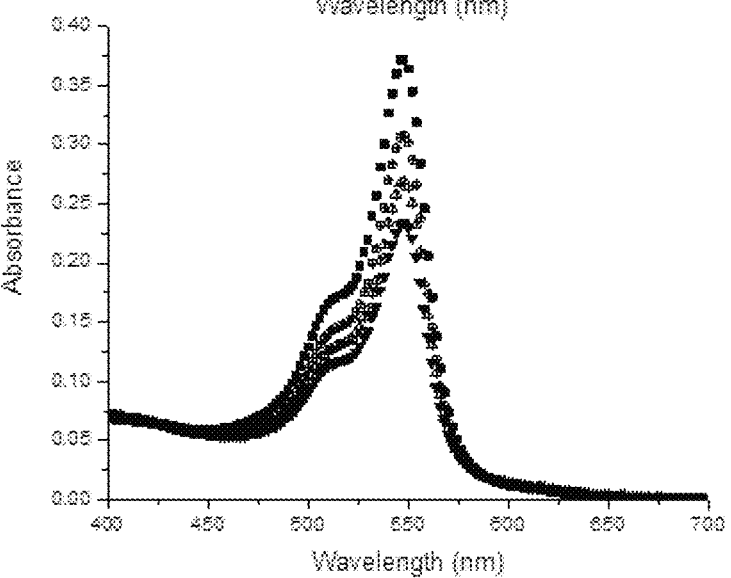

100 μL of samples each comprising one of 3.00 mg RB nanoparticles, 4.00 mg RB nanoparticles, and 6.00 mg of RB nanoparticles sample were mixed with 200 μL of water and 0.1 μL, 0.05 μL, or 0.03 μL of Mustard. FIGS. 32A-32C are spectra of 3.00 RB, 4.00 RB, and 6.00 RB, respectively, in a 1:20 dilution with Mustard; FIGS. 33A-33C are spectra of 3.00 RB, 4.00 RB, and 6.00 RB, respectively, in a 1:40 dilution with Mustard; FIGS. 34A-34C are spectra of 3.00 RB, 4.00 RB, and 6.00 RB, respectively, in a 1:60 dilution with Mustard; FIGS. 35A-35C are spectra of 3.00 RB, 4.00 RB, and 6.00 RB, respectively, in a 1:40 dilution with Mustard; and FIGS. 36A-36C are spectra of 3.00 RB, 4.00 RB, and 6.00 RB, respectively, in a 1:160 dilution with Mustard. A detection limit as low as 0.006 μL per 300 μL (100 μL of sample with 200 μL of water) for Mustard was determined.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of detecting presence of a chemical warfare agent, the method comprising:
  acquiring a first spectrum comprising an electromagnetic radiation absorption and a second spectrum comprising a fluorescent signature at 450 nm, 485 nm, or both of a substrate having a first dye applied thereto, the first dye being the quinoid isomer of Rose Bengal;
  exposing the substrate to an environment;
  acquiring a third spectrum comprising an electromagnetic radiation absorption and a fourth spectrum comprising a fluorescent signature at 450 nm, 485 nm, or both of the exposed substrate;
  comparing the third spectrum to the first spectrum; and
  comparing the fourth spectrum to the second spectrum,
    wherein if the comparison of the third and first spectra shows a decrease in absorption at wavelengths less than about 600 nm and greater than about 450 nm and if the comparison of the fourth and second spectra shows an increase in fluorescence at 450 nm, 485 nm, or both, then a chemical warfare agent in the environment induced a conformational change of the quinoid isomer of Rose Bengal to a lactone isomer of Rose Bengal and substrate exposure to the chemical warfare agent is confirmed, the chemical warfare agent selected from the group consisting of a nerve chemical warfare agent and a blister chemical warfare agent, and wherein if there is no change between the third and first spectra or between the fourth and second spectrum, then the quinoid isomer of Rose Bengal remains and the substrate was not exposed to the chemical warfare agent.

2. The method of claim 1, further comprising:

before exposing the substrate and after applying the first dye, applying a secondary second dye to the substrate.

3. The method of claim 2, wherein the second dye is Rhodamine 560, Rhodamine 640, or both.

4. The method of claim 1, wherein applying the quinoid isomer of Rose Bengal further comprises:

binding the quinoid form of Rose Bengal to the substrate.

5. The method of claim 4, wherein binding the quinoid isomer of Rose Bengal includes functionalization, encapsulation, or trapping.

6. The method of claim 1, wherein applying the quinoid isomer of Rose Bengal further comprises:

binding the quinoid isomer of Rose Bengal to nanoparticles; and cross-linking the nanoparticles to the substrate.

7. The method of claim 1, further comprising:

decomposing the chemical warfare agent by a Rose Bengal induced photocatalytic oxidation mechanism.

8. The method of claim 7, wherein decomposing the chemical warfare agent further comprises:

exposing the chemical warfare agent to light having a wavelength within the visible spectrum.

9. A method of detecting presence of a chemical warfare agent, the method comprising:

providing a substrate, the substrate comprising:
a fabric, a polymer, or both;
a coating comprising a first dye and a second dye applied to the fabric, the polymer, or both, the first dye being the quinoid isomer of Rose Bengal and the second dye being Rhodamine 560, Rhodamine 640, or both;

spectroscopically measuring a first electromagnetic radiation absorption spectrum of the provided substrate and a first fluorescence signature of the provided substrate at 450 nm and 485 nm; and after a use time, spectroscopically measuring a second electromagnetic radiation absorption spectrum of the used substrate and a second fluorescence signature at 450 nm and 485 nm of the used substrate;

comparing the first electromagnetic radiation absorption spectrum to the second electromagnetic radiation absorption spectrum and the first fluorescence signature to the second fluorescence signature; and if the comparison of the first electromagnetic radiation absorption spectrum to the second electromagnetic radiation absorption spectrum shows a decrease in absorption at wavelengths less than about 600 nm and greater than about 450 nm and the comparison of the first fluorescence signature to the second fluorescence signature shows an increase in fluorescence 450 nm and 485 nm, then a chemical warfare agent induced a conformational change of the quinoid isomer of Rose Bengal to the lactone isomer of Rose Bengal during the use time and concluding the used substrate was exposed to a chemical warfare agent selected from the group consisting of a nerve chemical warfare agent and a blister chemical warfare agent;

and if the comparison of the first electromagnetic radiation absorption spectrum to the second electromagnetic radiation absorption spectrum shows no change and the comparison of the first fluorescence signature to the second fluorescence signature shows no change, concluding there is no conformational change of the quinoid isomer and concluding the used substrate was not exposed to the chemical warfare agent.

10. The method of claim 1, further comprising:

before exposing the substrate, making a solution of the first dye with a secondary dye and, applying the solution to the substrate.

11. The method of claim 9, wherein the coating comprising a first layer of the first dye and a second layer of the second dye.

* * * * *